United States Patent
Pechan et al.

(10) Patent No.: US 10,183,983 B2
(45) Date of Patent: Jan. 22, 2019

(54) NUCLEIC ACIDS ENCODING FUSION PROTEINS COMPRISING PDGF AND VEGF BINDING PORTIONS AND METHODS OF USING THEREOF

(71) Applicant: Genzyme Corporation, Cambridge, MA (US)

(72) Inventors: Peter Pechan, Bridgewater, NJ (US); Jeffery Ardinger, Bridgewater, NJ (US); Hillard Rubin, Bridgewater, NJ (US); Samuel Wadsworth, Shrewsbury, MA (US); Abraham Scaria, Framingham, MA (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 15/471,725

(22) Filed: Mar. 28, 2017

(65) Prior Publication Data
US 2017/0342127 A1    Nov. 30, 2017

Related U.S. Application Data

(62) Division of application No. 14/210,354, filed on Mar. 13, 2014, now Pat. No. 9,637,534.

(60) Provisional application No. 61/780,914, filed on Mar. 13, 2013.

(51) Int. Cl.
| | |
|---|---|
| C12N 15/62 | (2006.01) |
| C12N 15/63 | (2006.01) |
| C12N 15/06 | (2006.01) |
| C12N 15/86 | (2006.01) |
| C12N 15/861 | (2006.01) |
| C07K 14/71 | (2006.01) |
| A61K 38/00 | (2006.01) |

(52) U.S. Cl.
CPC ............. *C07K 14/71* (2013.01); *A61K 38/00* (2013.01); *C07K 2319/30* (2013.01); *C07K 2319/70* (2013.01); *C12N 2510/02* (2013.01); *C12N 2750/14143* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,454,151 A | 6/1984 | Waterbury |
| 4,560,655 A | 12/1985 | Baker |
| 4,657,866 A | 4/1987 | Kumar |
| 4,767,704 A | 8/1988 | Cleveland et al. |
| 4,927,762 A | 5/1990 | Darfler |
| 4,952,515 A | 8/1990 | Gleisner |
| 5,122,469 A | 6/1992 | Mather et al. |
| 5,328,470 A | 7/1994 | Nable et al. |
| 5,476,511 A | 12/1995 | Gwon et al. |
| 5,501,856 A | 3/1996 | Ohtori et al. |
| 5,631,144 A | 5/1997 | Lemoine et al. |
| 5,686,572 A | 11/1997 | Wolf et al. |
| 6,331,313 B1 | 12/2001 | Wong et al. |
| 6,566,118 B1 | 5/2003 | Atkinson et al. |
| 6,989,264 B2 | 1/2006 | Atkinson et al. |
| 6,995,006 B2 | 2/2006 | Atkinson et al. |
| 7,771,829 B2 | 8/2010 | Hilmer et al. |
| 7,928,072 B2 | 4/2011 | Scaria et al. |
| 9,637,534 B2 | 5/2017 | Pechan et al. |
| 2003/0181531 A1 | 9/2003 | Sherris et al. |
| 2004/0058313 A1 | 3/2004 | Abreu |
| 2006/0234347 A1 | 10/2006 | Harding et al. |
| 2011/0177074 A1 | 7/2011 | Sivakumar et al. |
| 2012/0251531 A1 | 10/2012 | Baehner et al. |

FOREIGN PATENT DOCUMENTS

| | | |
|---|---|---|
| CA | 2 831 161 A1 | 11/2012 |
| CN | 102 311 502 A | 1/2012 |
| EA | 005404 B1 | 2/2005 |
| JP | 2008-512127 A | 4/2008 |
| JP | 2008-536498 A | 9/2008 |
| JP | 2011-512417 A | 4/2011 |
| JP | 2011-518546 A | 6/2011 |
| WO | WO-87/00195 A1 | 1/1987 |
| WO | WO-90/03430 A1 | 4/1990 |
| WO | WO-90/13646 A1 | 11/1990 |
| WO | WO-00/24782 A2 | 5/2000 |
| WO | WO-03/077796 A2 | 9/2003 |
| WO | WO-03/077796 A3 | 9/2003 |
| WO | WO-2006/031689 A2 | 3/2006 |
| WO | WO-2006/113277 A2 | 10/2006 |
| WO | WO-2006/113277 A3 | 10/2006 |
| WO | WO-2009/105669 A2 | 8/2009 |
| WO | WO-2009/105669 A3 | 8/2009 |
| WO | WO-2009/120922 A2 | 10/2009 |
| WO | WO-2012/075184 A2 | 6/2012 |

OTHER PUBLICATIONS

Blokhin D. Yu. et al. (2011). "Molecular Targets for Antitumor Therapy: Growth Factors, Angiogenesis and Apoptosis," *Russian Biotherapeutic Journal* 10(3):17-24, 17 pages. (English Translation).

Liang F. Q. et al. (Nov. 2001). "Long-term Protection of Retinal Structure but not Function Using RAAV. CNTF in Animal Models of Retinitis Pigmentosa," *Molecular Therapy* 4(5):461-472.

Suen K. F. et al. (May 2010). "Transient Expression of an IL-23R Extracellular Domain Fc Fusion Protein in CHO vs. HEK Cells Results in Improved Plasma Exposure," *Protein Expression and Purification* 71(1):96-102, 7 pages.

(Continued)

*Primary Examiner* — Christine J Saoud
*Assistant Examiner* — Jon M Lockard
(74) *Attorney, Agent, or Firm* — Morrison & Foerster LLP

(57) ABSTRACT

The present provides fusion proteins comprising PDGF and VEGF binding portions, and recombinant viral particles encoding the fusion proteins. Compositions comprising the fusion proteins and viral particles as well as methods of using the same are also provided.

8 Claims, 8 Drawing Sheets

Specification includes a Sequence Listing.

(56) References Cited

OTHER PUBLICATIONS

Aiello, L.P. et al. (Nov. 1995). "Suppression of Retinal Neovascularization In Vivo by Inhibition of Vascular Endothelial Growth Factor (VEGF) Using Soluble VEGF-Receptor Chimeric Proteins", *Proc Natl Acad Sci U S A*. 92(23):10457-10461.

Ali, R.R. et al. (Jan. 1, 1998). "Adeno-Associated Virus Gene Transfer to Mouse Retina", *Hum. Gene Ther.* 9(1):81-6.

Ali, R.R. et al. (May 1996). "Gene Transfer Into the Mouse Retina Mediated by an Adeno-Associated Viral Vector", *Hum. Mol. Genet.* 5(5):591-594.

Ali, R.R. et al. (Sep. 1997). "Gene Therapy for Inherited Retinal Degeneration", *Br. J. Opthalmol.* 81(9):795-801.

Altschuh, D. et al. (Jul. 14, 1992). "Determination of Kinetic Constants for the Interaction Between a Monoclonal Antibody and Peptides Using Surface Plasmon Resonance", *Biochem.* 31(27):6298-6304.

Barleon, B. et al. (Apr. 18, 1997). "Mapping of the Sites for Ligand Binding and Receptor Dimerization at the Extracellular Domain of the Vascular Endothelial Growth Factor Receptor FLT-1", *J Biol Chem.*, 272(16):10382-10388.

Barnes, D. et al. (Mar. 1, 1980). "Methods for Growth of Cultured Cells in Serum-Free Medium", *Anal. Biochem.* 102:255-270.

Benjamin, L.E. et al. (May 1998, e-pub. Apr. 1, 1998). "A Plasticity Window for Blood Vessel Remodelling is Defined by Pericyte Coverage of the Preformed Endothelial Network and is Regulated by PDGF-B and VEGF", *Development* 125(9)1591-1598.

Bossis, I. et al. (Jun. 2003). "Cloning of an Avian Adeno-Associated Virus (AAAV) and Generation of Recombinant AAAV Particles", *J. Virol.* 77(12):6799-6810.

Chen, S.H. et al. (Apr. 1994). "Gene Therapy for Brain Tumors: Regression of Experimental Gliomas by Adenovirus-Mediated Gene Transfer in Vivo", *Proc Natl Acad Sci U S A*. 91(8):3054-3057.

Connolly, D.T. et al. (Nov. 1989). "Tumor Vascular Permeability Factor Stimulates Endothelial Cell Growth and Angiogenesis", *J. Clin. Invest.* 84(5):1470-1478.

Cunningham, B.C. et al. (Jun. 2, 1989). "High-Resolution Epitope Mapping of hGH-Receptor Interactions by Alannie-Scanning Mutagenesis", *Science* 244:1081-1085.

Davidson, B.L. et al. (Mar. 28, 2000). "Recombinant Adeno-Associated Virus Type 2, 4, and 5 Vectors: Transduction of Variant Cell Types and Regions in the Mammalian Central Nervous System", *Proc Natl Acad Sci U S A*. 97(7)3428-3432.

Davis-Smyth, T. et al. (Sep. 16, 1996). "The Second Immunoglobulin-Like Domain of the VEGF Tyrosine Kinase Receptor Flt-1 Determines Ligand Binding and May Initiate a Signal Transduction Cascade", *EMBO J.* 15:4919-4927.

Davis-Smyth, T.et al. (Feb. 6, 1998). "Mapping the Charged Residues in the Second Immunoglobulin-Like Domain of the Vascular Endothelial Growth Factor/Placenta Growth Factor Receptor Flt-1 Required for Binding and Structural Stability", *J. Biol. Chem.* 273(6):3216-3222.

Duan, D.S. et al. (Jan. 5, 1991). "A Functional Soluble Extracellular Region of the Platelet-Derived Growth Factor (PDGF) β-Receptor Antagonizes PDGF-Stimulated Responses", *J. Biol. Chem.* 266(1)413-418.

Ferrara, N. et al. (Jun. 15, 1989). "Pituitary Follicular Cells Secrete a Novel Heparin-Binding Growth Factor Specific for Vascular Endothelial Cells", *Biochem. Biophys. Res. Commun.* 161(2):851-859.

Ferrara, N. et al. (Mar. 1998). "Vascular Endothelial Growth Factor is Essential for Corpus Luteum Angiogenesis", *Nat. Med.* 4(3):336-340.

Gao, G. et al. (May 13, 2003, e-pub. Apr. 25, 2003). "Adeno-Associated Viruses Undergo Substantial Evolution in Primates During Natural Infections", *Proc Natl Acad Sci U S A*. 100(10):6081-6086.

Gao, G.P. et al. (Sep. 3, 2002, e-pub. Aug. 21, 2002). "Novel Adeno-Associated Viruses From Rhesus Monkeys as Vectors for Human Gene Therapy", *Proc Natl Acad Sci U S A*. 99(18):11854-11856.

Guo, Z.S. et al. (Sep. 1996). "Evaluation of Promoter Strength for Hepatic Gene Expression in Vivo Following Adenovirus-Mediated Gene Transfer", *Gene Ther.* 3(9):802-10.

Ham, R.G. et al. (1979). "Media and Growth Requirements", *Meth. Enz.* 58:44-93.

Heidaran, M.A. et al. (Jan. 1995). "β PDGFR-IgG Chimera Demonstrates That Human β PDGFR Ig-Like Domains 1 to 3 are Sufficient for High Affinity PDGF BB Binding", *FASEB J.* 9(1):140-145.

Hellström, M. et al. (Jun. 1999, e-pub. Jun. 21, 1999). "Role of PDGF-B and PDGFR-β in Recruitment of Vascular Smooth Muscle Cells and Pericytes During Embryonic Blood Vessel Formation in the Mouse", *Development* 126:3047-3055.

Hodgson, D.R.W. et al. (Sep. 2004, e-pub. Aug. 13, 2004). "The Synthesis of Peptides and Proteins Containing Non-Natural Amino Acids", *Chem. Soc. Rev.* 33:422-430.

Holash, J. et al. (Aug. 20, 2002). "VEGF-Trap: A VEGF Blocker With Potent Antitumor Effects", *Proc Natl Acad Sci U S A*. 99(17):11393-11398.

International Search Report dated Jul. 28, 2014, for PCT Application No. PCT/US2014/026872, filed on Mar. 13, 2014, 5 pages.

Kendall, R.L. et al. (Nov. 15, 1993). "Inhibition of Vascular Endothelial Cell Growth Factor Activity by an Endogenously Encoded Soluble Receptor", *Proc Natl Acad Sci U S A*. 90:10705-10709.

Kim, D.W. et al. (Jul. 1990). "Use of the Human Elongation Factor 1α Promoter as a Versatile and Efficient Expression System", *Gene* 91(2):217-23.

Kotin, R.M. (Jul. 1994). "Prospects for the Use of Adeno-Associated Virus as a Vector for Human Gene Therapy", *Hum. Gene Ther.* 5:793-801.

Lai, C-M. et al. (Oct. 2005, e-pub. Jul. 14, 2005). "Long-Term Evaluation of AAV-Mediated sFlt-1 Gene Therapy for Ocular Neovascularization in Mice and Monkeys", *Mol. Ther.* 12(4):659-68.

Leppänen, O. et al. (Mar. 2000, e-pub. Feb. 12, 2000). "Predimerization of Recombinant Platelet-Derived Growth Factor Receptor Extracellular Domains Increases Antagonistic Potency", *Biochemistry* 39(9):2370-2375.

Lindahl, P. et al. (Oct. 1997)."Alveogenesis Failure in PDGF-A-Deficient Mice is Coupled to Lack of Distal Spreading of Alveolar Smooth Muscle Cell Progenitors During Lung Development", *Development* 124:3943-3953.

Lindmark, R. et al. (Aug. 12, 1983). "Binding of Immunoglobulins to Protein A and Immunoglobulin Levels in Mammalian Sera", *J. Immunol. Meth.* 62:1-13.

Lokker, N.A. et al. (Dec. 26, 1997). "Functional Importance of Platelet-Derived Growth Factor (PDGF) Receptor Extracellular Immunoglobulin-Like Domains. Identification of PDGF Binding Site and Neutralizing Monoclonal Antibodies", *J. Biol Chem.* 272(52):33037-33044.

Mahadevan, D. et al. (Nov. 17, 1995). "Structural Role of Extracellular Domain 1 of α-Platelet-Derived Growth Factor (PDGF) Receptor for PDGF-AA and PDGF-BB Binding",*J. Biol. Chem.* 270(46):27595-27600.

Mandel, M. et al. (Oct. 14, 1970). "Calcium-Dependent Bacteriophage DNA Infection", *J. Mol. Biol.* 53(1):159-162.

Matsui, T. et al. (Feb. 10, 1989). "Isolation of a Novel Receptor cDNA Establishes the Existence of Two PDGF Receptor Genes", *Science* 243:800-803.

Miyazawa, K. et al. (Sep. 25, 1998). "Role of Immunoglobulin-Like Domains 2-4 of the Platelet-Derived Growth Factor α-Receptor in Ligand-Receptor Complex Assembly", *J. Biol Chem.* 273(39):25495-502.

Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.

(56) References Cited

OTHER PUBLICATIONS

Niwa, H. et al. (Dec. 15, 1991). "Efficient Selection for High-Expression Transfectants With a Novel Eukaryotic Vector", *Gene* 108(2):193-199.

Ozawa, T. et al. (Apr. 2009). "The Functional Analysis of a Novel KDR (VEGFR II)-PDGFR-Alpha Fusion Gene in Glioblastoma: From Discovery to Clinical Application," American Association for Cancer Research, Proceedings of the Annual Meeting, Denver, Co., Apr. 18-22, 2009., Abstract No. 5609, 1 page.

Passini, M.A. et al. (Jun. 2003). "Intraventricular Brain Injection of Adeno-Associated Virus Type 1 (AAV1) in Neonatal Mice Results in Complementary Patterns of Neuronal Transduction to AAV2 and Total Long-Term Correction of Storage Lesions in the Brains of β-Glucuronidase-Deficient Mice", *J. Virol.* 77(12):7034-7040.

Patel, S. (Jun. 2009). "Combination Therapy for Age-Related Macular Degeneration", *Retina* 29(6 Suppl.):S45-S48.

Pechan, P. et al. (Jan. 2009, e-pub. Jul. 17, 2008). "Novel Anti-VEGF Chimeric Molecules Delivered by AAV Vectors for Inhibition of Retinal Neovascularization", *Gene Ther.* 16:10-16.

Raghava, S. et al. (Nov. 2004). "Periocular Routes for Retinal Drug Delivery", *Expert Opin. Drug Deliv.* 1(1):99-114.

Robbins, S.G. et al. (Sep. 1994). "Platelet-Derived Growth Factor Ligands and Receptors Immunolocalized in Proliferative Retinal Diseases", *Invest. Opth. Vis. Sci.* 35(10):3649-3663.

Roskoski, R et al. (Jun. 2007). "Vascular Endothelial Growth Factor (VEGF) Signaling in Tumor Progression," *Crit. Rev. Oncol. Hematol.* 62(3):179-213.

Sandberg, M. et al. (Jul. 1998, e-pub. Jun. 4, 1998). "New Chemical Descriptors Relevant for the Design of Biologically Active Peptides. A Multivariate Characterization of 87 Amino Acids", *J. Med. Chem.* 41(14):2481-2491.

Shibuya, M. et al. (Apr. 1990). "Nucleotide Sequence and Expression of a Novel Human Receptor-Type Tyrosine Kinase Gene (flt) Closely Related to the fms Family", *Oncogene* 5(4):519-524.

Tam, J.P. (Sep. 13, 1996). "Recent Advances in Multiple Antigen Peptides", *J. of Immunol. Methods* 196:17-32.

Ueno, H. et al. (May 10, 1991). "Inhibition of PDGF β Receptor Signal Transduction by Coexpression of a Truncated Receptor", *Science* 252(5007):844-848.

Vincent, K.A. at al. (Mar. 1997). "Analysis of Recombinant Adeno-Associated Virus Packaging and Requirements for rep and cap Gene Products", *J. Virol.* 71(3): 1897-1905.

Wells, J.A. (Sep. 18, 1990). "Additivity of Mutational Effects in Proteins", *Biochemistry* 29(37):8509-8517.

Wiesmann, C. et al. (Nov. 28, 1997). "Crystal Structure at 1.7 Å Resolution of VEGF in Complex With Domain 2 of the Flt-1 Receptor", *Cell* 91:695-704.

Willet, C.G. et al. (Feb. 2004, e-pub. Jan. 25, 2004). "Direct Evidence that the VEGF-Specific Antibody Bevacizumab has Antivascular Effects in Human Rectal Cancer", *Nat. Med.* 10:145-147.

Written Opinion dated Jul. 28, 2014, for PCT Application No. PCT/US2014/026872, filed on Mar. 13, 2014, 6 pages.

Xie, J. et al. (Dec. 2005, e-pub. Nov. 2, 2005). "Adding Amino Acids to the Genetic Repertoire", *Curr. Opin. Chem. Biol.* 9(6):548-554.

Yarden, Y. et al. (Sep. 18-24, 1986). "Structure of the Receptor for Platelet-Derived Growth Factor Helps Define a Family of Closely Related Growth Factor Receptors", *Nature* 323:226-232.

Ziegler, R.J. et al. (Feb. 2004). "AAV2 Vector Harboring a Liver-Restricted Promoter Facilitates Sustained Expression of Therapeutic Levels of α-Galactosidase A and the Induction of Immune Tolerance in Fabry Mice", *Mol. Ther.* 9(2):231-240.

Frankel A.E. et al.(2000). Characterization of Diphtheria Fusion Proteins Targeted to The Human Interleukin-3 Receptor, *Protein engineering* 13(8)575-581, abstract, pp. 579-580.

Pakula, A.A. et al. (1989). "Genetic Analysis of Protein Stability and Function", *Annu Rev Genet.* 23:289-310.

Shpakov, A.O.(2017). Glycosilation of Gonadotropins, As the Most Important Mechanism of Regulation of Their Activity, I.M. Sechnov *Russian Physiological Journal*, 103(9):1004-1021 and1011-1015. (English Abstract Only).

Skosyrev, V.S. et al. (Sep.-Oct. 2001). The Dependence of Stability of the Green Fluorescent Protein-Obelin Hybrids on the Nature of Their Constituent Modules and the Structure of the Amino Acid Linker, *Bioorganic Chemistry* 27(5):364-371.

SEQUENCE LISTING

<160> NUMBER OF SEQ ID NOS: 50

<210> SEQ ID NO 1
<211> LENGTH: 283
<212> TYPE: PRT
<213> ORGANISM: Homo sapiens

<400> SEQUENCE: 1

```
Leu Val Val Thr Pro Gly Pro Glu Leu Val Leu Asn Val Ser Ser
 1               5                  10                  15

Thr Phe Val Leu Thr Cys Ser Gly Ser Ala Pro Val Val Trp Glu Arg
             20                  25                  30

Met Ser Gln Glu Pro Pro Gln Glu Met Ala Lys Ala Gln Asp Gly Thr
         35                  40                  45

Phe Ser Ser Val Leu Thr Leu Thr Asn Leu Thr Gly Leu Asp Thr Gly
     50                  55                  60

Glu Tyr Phe Cys Thr His Asn Asp Ser Arg Gly Leu Glu Thr Asp Glu
 65                  70                  75                  80

Arg Lys Arg Leu Tyr Ile Phe Val Pro Asp Pro Thr Val Gly Phe Leu
                 85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
        115                 120                 125

His Glu Lys Lys Gly Asp Val Ala Leu Pro Val Pro Tyr Asp His Gln
    130                 135                 140
```

```
Arg Gly Phe Phe Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
            165                 170                 175

Leu Gln Val Ser Ser Ile Asn Val Ser Val Asn Ala Val Gln Thr Val
                180                 185                 190

Val Arg Gln Gly Glu Asn Ile Thr Leu Met Cys Ile Val Ile Gly Asn
            195                 200                 205

Glu Val Val Asn Phe Glu Trp Thr Tyr Pro Arg Lys Glu Ser Gly Arg
210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
            245                 250                 255

Tyr Thr Cys Asn Val Thr Glu Ser Val Asn Asp His Gln Asp Glu Lys
                260                 265                 270

Ala Ile Asn Ile Thr Val Val Glu Ser Gly Tyr
            275                 280
```

<210> SEQ ID NO 2
<211> LENGTH: 389
<212> TYPE: PRT
<213> ORGANISM: Homo sapiens

<400> SEQUENCE: 2

```
Leu Val Val Thr Pro Pro Gly Pro Glu Leu Val Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
        35                  40                  45

Phe Ser Ser Val Leu Thr Leu Thr Asn Leu Thr Gly Leu Asp Thr Gly
    50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
        115                 120                 125

His Glu Lys Lys Gly Asp Val Ala Leu Pro Val Pro Tyr Asp His Gln
    130                 135                 140

Arg Gly Phe Phe Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
            165                 170                 175

Leu Gln Val Ser Ser Ile Asn Val Ser Val Asn Ala Val Gln Thr Val
                180                 185                 190

Val Arg Gln Gly Glu Asn Ile Thr Leu Met Cys Ile Val Ile Gly Asn
            195                 200                 205

Glu Val Val Asn Phe Glu Trp Thr Tyr Pro Arg Lys Glu Ser Gly Arg
210                 215                 220

Leu Val Glu Pro Val Thr Asp Phe Leu Leu Asp Met Pro Tyr His Ile
225                 230                 235                 240
```

-continued

```
Arg Ser Ile Leu His Ile Pro Ser Ala Glu Leu Glu Asp Ser Gly Thr
            245                 250                 255

Tyr Thr Cys Asn Val Thr Glu Ser Val Asn Asp His Gln Asp Glu Lys
        260                 265                 270

Ala Ile Asn Ile Thr Val Val Glu Ser Gly Tyr Val Arg Leu Leu Gly
    275                 280                 285

Glu Val Gly Thr Leu Gln Phe Ala Glu Leu His Arg Ser Arg Thr Leu
290                 295                 300

Gln Val Val Phe Glu Ala Tyr Pro Pro Thr Val Leu Trp Phe Lys
305                 310                 315                 320

Asp Asn Arg Thr Leu Gly Asp Ser Ser Ala Gly Glu Ile Ala Leu Ser
            325                 330                 335

Thr Arg Asn Val Ser Glu Thr Arg Tyr Val Ser Glu Leu Thr Leu Val
        340                 345                 350

Arg Val Lys Val Ala Glu Ala Gly His Tyr Thr Met Arg Ala Phe His
    355                 360                 365

Glu Asp Ala Glu Val Gln Leu Ser Phe Gln Leu Gln Ile Asn Val Pro
370                 375                 380

Val Arg Val Leu Glu
385

<210> SEQ ID NO 3
<211> LENGTH: 499
<212> TYPE: PRT
<213> ORGANISM: Homo sapiens

<400> SEQUENCE: 3

Leu Val Val Thr Pro Pro Gly Pro Glu Leu Val Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
        35                  40                  45

Phe Ser Ser Val Leu Thr Leu Thr Asn Leu Thr Gly Leu Asp Thr Gly
    50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
        115                 120                 125

His Glu Lys Lys Gly Asp Val Ala Leu Pro Val Pro Tyr Asp His Gln
    130                 135                 140

Arg Gly Phe Phe Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
            180                 185                 190

Val Arg Gln Gly Glu Asn Ile Thr Leu Met Cys Ile Val Ile Gly Asn
        195                 200                 205

Glu Val Val Asn Phe Glu Trp Thr Tyr Pro Arg Lys Glu Ser Gly Arg
    210                 215                 220
```

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
            245                 250                 255

Tyr Thr Cys Asn Val Thr Glu Ser Val Asn Asp His Gln Asp Glu Lys
            260                 265                 270

Ala Ile Asn Ile Thr Val Val Glu Ser Gly Tyr Val Arg Leu Leu Gly
            275                 280                 285

Glu Val Gly Thr Leu Gln Phe Ala Glu Leu His Arg Ser Arg Thr Leu
            290                 295                 300

Gln Val Val Phe Glu Ala Tyr Pro Pro Thr Val Leu Trp Phe Lys
305                 310                 315                 320

Asp Asn Arg Thr Leu Gly Asp Ser Ser Ala Gly Glu Ile Ala Leu Ser
            325                 330                 335

Thr Arg Asn Val Ser Glu Thr Arg Tyr Val Ser Glu Leu Thr Leu Val
            340                 345                 350

Arg Val Lys Val Ala Glu Ala Gly His Tyr Thr Met Arg Ala Phe His
            355                 360                 365

Glu Asp Ala Glu Val Gln Leu Ser Phe Gln Leu Gln Ile Asn Val Pro
370                 375                 380

Val Arg Val Leu Glu Leu Ser Glu Ser His Pro Asp Ser Gly Glu Gln
385                 390                 395                 400

Thr Val Arg Cys Arg Gly Arg Gly Met Pro Gln Pro Asn Ile Ile Trp
            405                 410                 415

Ser Ala Cys Arg Asp Leu Lys Arg Cys Pro Arg Glu Leu Pro Pro Thr
            420                 425                 430

Leu Leu Gly Asn Ser Ser Glu Glu Ser Gln Leu Glu Thr Asn Val
            435                 440                 445

Thr Tyr Trp Glu Glu Glu Gln Glu Phe Glu Val Val Ser Thr Leu Arg
            450                 455                 460

Leu Gln His Val Asp Arg Pro Leu Ser Val Arg Cys Thr Leu Arg Asn
465                 470                 475                 480

Ala Val Gly Gln Asp Thr Gln Glu Val Ile Val Val Pro His Ser Leu
            485                 490                 495

Pro Phe Lys

<210> SEQ ID NO 4
<211> LENGTH: 94
<212> TYPE: PRT
<213> ORGANISM: Homo sapiens

<400> SEQUENCE: 4

Arg Pro Phe Val Glu Met Tyr Ser Glu Ile Pro Glu Ile Ile His Met
1               5                   10                  15

Thr Glu Gly Arg Glu Leu Val Ile Pro Cys Arg Val Thr Ser Pro Asn
            20                  25                  30

Ile Thr Val Thr Leu Lys Lys Phe Pro Leu Asp Thr Leu Ile Pro Asp
            35                  40                  45

Gly Lys Arg Ile Ile Trp Asp Ser Arg Lys Gly Phe Ile Ile Ser Asn
        50                  55                  60

Ala Thr Tyr Lys Glu Ile Gly Leu Leu Thr Cys Glu Ala Thr Val Asn
65                  70                  75                  80

Gly His Leu Tyr Lys Thr Asn Tyr Leu Thr His Arg Gln Thr
                85                  90

```
<210> SEQ ID NO 5
<211> LENGTH: 300
<212> TYPE: PRT
<213> ORGANISM: Homo sapiens

<400> SEQUENCE: 5

Pro Glu Leu Ser Leu Lys Gly Thr Gln His Ile Met Gln Ala Gly Gln
 1               5                  10                  15

Thr Leu His Leu Gln Cys Arg Gly Glu Ala Ala His Lys Trp Ser Leu
            20                  25                  30

Pro Glu Met Val Ser Lys Glu Ser Glu Arg Leu Ser Ile Thr Lys Ser
        35                  40                  45

Ala Cys Gly Arg Asn Gly Lys Gln Phe Cys Ser Thr Leu Thr Leu Asn
    50                  55                  60

Thr Ala Gln Ala Asn His Thr Gly Phe Tyr Ser Cys Lys Tyr Leu Ala
65                  70                  75                  80

Val Pro Thr Ser Lys Lys Lys Glu Thr Glu Ser Ala Ile Tyr Ile Phe
                85                  90                  95

Ile Ser Asp Thr Gly Arg Pro Phe Val Glu Met Tyr Ser Glu Ile Pro
            100                 105                 110

Glu Ile Ile His Met Thr Glu Gly Arg Glu Leu Val Ile Pro Cys Arg
        115                 120                 125

Val Thr Ser Pro Asn Ile Thr Val Thr Leu Lys Lys Phe Pro Leu Asp
    130                 135                 140

Thr Leu Ile Pro Asp Gly Lys Arg Ile Ile Trp Asp Ser Arg Lys Gly
145                 150                 155                 160

Phe Ile Ile Ser Asn Ala Thr Tyr Lys Glu Ile Gly Leu Leu Thr Cys
                165                 170                 175

Glu Ala Thr Val Asn Gly His Leu Tyr Lys Thr Asn Tyr Leu Thr His
            180                 185                 190

Arg Gln Thr Asn Thr Ile Ile Asp Val Gln Ile Ser Thr Pro Arg Pro
        195                 200                 205

Val Lys Leu Leu Arg Gly His Thr Leu Val Leu Asn Cys Thr Ala Thr
    210                 215                 220

Thr Pro Leu Asn Thr Arg Val Gln Met Thr Trp Ser Tyr Pro Asp Glu
225                 230                 235                 240

Lys Asn Lys Arg Ala Ser Val Arg Arg Arg Ile Asp Gln Ser Asn Ser
                245                 250                 255

His Ala Asn Ile Phe Tyr Ser Val Leu Thr Ile Asp Lys Met Gln Asn
            260                 265                 270

Lys Asp Lys Gly Leu Tyr Thr Cys Arg Val Arg Ser Gly Pro Ser Phe
        275                 280                 285

Lys Ser Val Asn Thr Ser Val His Ile Tyr Asp Lys
    290                 295                 300

<210> SEQ ID NO 6
<211> LENGTH: 231
<212> TYPE: PRT
<213> ORGANISM: Homo sapiens

<400> SEQUENCE: 6

Pro Lys Ser Cys Asp Lys Thr His Thr Cys Pro Pro Cys Pro Ala Pro
 1               5                  10                  15

Glu Leu Leu Gly Gly Pro Ser Val Phe Leu Phe Pro Pro Lys Pro Lys
            20                  25                  30
```

```
Asp Thr Leu Met Ile Ser Arg Thr Pro Glu Val Thr Cys Val Val Val
             35                  40                  45

Asp Val Ser His Glu Asp Pro Glu Val Lys Phe Asn Trp Tyr Val Asp
     50                  55                  60

Gly Val Glu Val His Asn Ala Lys Thr Lys Pro Arg Glu Glu Gln Tyr
 65                  70                  75                  80

Asn Ser Thr Tyr Arg Val Val Ser Val Leu Thr Val Leu His Gln Asp
                     85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Asp Glu Leu Thr Lys
        130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 7
<211> LENGTH: 531
<212> TYPE: PRT
<213> ORGANISM: Homo sapiens

<400> SEQUENCE: 7

Met Arg Leu Pro Gly Ala Met Pro Ala Leu Ala Leu Lys Gly Glu Leu
 1               5                  10                  15

Leu Leu Leu Ser Leu Leu Leu Leu Glu Pro Gln Ile Ser Gln Gly
            20                  25                  30

Leu Val Val Thr Pro Pro Gly Pro Glu Leu Val Leu Asn Val Ser Ser
            35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
 65                  70                  75                  80

Phe Ser Ser Val Leu Thr Leu Thr Asn Leu Thr Gly Leu Asp Thr Gly
                     85                  90                  95

Glu Tyr Phe Cys Thr His Asn Asp Ser Arg Gly Leu Glu Thr Asp Glu
                100                 105                 110

Arg Lys Arg Leu Tyr Ile Phe Val Pro Asp Pro Thr Val Gly Phe Leu
            115                 120                 125

Pro Asn Asp Ala Glu Glu Leu Phe Ile Phe Leu Thr Glu Ile Thr Glu
        130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175
```

```
Arg Gly Phe Phe Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
        195                 200                 205

Leu Gln Val Ser Ser Ile Asn Val Ser Val Asn Ala Val Gln Thr Val
        210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
                260                 265                 270

Arg Ser Ile Leu His Ile Pro Ser Ala Glu Leu Glu Asp Ser Gly Thr
        275                 280                 285

Tyr Thr Cys Asn Val Thr Glu Ser Val Asn Asp His Gln Asp Glu Lys
        290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
                340                 345                 350

Asp Asn Arg Thr Leu Gly Asp Ser Ser Ala Gly Glu Ile Ala Leu Ser
        355                 360                 365

Thr Arg Asn Val Ser Glu Thr Arg Tyr Val Ser Glu Leu Thr Leu Val
        370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415

Val Arg Val Leu Glu Leu Ser Glu Ser His Pro Asp Ser Gly Glu Gln
                420                 425                 430

Thr Val Arg Cys Arg Gly Arg Gly Met Pro Gln Pro Asn Ile Ile Trp
        435                 440                 445

Ser Ala Cys Arg Asp Leu Lys Arg Cys Pro Arg Glu Leu Pro Pro Thr
        450                 455                 460

Leu Leu Gly Asn Ser Ser Glu Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
                500                 505                 510

Ala Val Gly Gln Asp Thr Gln Glu Val Ile Val Val Pro His Ser Leu
        515                 520                 525

Pro Phe Lys
    530

<210> SEQ ID NO 8
<211> LENGTH: 421
<212> TYPE: PRT
<213> ORGANISM: Homo sapiens
```

```
<400> SEQUENCE: 8

Met Arg Leu Pro Gly Ala Met Pro Ala Leu Ala Leu Lys Gly Glu Leu
 1               5                  10                  15

Leu Leu Leu Ser Leu Leu Leu Leu Glu Pro Gln Ile Ser Gln Gly
             20                  25                  30

Leu Val Val Thr Pro Pro Gly Pro Glu Leu Val Leu Asn Val Ser Ser
             35                  40                  45

Thr Phe Val Leu Thr Cys Ser Gly Ser Ala Pro Val Val Trp Glu Arg
 50                  55                  60

Met Ser Gln Glu Pro Pro Gln Glu Met Ala Lys Ala Gln Asp Gly Thr
 65                  70                  75                  80

Phe Ser Ser Val Leu Thr Leu Thr Asn Leu Thr Gly Leu Asp Thr Gly
                 85                  90                  95

Glu Tyr Phe Cys Thr His Asn Asp Ser Arg Gly Leu Glu Thr Asp Glu
                100                 105                 110

Arg Lys Arg Leu Tyr Ile Phe Val Pro Asp Pro Thr Val Gly Phe Leu
            115                 120                 125

Pro Asn Asp Ala Glu Glu Leu Phe Ile Phe Leu Thr Glu Ile Thr Glu
130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Phe Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
            195                 200                 205

Leu Gln Val Ser Ser Ile Asn Val Ser Val Asn Ala Val Gln Thr Val
210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
            275                 280                 285

Tyr Thr Cys Asn Val Thr Glu Ser Val Asn Asp His Gln Asp Glu Lys
290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
            340                 345                 350

Asp Asn Arg Thr Leu Gly Asp Ser Ser Ala Gly Glu Ile Ala Leu Ser
            355                 360                 365

Thr Arg Asn Val Ser Glu Thr Arg Tyr Val Ser Glu Leu Thr Leu Val
370                 375                 380

Arg Val Lys Val Ala Glu Ala Gly His Tyr Thr Met Arg Ala Phe His
385                 390                 395                 400
```

Glu Asp Ala Glu Val Gln Leu Ser Phe Gln Leu Gln Ile Asn Val Pro
                405                 410                 415
Val Arg Val Leu Glu
            420

<210> SEQ ID NO 9
<211> LENGTH: 771
<212> TYPE: PRT
<213> ORGANISM: Artificial Sequence
<220> FEATURE:
<223> OTHER INFORMATION: Synthetic Construct

<400> SEQUENCE: 9

Met Arg Leu Pro Gly Ala Met Pro Ala Leu Ala Leu Lys Gly Glu Leu
 1               5                  10                  15
Leu Leu Leu Ser Leu Leu Leu Leu Glu Pro Gln Ile Ser Gln Gly
            20                  25                  30
Leu Val Val Thr Pro Pro Gly Pro Glu Leu Val Leu Asn Val Ser Ser
            35                  40                  45
Thr Phe Val Leu Thr Cys Ser Gly Ser Ala Pro Val Val Trp Glu Arg
    50                  55                  60
Met Ser Gln Glu Pro Pro Gln Glu Met Ala Lys Ala Gln Asp Gly Thr
65                  70                  75                  80
Phe Ser Ser Val Leu Thr Leu Thr Asn Leu Thr Gly Leu Asp Thr Gly
                85                  90                  95
Glu Tyr Phe Cys Thr His Asn Asp Ser Arg Gly Leu Glu Thr Asp Glu
            100                 105                 110
Arg Lys Arg Leu Tyr Ile Phe Val Pro Asp Pro Thr Val Gly Phe Leu
        115                 120                 125
Pro Asn Asp Ala Glu Glu Leu Phe Ile Phe Leu Thr Glu Ile Thr Glu
130                 135                 140
Ile Thr Ile Pro Cys Arg Val Thr Asp Pro Gln Leu Val Val Thr Leu
145                 150                 155                 160
His Glu Lys Lys Gly Asp Val Ala Leu Pro Val Pro Tyr Asp His Gln
                165                 170                 175
Arg Gly Phe Phe Gly Ile Phe Glu Asp Arg Ser Tyr Ile Cys Lys Thr
            180                 185                 190
Thr Ile Gly Asp Arg Glu Val Asp Ser Asp Ala Tyr Tyr Val Tyr Arg
        195                 200                 205
Leu Gln Val Ser Ser Ile Asn Val Ser Val Asn Ala Val Gln Thr Val
    210                 215                 220
Val Arg Gln Gly Glu Asn Ile Thr Leu Met Cys Ile Val Ile Gly Asn
225                 230                 235                 240
Glu Val Val Asn Phe Glu Trp Thr Tyr Pro Arg Lys Glu Ser Gly Arg
                245                 250                 255
Leu Val Glu Pro Val Thr Asp Phe Leu Leu Asp Met Pro Tyr His Ile
            260                 265                 270
Arg Ser Ile Leu His Ile Pro Ser Ala Glu Leu Glu Asp Ser Gly Thr
        275                 280                 285
Tyr Thr Cys Asn Val Thr Glu Ser Val Asn Asp His Gln Asp Glu Lys
    290                 295                 300
Ala Ile Asn Ile Thr Val Val Glu Ser Gly Tyr Val Arg Leu Leu Gly
305                 310                 315                 320
Glu Val Gly Thr Leu Gln Phe Ala Glu Leu His Arg Ser Arg Thr Leu
                325                 330                 335

```
Gln Val Val Phe Glu Ala Tyr Pro Pro Thr Val Leu Trp Phe Lys
                340                 345                 350

Asp Asn Arg Thr Leu Gly Asp Ser Ser Ala Gly Glu Ile Ala Leu Ser
            355                 360                 365

Thr Arg Asn Val Ser Glu Thr Arg Tyr Val Ser Glu Leu Thr Leu Val
370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415

Val Arg Val Leu Glu Leu Ser Glu Ser His Pro Asp Ser Gly Glu Gln
            420                 425                 430

Thr Val Arg Cys Arg Gly Arg Gly Met Pro Gln Pro Asn Ile Ile Trp
        435                 440                 445

Ser Ala Cys Arg Asp Leu Lys Arg Cys Pro Arg Glu Leu Pro Pro Thr
    450                 455                 460

Leu Leu Gly Asn Ser Ser Glu Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Val Pro His Ser Leu
        515                 520                 525

Pro Phe Lys Gly Gly Gly Gly Gly Gly Gly Pro Lys Ser Cys
    530                 535                 540

Asp Lys Thr His Thr Cys Pro Pro Cys Pro Ala Pro Glu Leu Leu Gly
545                 550                 555                 560

Gly Pro Ser Val Phe Leu Phe Pro Pro Lys Pro Lys Asp Thr Leu Met
                565                 570                 575

Ile Ser Arg Thr Pro Glu Val Thr Cys Val Val Val Asp Val Ser His
            580                 585                 590

Glu Asp Pro Glu Val Lys Phe Asn Trp Tyr Val Asp Gly Val Glu Val
        595                 600                 605

His Asn Ala Lys Thr Lys Pro Arg Glu Glu Gln Tyr Asn Ser Thr Tyr
    610                 615                 620

Arg Val Val Ser Val Leu Thr Val Leu His Gln Asp Trp Leu Asn Gly
625                 630                 635                 640

Lys Glu Tyr Lys Cys Lys Val Ser Asn Lys Ala Leu Pro Ala Pro Ile
                645                 650                 655

Glu Lys Thr Ile Ser Lys Ala Lys Gly Gln Pro Arg Glu Pro Gln Val
            660                 665                 670

Tyr Thr Leu Pro Pro Ser Arg Asp Glu Leu Thr Lys Asn Gln Val Ser
        675                 680                 685

Leu Thr Cys Leu Val Lys Gly Phe Tyr Pro Ser Asp Ile Ala Val Glu
    690                 695                 700

Trp Glu Ser Asn Gly Gln Pro Glu Asn Asn Tyr Lys Thr Thr Pro Pro
705                 710                 715                 720

Val Leu Asp Ser Asp Gly Ser Phe Phe Leu Tyr Ser Lys Leu Thr Val
                725                 730                 735

Asp Lys Ser Arg Trp Gln Gln Gly Asn Val Phe Ser Cys Ser Val Met
            740                 745                 750
```

His Glu Ala Leu His Asn His Tyr Thr Gln Lys Ser Leu Ser Leu Ser
            755                 760                 765

Pro Gly Lys
    770

<210> SEQ ID NO 10
<211> LENGTH: 555
<212> TYPE: PRT
<213> ORGANISM: Artificial Sequence
<220> FEATURE:
<223> OTHER INFORMATION: Synthetic Construct

<400> SEQUENCE: 10

Met Arg Leu Pro Gly Ala Met Pro Ala Leu Ala Leu Lys Gly Glu Leu
 1               5                  10                  15

Leu Leu Leu Ser Leu Leu Leu Leu Glu Pro Gln Ile Ser Gln Gly
                20                  25                  30

Leu Val Val Thr Pro Pro Gly Pro Glu Leu Val Leu Asn Val Ser Ser
                35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
                100                 105                 110

Arg Lys Arg Leu Tyr Ile Phe Val Pro Asp Pro Thr Val Gly Phe Leu
            115                 120                 125

Pro Asn Asp Ala Glu Glu Leu Phe Ile Phe Leu Thr Glu Ile Thr Glu
    130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Phe Gly Ile Phe Glu Asp Arg Ser Tyr Ile Cys Lys Thr
                180                 185                 190

Thr Ile Gly Asp Arg Glu Val Asp Ser Asp Ala Tyr Tyr Val Tyr Arg
            195                 200                 205

Leu Gln Val Ser Ser Ile Asn Val Ser Val Asn Ala Val Gln Thr Val
    210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
                260                 265                 270

Arg Ser Ile Leu His Ile Pro Ser Ala Glu Leu Glu Asp Ser Gly Thr
            275                 280                 285

Tyr Thr Cys Asn Val Thr Glu Ser Val Asn Asp His Gln Asp Glu Lys
    290                 295                 300

Ala Ile Asn Ile Thr Val Val Glu Ser Gly Tyr Gly Gly Gly Gly
305                 310                 315                 320

Gly Gly Gly Gly Pro Lys Ser Cys Asp Lys Thr His Thr Cys Pro Pro
                325                 330                 335

```
Cys Pro Ala Pro Glu Leu Leu Gly Gly Pro Ser Val Phe Leu Phe Pro
            340                 345                 350

Pro Lys Pro Lys Asp Thr Leu Met Ile Ser Arg Thr Pro Glu Val Thr
        355                 360                 365

Cys Val Val Val Asp Val Ser His Glu Asp Pro Glu Val Lys Phe Asn
    370                 375                 380

Trp Tyr Val Asp Gly Val Glu Val His Asn Ala Lys Thr Lys Pro Arg
385                 390                 395                 400

Glu Glu Gln Tyr Asn Ser Thr Tyr Arg Val Val Ser Val Leu Thr Val
                405                 410                 415

Leu His Gln Asp Trp Leu Asn Gly Lys Glu Tyr Lys Cys Lys Val Ser
            420                 425                 430

Asn Lys Ala Leu Pro Ala Pro Ile Glu Lys Thr Ile Ser Lys Ala Lys
        435                 440                 445

Gly Gln Pro Arg Glu Pro Gln Val Tyr Thr Leu Pro Pro Ser Arg Asp
    450                 455                 460

Glu Leu Thr Lys Asn Gln Val Ser Leu Thr Cys Leu Val Lys Gly Phe
465                 470                 475                 480

Tyr Pro Ser Asp Ile Ala Val Glu Trp Glu Ser Asn Gly Gln Pro Glu
                485                 490                 495

Asn Asn Tyr Lys Thr Thr Pro Pro Val Leu Asp Ser Asp Gly Ser Phe
            500                 505                 510

Phe Leu Tyr Ser Lys Leu Thr Val Asp Lys Ser Arg Trp Gln Gln Gly
        515                 520                 525

Asn Val Phe Ser Cys Ser Val Met His Glu Ala Leu His Asn His Tyr
    530                 535                 540

Thr Gln Lys Ser Leu Ser Leu Ser Pro Gly Lys
545                 550                 555

<210> SEQ ID NO 11
<211> LENGTH: 453
<212> TYPE: PRT
<213> ORGANISM: Artificial Sequence
<220> FEATURE:
<223> OTHER INFORMATION: Synthetic Construct

<400> SEQUENCE: 11

Met Arg Leu Pro Gly Ala Met Pro Ala Leu Ala Leu Lys Gly Glu Leu
  1               5                  10                  15

Leu Leu Leu Ser Leu Leu Leu Leu Glu Pro Gln Ile Ser Gln Gly
                20                  25                  30

Leu Val Val Thr Pro Pro Gly Pro Glu Leu Val Leu Asn Val Ser Ser
            35                  40                  45

Thr Phe Val Leu Thr Cys Ser Gly Ser Ala Pro Val Val Trp Glu Arg
 50                  55                  60

Met Ser Gln Glu Pro Pro Gln Glu Met Ala Lys Ala Gln Asp Gly Thr
 65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
    130                 135                 140
```

```
Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
            165                 170                 175

Arg Gly Phe Phe Gly Ile Phe Glu Asp Arg Ser Tyr Ile Cys Lys Thr
        180                 185                 190

Thr Ile Gly Asp Arg Glu Val Asp Ser Asp Ala Tyr Tyr Val Tyr Arg
    195                 200                 205

Leu Gln Val Ser Ser Gly Gly Gly Gly Gly Gly Gly Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 12
<211> LENGTH: 871
<212> TYPE: PRT
<213> ORGANISM: Artificial Sequence
<220> FEATURE:
<223> OTHER INFORMATION: Synthetic Construct

<400> SEQUENCE: 12

Met Val Ser Tyr Trp Asp Thr Gly Val Leu Leu Cys Ala Leu Leu Ser
1               5                   10                  15

Cys Leu Leu Leu Thr Gly Ser Gly Arg Pro Phe Val Glu Met Tyr Ser
            20                  25                  30

Glu Ile Pro Glu Ile Ile His Met Thr Glu Gly Arg Glu Leu Val Ile
        35                  40                  45
```

```
Pro Cys Arg Val Thr Ser Pro Asn Ile Thr Val Leu Lys Lys Phe
 50                  55                  60

Pro Leu Asp Thr Leu Ile Pro Asp Gly Lys Arg Ile Ile Trp Asp Ser
 65                  70                  75                  80

Arg Lys Gly Phe Ile Ile Ser Asn Ala Thr Tyr Lys Glu Ile Gly Leu
                 85                  90                  95

Leu Thr Cys Glu Ala Thr Val Asn Gly His Leu Tyr Lys Thr Asn Tyr
            100                 105                 110

Leu Thr His Arg Gln Thr Ser Ser Ser Ser Ser Ser Ser Ser Ser Gln
            115                 120                 125

Ile Ser Gln Gly Leu Val Val Thr Pro Pro Gly Pro Glu Leu Val Leu
130                 135                 140

Asn Val Ser Ser Thr Phe Val Leu Thr Cys Ser Gly Ser Ala Pro Val
145                 150                 155                 160

Val Trp Glu Arg Met Ser Gln Glu Pro Pro Gln Glu Met Ala Lys Ala
                165                 170                 175

Gln Asp Gly Thr Phe Ser Ser Val Leu Thr Leu Thr Asn Leu Thr Gly
            180                 185                 190

Leu Asp Thr Gly Glu Tyr Phe Cys Thr His Asn Asp Ser Arg Gly Leu
            195                 200                 205

Glu Thr Asp Glu Arg Lys Arg Leu Tyr Ile Phe Val Pro Asp Pro Thr
210                 215                 220

Val Gly Phe Leu Pro Asn Asp Ala Glu Glu Leu Phe Ile Phe Leu Thr
225                 230                 235                 240

Glu Ile Thr Glu Ile Thr Ile Pro Cys Arg Val Thr Asp Pro Gln Leu
                245                 250                 255

Val Val Thr Leu His Glu Lys Lys Gly Asp Val Ala Leu Pro Val Pro
            260                 265                 270

Tyr Asp His Gln Arg Gly Phe Phe Gly Ile Phe Glu Asp Arg Ser Tyr
            275                 280                 285

Ile Cys Lys Thr Thr Ile Gly Asp Arg Glu Val Asp Ser Asp Ala Tyr
290                 295                 300

Tyr Val Tyr Arg Leu Gln Val Ser Ser Ile Asn Val Ser Val Asn Ala
305                 310                 315                 320

Val Gln Thr Val Val Arg Gln Gly Glu Asn Ile Thr Leu Met Cys Ile
                325                 330                 335

Val Ile Gly Asn Glu Val Val Asn Phe Glu Trp Thr Tyr Pro Arg Lys
            340                 345                 350

Glu Ser Gly Arg Leu Val Glu Pro Val Thr Asp Phe Leu Leu Asp Met
            355                 360                 365

Pro Tyr His Ile Arg Ser Ile Leu His Ile Pro Ser Ala Glu Leu Glu
            370                 375                 380

Asp Ser Gly Thr Tyr Thr Cys Asn Val Thr Glu Ser Val Asn Asp His
385                 390                 395                 400

Gln Asp Glu Lys Ala Ile Asn Ile Thr Val Val Glu Ser Gly Tyr Val
                405                 410                 415

Arg Leu Leu Gly Glu Val Gly Thr Leu Gln Phe Ala Glu Leu His Arg
            420                 425                 430

Ser Arg Thr Leu Gln Val Val Phe Glu Ala Tyr Pro Pro Pro Thr Val
            435                 440                 445

Leu Trp Phe Lys Asp Asn Arg Thr Leu Gly Asp Ser Ser Ala Gly Glu
450                 455                 460
```

-continued

```
Ile Ala Leu Ser Thr Arg Asn Val Ser Glu Thr Arg Tyr Val Ser Glu
465                 470                 475                 480

Leu Thr Leu Val Arg Val Lys Val Ala Glu Ala Gly His Tyr Thr Met
                485                 490                 495

Arg Ala Phe His Glu Asp Ala Glu Val Gln Leu Ser Phe Gln Leu Gln
                500                 505                 510

Ile Asn Val Pro Val Arg Val Leu Glu Leu Ser Glu Ser His Pro Asp
                515                 520                 525

Ser Gly Glu Gln Thr Val Arg Cys Arg Gly Arg Gly Met Pro Gln Pro
            530                 535                 540

Asn Ile Ile Trp Ser Ala Cys Arg Asp Leu Lys Arg Cys Pro Arg Glu
545                 550                 555                 560

Leu Pro Pro Thr Leu Leu Gly Asn Ser Ser Glu Glu Ser Gln Leu
                565                 570                 575

Glu Thr Asn Val Thr Tyr Trp Glu Glu Gln Glu Phe Glu Val Val
                580                 585                 590

Ser Thr Leu Arg Leu Gln His Val Asp Arg Pro Leu Ser Val Arg Cys
                595                 600                 605

Thr Leu Arg Asn Ala Val Gly Gln Asp Thr Gln Glu Val Ile Val Val
                610                 615                 620

Pro His Ser Leu Pro Phe Thr Gly Gly Gly Gly Gly Gly Gly Gly Gly
625                 630                 635                 640

Pro Lys Ser Cys Asp Lys Thr His Thr Cys Pro Pro Cys Pro Ala Pro
                645                 650                 655

Glu Leu Leu Gly Gly Pro Ser Val Phe Leu Phe Pro Pro Lys Pro Lys
                660                 665                 670

Asp Thr Leu Met Ile Ser Arg Thr Pro Glu Val Thr Cys Val Val Val
                675                 680                 685

Asp Val Ser His Glu Asp Pro Glu Val Lys Phe Asn Trp Tyr Val Asp
                690                 695                 700

Gly Val Glu Val His Asn Ala Lys Thr Lys Pro Arg Glu Glu Gln Tyr
705                 710                 715                 720

Asn Ser Thr Tyr Arg Val Val Ser Val Leu Thr Val Leu His Gln Asp
                725                 730                 735

Trp Leu Asn Gly Lys Glu Tyr Lys Cys Lys Val Ser Asn Lys Ala Leu
                740                 745                 750

Pro Ala Pro Ile Glu Lys Thr Ile Ser Lys Ala Lys Gly Gln Pro Arg
                755                 760                 765

Glu Pro Gln Val Tyr Thr Leu Pro Pro Ser Arg Asp Glu Leu Thr Lys
                770                 775                 780

Asn Gln Val Ser Leu Thr Cys Leu Val Lys Gly Phe Tyr Pro Ser Asp
785                 790                 795                 800

Ile Ala Val Glu Trp Glu Ser Asn Gly Gln Pro Glu Asn Asn Tyr Lys
                805                 810                 815

Thr Thr Pro Pro Val Leu Asp Ser Asp Gly Ser Phe Phe Leu Tyr Ser
                820                 825                 830

Lys Leu Thr Val Asp Lys Ser Arg Trp Gln Gln Gly Asn Val Phe Ser
                835                 840                 845

Cys Ser Val Met His Glu Ala Leu His Asn His Tyr Thr Gln Lys Ser
                850                 855                 860

Leu Ser Leu Ser Pro Gly Lys
865                 870
```

```
<210> SEQ ID NO 13
<211> LENGTH: 873
<212> TYPE: PRT
<213> ORGANISM: Artificial Sequence
<220> FEATURE:
<223> OTHER INFORMATION: Synthetic Construct

<400> SEQUENCE: 13

Met Arg Leu Pro Gly Ala Met Pro Ala Leu Ala Leu Lys Gly Glu Leu
1               5                   10                  15

Leu Leu Leu Ser Leu Leu Leu Leu Glu Pro Gln Ile Ser Gln Gly
            20                  25                  30

Leu Val Val Thr Pro Pro Gly Pro Glu Leu Val Leu Asn Val Ser Ser
            35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
    130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Phe Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
        195                 200                 205

Leu Gln Val Ser Ser Ile Asn Val Ser Val Asn Ala Val Gln Thr Val
    210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
        275                 280                 285

Tyr Thr Cys Asn Val Thr Glu Ser Val Asn Asp His Gln Asp Glu Lys
    290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
            340                 345                 350

Asp Asn Arg Thr Leu Gly Asp Ser Ser Ala Gly Glu Ile Ala Leu Ser
        355                 360                 365
```

-continued

```
Thr Arg Asn Val Ser Glu Thr Arg Tyr Val Ser Glu Leu Thr Leu Val
    370                 375                 380
Arg Val Lys Val Ala Glu Ala Gly His Tyr Thr Met Arg Ala Phe His
385                 390                 395                 400
Glu Asp Ala Glu Val Gln Leu Ser Phe Gln Leu Gln Ile Asn Val Pro
                405                 410                 415
Val Arg Val Leu Glu Leu Ser Glu Ser His Pro Asp Ser Gly Glu Gln
            420                 425                 430
Thr Val Arg Cys Arg Gly Arg Gly Met Pro Gln Pro Asn Ile Ile Trp
        435                 440                 445
Ser Ala Cys Arg Asp Leu Lys Arg Cys Pro Arg Glu Leu Pro Pro Thr
450                 455                 460
Leu Leu Gly Asn Ser Ser Glu Glu Ser Gln Leu Glu Thr Asn Val
465                 470                 475                 480
Thr Tyr Trp Glu Glu Gln Glu Phe Glu Val Val Ser Thr Leu Arg
                485                 490                 495
Leu Gln His Val Asp Arg Pro Leu Ser Val Arg Cys Thr Leu Arg Asn
            500                 505                 510
Ala Val Gly Gln Asp Thr Gln Glu Val Ile Val Val Pro His Ser Leu
        515                 520                 525
Pro Phe Ser Ser Ser Ser Ser Ser Ser Arg Pro Phe Val Glu
530                 535                 540
Met Tyr Ser Glu Ile Pro Glu Ile Ile His Met Thr Glu Gly Arg Glu
545                 550                 555                 560
Leu Val Ile Pro Cys Arg Val Thr Ser Pro Asn Ile Thr Val Thr Leu
                565                 570                 575
Lys Lys Phe Pro Leu Asp Thr Leu Ile Pro Asp Gly Lys Arg Ile Ile
            580                 585                 590
Trp Asp Ser Arg Lys Gly Phe Ile Ile Ser Asn Ala Thr Tyr Lys Glu
        595                 600                 605
Ile Gly Leu Leu Thr Cys Glu Ala Thr Val Asn Gly His Leu Tyr Lys
610                 615                 620
Thr Asn Tyr Leu Thr His Arg Gln Thr Gly Gly Gly Gly Gly Gly
625                 630                 635                 640
Gly Gly Pro Lys Ser Cys Asp Lys Thr His Thr Cys Pro Pro Cys Pro
                645                 650                 655
Ala Pro Glu Leu Leu Gly Gly Pro Ser Val Phe Leu Phe Pro Pro Lys
            660                 665                 670
Pro Lys Asp Thr Leu Met Ile Ser Arg Thr Pro Glu Val Thr Cys Val
        675                 680                 685
Val Val Asp Val Ser His Glu Asp Pro Glu Val Lys Phe Asn Trp Tyr
690                 695                 700
Val Asp Gly Val Glu Val His Asn Ala Lys Thr Lys Pro Arg Glu Glu
705                 710                 715                 720
Gln Tyr Asn Ser Thr Tyr Arg Val Val Ser Val Leu Thr Val Leu His
                725                 730                 735
Gln Asp Trp Leu Asn Gly Lys Glu Tyr Lys Cys Lys Val Ser Asn Lys
            740                 745                 750
Ala Leu Pro Ala Pro Ile Glu Lys Thr Ile Ser Lys Ala Lys Gly Gln
        755                 760                 765
Pro Arg Glu Pro Gln Val Tyr Thr Leu Pro Pro Ser Arg Asp Glu Leu
770                 775                 780
```

```
Thr Lys Asn Gln Val Ser Leu Thr Cys Leu Val Lys Gly Phe Tyr Pro
785                 790                 795                 800

Ser Asp Ile Ala Val Glu Trp Glu Ser Asn Gly Gln Pro Glu Asn Asn
                805                 810                 815

Tyr Lys Thr Thr Pro Pro Val Leu Asp Ser Asp Gly Ser Phe Phe Leu
            820                 825                 830

Tyr Ser Lys Leu Thr Val Asp Lys Ser Arg Trp Gln Gln Gly Asn Val
            835                 840                 845

Phe Ser Cys Ser Val Met His Glu Ala Leu His Asn His Tyr Thr Gln
        850                 855                 860

Lys Ser Leu Ser Leu Ser Pro Gly Lys
865                 870

<210> SEQ ID NO 14
<211> LENGTH: 656
<212> TYPE: PRT
<213> ORGANISM: Artificial Sequence
<220> FEATURE:
<223> OTHER INFORMATION: Synthetic Construct

<400> SEQUENCE: 14

Met Val Ser Tyr Trp Asp Thr Gly Val Leu Leu Cys Ala Leu Leu Ser
1               5                   10                  15

Cys Leu Leu Leu Thr Gly Ser Gly Arg Pro Phe Val Glu Met Tyr Ser
                20                  25                  30

Glu Ile Pro Glu Ile Ile His Met Thr Glu Gly Arg Glu Leu Val Ile
            35                  40                  45

Pro Cys Arg Val Thr Ser Pro Asn Ile Thr Val Thr Leu Lys Lys Phe
50                  55                  60

Pro Leu Asp Thr Leu Ile Pro Asp Gly Lys Arg Ile Ile Trp Asp Ser
65                  70                  75                  80

Arg Lys Gly Phe Ile Ile Ser Asn Ala Thr Tyr Lys Glu Ile Gly Leu
                85                  90                  95

Leu Thr Cys Glu Ala Thr Val Asn Gly His Leu Tyr Lys Thr Asn Tyr
            100                 105                 110

Leu Thr His Arg Gln Thr Ser Ser Ser Ser Ser Ser Ser Ser Ser Gln
        115                 120                 125

Ile Ser Gln Gly Leu Val Val Thr Pro Pro Gly Pro Glu Leu Val Leu
130                 135                 140

Asn Val Ser Ser Thr Phe Val Leu Thr Cys Ser Gly Ser Ala Pro Val
145                 150                 155                 160

Val Trp Glu Arg Met Ser Gln Glu Pro Pro Gln Glu Met Ala Lys Ala
                165                 170                 175

Gln Asp Gly Thr Phe Ser Ser Val Leu Thr Leu Thr Asn Leu Thr Gly
            180                 185                 190

Leu Asp Thr Gly Glu Tyr Phe Cys Thr His Asn Asp Ser Arg Gly Leu
        195                 200                 205

Glu Thr Asp Glu Arg Lys Arg Leu Tyr Ile Phe Val Pro Asp Pro Thr
210                 215                 220

Val Gly Phe Leu Pro Asn Asp Ala Glu Glu Leu Phe Ile Phe Leu Thr
225                 230                 235                 240

Glu Ile Thr Glu Ile Thr Ile Pro Cys Arg Val Thr Asp Pro Gln Leu
                245                 250                 255

Val Val Thr Leu His Glu Lys Lys Gly Asp Val Ala Leu Pro Val Pro
            260                 265                 270
```

-continued

```
Tyr Asp His Gln Arg Gly Phe Phe Gly Ile Phe Glu Asp Arg Ser Tyr
            275                 280                 285
Ile Cys Lys Thr Thr Ile Gly Asp Arg Glu Val Asp Ser Asp Ala Tyr
290                 295                 300
Tyr Val Tyr Arg Leu Gln Val Ser Ser Ile Asn Val Ser Val Asn Ala
305                 310                 315                 320
Val Gln Thr Val Val Arg Gln Gly Glu Asn Ile Thr Leu Met Cys Ile
            325                 330                 335
Val Ile Gly Asn Glu Val Val Asn Phe Glu Trp Thr Tyr Pro Arg Lys
            340                 345                 350
Glu Ser Gly Arg Leu Val Glu Pro Val Thr Asp Phe Leu Leu Asp Met
            355                 360                 365
Pro Tyr His Ile Arg Ser Ile Leu His Ile Pro Ser Ala Glu Leu Glu
            370                 375                 380
Asp Ser Gly Thr Tyr Thr Cys Asn Val Thr Glu Ser Val Asn Asp His
385                 390                 395                 400
Gln Asp Glu Lys Ala Ile Asn Ile Thr Val Val Glu Ser Gly Tyr Thr
                405                 410                 415
Gly Gly Gly Gly Gly Gly Gly Gly Pro Lys Ser Cys Asp Lys Thr
            420                 425                 430
His Thr Cys Pro Pro Cys Pro Ala Pro Glu Leu Leu Gly Gly Pro Ser
            435                 440                 445
Val Phe Leu Phe Pro Pro Lys Pro Lys Asp Thr Leu Met Ile Ser Arg
450                 455                 460
Thr Pro Glu Val Thr Cys Val Val Val Asp Val Ser His Glu Asp Pro
465                 470                 475                 480
Glu Val Lys Phe Asn Trp Tyr Val Asp Gly Val Glu Val His Asn Ala
                485                 490                 495
Lys Thr Lys Pro Arg Glu Glu Gln Tyr Asn Ser Thr Tyr Arg Val Val
            500                 505                 510
Ser Val Leu Thr Val Leu His Gln Asp Trp Leu Asn Gly Lys Glu Tyr
            515                 520                 525
Lys Cys Lys Val Ser Asn Lys Ala Leu Pro Ala Pro Ile Glu Lys Thr
530                 535                 540
Ile Ser Lys Ala Lys Gly Gln Pro Arg Glu Pro Gln Val Tyr Thr Leu
545                 550                 555                 560
Pro Pro Ser Arg Asp Glu Leu Thr Lys Asn Gln Val Ser Leu Thr Cys
                565                 570                 575
Leu Val Lys Gly Phe Tyr Pro Ser Asp Ile Ala Val Glu Trp Glu Ser
            580                 585                 590
Asn Gly Gln Pro Glu Asn Asn Tyr Lys Thr Thr Pro Pro Val Leu Asp
            595                 600                 605
Ser Asp Gly Ser Phe Phe Leu Tyr Ser Lys Leu Thr Val Asp Lys Ser
610                 615                 620
Arg Trp Gln Gln Gly Asn Val Phe Ser Cys Ser Val Met His Glu Ala
625                 630                 635                 640
Leu His Asn His Tyr Thr Gln Lys Ser Leu Ser Leu Ser Pro Gly Lys
                645                 650                 655

<210> SEQ ID NO 15
<211> LENGTH: 658
<212> TYPE: PRT
<213> ORGANISM: Artificial Sequence
<220> FEATURE:
<223> OTHER INFORMATION: Synthetic Construct
```

<400> SEQUENCE: 15

```
Met Arg Leu Pro Gly Ala Met Pro Ala Leu Ala Leu Lys Gly Glu Leu
  1               5                  10                  15
Leu Leu Leu Ser Leu Leu Leu Leu Glu Pro Gln Ile Ser Gln Gly
             20                  25                  30
Leu Val Val Thr Pro Pro Gly Pro Glu Leu Val Leu Asn Val Ser Ser
             35                  40                  45
Thr Phe Val Leu Thr Cys Ser Gly Ser Ala Pro Val Val Trp Glu Arg
 50                  55                  60
Met Ser Gln Glu Pro Pro Gln Glu Met Ala Lys Ala Gln Asp Gly Thr
 65                  70                  75                  80
Phe Ser Ser Val Leu Thr Leu Thr Asn Leu Thr Gly Leu Asp Thr Gly
                 85                  90                  95
Glu Tyr Phe Cys Thr His Asn Asp Ser Arg Gly Leu Glu Thr Asp Glu
                100                 105                 110
Arg Lys Arg Leu Tyr Ile Phe Val Pro Asp Pro Thr Val Gly Phe Leu
                115                 120                 125
Pro Asn Asp Ala Glu Glu Leu Phe Ile Phe Leu Thr Glu Ile Thr Glu
    130                 135                 140
Ile Thr Ile Pro Cys Arg Val Thr Asp Pro Gln Leu Val Val Thr Leu
145                 150                 155                 160
His Glu Lys Lys Gly Asp Val Ala Leu Pro Val Pro Tyr Asp His Gln
                165                 170                 175
Arg Gly Phe Phe Gly Ile Phe Glu Asp Arg Ser Tyr Ile Cys Lys Thr
                180                 185                 190
Thr Ile Gly Asp Arg Glu Val Asp Ser Asp Ala Tyr Tyr Val Tyr Arg
            195                 200                 205
Leu Gln Val Ser Ser Ile Asn Val Ser Val Asn Ala Val Gln Thr Val
    210                 215                 220
Val Arg Gln Gly Glu Asn Ile Thr Leu Met Cys Ile Val Ile Gly Asn
225                 230                 235                 240
Glu Val Val Asn Phe Glu Trp Thr Tyr Pro Arg Lys Glu Ser Gly Arg
                245                 250                 255
Leu Val Glu Pro Val Thr Asp Phe Leu Leu Asp Met Pro Tyr His Ile
                260                 265                 270
Arg Ser Ile Leu His Ile Pro Ser Ala Glu Leu Glu Asp Ser Gly Thr
            275                 280                 285
Tyr Thr Cys Asn Val Thr Glu Ser Val Asn Asp His Gln Asp Glu Lys
    290                 295                 300
Ala Ile Asn Ile Thr Val Val Glu Ser Gly Tyr Ser Ser Ser Ser Ser
305                 310                 315                 320
Ser Ser Ser Ser Arg Pro Phe Val Glu Met Tyr Ser Glu Ile Pro Glu
                325                 330                 335
Ile Ile His Met Thr Glu Gly Arg Glu Leu Val Ile Pro Cys Arg Val
            340                 345                 350
Thr Ser Pro Asn Ile Thr Val Thr Leu Lys Lys Phe Pro Leu Asp Thr
    355                 360                 365
Leu Ile Pro Asp Gly Lys Arg Ile Ile Trp Asp Ser Arg Lys Gly Phe
370                 375                 380
Ile Ile Ser Asn Ala Thr Tyr Lys Glu Ile Gly Leu Leu Thr Cys Glu
                385                 390                 395                 400
Ala Thr Val Asn Gly His Leu Tyr Lys Thr Asn Tyr Leu Thr His Arg
                405                 410                 415
```

```
Gln Thr Gly Gly Gly Gly Gly Gly Gly Pro Lys Ser Cys Asp
            420                 425                 430

Lys Thr His Thr Cys Pro Pro Cys Pro Ala Pro Glu Leu Leu Gly Gly
            435                 440                 445

Pro Ser Val Phe Leu Phe Pro Pro Lys Pro Lys Asp Thr Leu Met Ile
    450                 455                 460

Ser Arg Thr Pro Glu Val Thr Cys Val Val Val Asp Val Ser His Glu
465                 470                 475                 480

Asp Pro Glu Val Lys Phe Asn Trp Tyr Val Asp Gly Val Glu Val His
                485                 490                 495

Asn Ala Lys Thr Lys Pro Arg Glu Glu Gln Tyr Asn Ser Thr Tyr Arg
            500                 505                 510

Val Val Ser Val Leu Thr Val Leu His Gln Asp Trp Leu Asn Gly Lys
        515                 520                 525

Glu Tyr Lys Cys Lys Val Ser Asn Lys Ala Leu Pro Ala Pro Ile Glu
    530                 535                 540

Lys Thr Ile Ser Lys Ala Lys Gly Gln Pro Arg Glu Pro Gln Val Tyr
545                 550                 555                 560

Thr Leu Pro Pro Ser Arg Asp Glu Leu Thr Lys Asn Gln Val Ser Leu
                565                 570                 575

Thr Cys Leu Val Lys Gly Phe Tyr Pro Ser Asp Ile Ala Val Glu Trp
            580                 585                 590

Glu Ser Asn Gly Gln Pro Glu Asn Asn Tyr Lys Thr Thr Pro Pro Val
        595                 600                 605

Leu Asp Ser Asp Gly Ser Phe Phe Leu Tyr Ser Lys Leu Thr Val Asp
    610                 615                 620

Lys Ser Arg Trp Gln Gln Gly Asn Val Phe Ser Cys Ser Val Met His
625                 630                 635                 640

Glu Ala Leu His Asn His Tyr Thr Gln Lys Ser Leu Ser Leu Ser Pro
                645                 650                 655

Gly Lys

<210> SEQ ID NO 16
<211> LENGTH: 1593
<212> TYPE: DNA
<213> ORGANISM: Homo sapiens

<400> SEQUENCE: 16
atgcggcttc cgggtgcgat gccagctctg gccctcaaag gcgagctgct gttgctgtct      60
ctcctgttac ttctggaacc acagatctct cagggcctgg tcgtcacacc cccggggcca     120
gagcttgtcc tcaatgtctc cagcaccttc gttctgacct gctcgggttc agctccggtg     180
gtgtgggaac ggatgtccca ggagccccca caggaaatgg ccaaggccca ggatggcacc     240
ttctccagcg tgctcacact gaccaacctc actgggctag acacgggaga atacttttgc     300
acccacaatg actcccgtgg actggagacc gatgagcgga acggctcta catctttgtg      360 ccagatccca ccgtgggctt cctccctaat gatgccgagg aactattcat ctttctcacg     420
gaaataactg agatcaccat tccatgccga gtaacagacc cacagctggt ggtgacactg     480
cacgagaaga aggggacgt tgcactgcct gtcccctatg atcaccaacg tggctttttt       540
ggtatctttg aggacagaag ctacatctgc aaaaccacca ttggggacag ggaggtggat     600
tctgatgcct actatgtcta cagactccag gtgtcatcca tcaacgtctc tgtgaacgca     660
gtgcagactg tggtccgcca gggtgagaac atcaccctca tgtgcattgt gatcgggaat     720
```

```
gaggtggtca acttcgagtg gacatacccc cgcaaagaaa gtgggcggct ggtggagccg      780
gtgactgact tcctcttgga tatgccttac cacatccgct ccatcctgca catccccagt      840
gccgagttag aagactcggg gacctacacc tgcaatgtga cggagagtgt gaatgaccat      900
caggatgaaa aggccatcaa catcaccgtg gttgagagcg ctacgtgcg gctcctggga       960 gaggtgggca cactacaatt tgctgagctg catcggagcc ggacactgca ggtagtgttc     1020
gaggcctacc caccgcccac tgtcctgtgg ttcaaagaca accgcaccct gggcgactcc     1080
agcgctggcg aaatcgccct gtccacgcgc aacgtgtcgg agacccggta tgtgtcagag     1140
ctgacactgg ttcgcgtgaa ggtggcagag gctggccact acaccatgcg ggccttccat     1200
gaggatgctg aggtccagct ctccttccag ctacagatca atgtccctgt ccgagtgctg     1260
gagctaagtg agagccaccc tgacagtggg aacagacag tccgctgtcg tggccggggc      1320
atgccccagc cgaacatcat ctggtctgcc tgcagagacc tcaaaaggtg tccacgtgag     1380
ctgccgccca cgctgctggg aacagttcc aagaggaga gccagctgga gactaacgtg      1440
acgtactggg aggaggagca ggagtttgag gtggtgagca cactgcgtct gcagcacgtg     1500
gatcggccac tgtcggtgcg ctgcacgctg cgcaacgctg tgggccagga cacgcaggag     1560
gtcatcgtgg tgccacactc cttgcccttt taa                                  1593

<210> SEQ ID NO 17
<211> LENGTH: 1266
<212> TYPE: DNA
<213> ORGANISM: Homo sapiens

<400> SEQUENCE: 17
atgcggcttc cgggtgcgat gccagctctg gccctcaaag gcgagctgct gttgctgtct       60
ctcctgttac ttctggaacc acagatctct cagggcctgg tcgtcacacc cccggggcca      120
gagcttgtcc tcaatgtctc cagcaccttc gttctgacct gctcgggttc agctccggtg      180
gtgtgggaac ggatgtccca ggagccccca caggaaatgg ccaaggccca ggatggcacc      240
ttctccagcg tgctcacact gaccaacctc actgggctag acacgggaga atacttttgc      300
acccacaatg actcccgtgg actggagacc gatgagcgga acggctcta catctttgtg       360 ccagatccca ccgtgggctt cctccctaat gatgccgagg aactattcat ctttctcacg      420
gaaataactg agatcaccat tccatgccga gtaacagacc acagctggt ggtgacactg       480 cacgagaaga aggggacgt tgcactgcct gtccccctatg atcaccaacg tggctttttt     540
ggtatctttg aggacagaag ctacatctgc aaaaccacca ttggggacag ggaggtggat      600
tctgatgcct actatgtcta cagactccag gtgtcatcca tcaacgtctc tgtgaacgca      660
gtgcagactg tggtccgcca gggtgagaac atcaccctca tgtgcattgt gatcgggaat      720
gaggtggtca acttcgagtg gacatacccc cgcaaagaaa gtgggcggct ggtggagccg      780
gtgactgact tcctcttgga tatgccttac cacatccgct ccatcctgca catccccagt      840
gccgagttag aagactcggg gacctacacc tgcaatgtga cggagagtgt gaatgaccat      900
caggatgaaa aggccatcaa catcaccgtg gttgagagcg ctacgtgcg gctcctggga       960 gaggtgggca cactacaatt tgctgagctg catcggagcc ggacactgca ggtagtgttc     1020
gaggcctacc caccgcccac tgtcctgtgg ttcaaagaca accgcaccct gggcgactcc     1080
agcgctggcg aaatcgccct gtccacgcgc aacgtgtcgg agacccggta tgtgtcagag     1140
ctgacactgg ttcgcgtgaa ggtggcagag gctggccact acaccatgcg ggccttccat     1200
```

| | |
|---|---|
| gaggatgctg aggtccagct ctccttccag ctacagatca atgtccctgt ccgagtgctg | 1260 |
| gagtag | 1266 |

<210> SEQ ID NO 18
<211> LENGTH: 2316
<212> TYPE: DNA
<213> ORGANISM: Artificial Sequence
<220> FEATURE:
<223> OTHER INFORMATION: Synthetic Construct

<400> SEQUENCE: 18

| | |
|---|---|
| atgcggcttc cgggtgcgat gccagctctg gccctcaaag gcgagctgct gttgctgtct | 60 |
| ctcctgttac ttctggaacc acagatctct cagggcctgg tcgtcacacc cccggggcca | 120 |
| gagcttgtcc tcaatgtctc cagcaccttc gttctgacct gctcgggttc agctccggtg | 180 |
| gtgtgggaac ggatgtccca ggagccccca caggaaatgg ccaaggccca ggatggcacc | 240 |
| ttctccagcg tgctcacact gaccaacctc actgggctag acacgggaga atacttttgc | 300 |
| acccacaatg actcccgtgg actggagacc gatgagcgga acggctcta catctttgtg | 360 |
| ccagatccca ccgtgggctt cctccctaat gatgccgagg aactattcat ctttctcacg | 420 |
| gaaataactg agatcaccat tccatgccga gtaacagacc cacagctggt ggtgacactg | 480 |
| cacgagaaga agggggacgt tgcactgcct gtcccctatg atcaccaacg tggcttttt | 540 |
| ggtatctttg aggacagaag ctacatctgc aaaaccacca ttggggacag ggaggtggat | 600 |
| tctgatgcct actatgtcta cagactccag gtgtcatcca tcaacgtctc tgtgaacgca | 660 |
| gtgcagactg tggtccgcca gggtgagaac atcaccctca tgtgcattgt gatcgggaat | 720 |
| gaggtggtca cttcgagtg gacataccc cgcaaagaaa gtgggcggct ggtggagccg | 780 |
| gtgactgact tcctcttgga tatgccttac cacatccgct ccatcctgca catccccagt | 840 |
| gccgagttag aagactcggg gacctacacc tgcaatgtga cggagagtgt gaatgaccat | 900 |
| caggatgaaa aggccatcaa catcaccgtg gttgagagcg gctacgtgcg ctcctgggga | 960 |
| gaggtgggca cactacaatt tgctgagctg catcggagcc ggacactgca ggtagtgttc | 1020 |
| gaggcctacc caccgcccac tgtcctgtgg ttcaaagaca accgcaccct gggcgactcc | 1080 |
| agcgctggcg aaatcgccct gtccacgcgc aacgtgtcgg agacccggta tgtgtcagag | 1140 |
| ctgacactgg ttcgcgtgaa ggtggcagag gctggccact acaccatgcg ggccttccat | 1200 |
| gaggatgctg aggtccagct ctccttccag ctacagatca atgtccctgt ccgagtgctg | 1260 |
| gagctaagtg agagccaccc tgacagtggg aacagacaca tccgctgtcg tggccggggc | 1320 |
| atgcccagc cgaacatcat ctggtctgcc tgcagagacc tcaaaaggtg tccacgtgag | 1380 |
| ctgccgccca cgctgctggg aacagttcc gaagaggaga gccagctgga gactaacgtg | 1440 |
| acgtactggg aggaggagca ggagtttgag gtggtgagca cactgcgtct gcagcacgtg | 1500 |
| gatcggccac tgtcggtgcg ctgcacgctg cgcaacgctg tgggccagga cacgcaggag | 1560 |
| gtcatcgtgg tgccacactc cttgcccttt accggtggag gtggaggtgg aggtggaggt | 1620 |
| cctaaatctt gtgacaaaac tcacacatgc ccaccgtgcc cagcacctga actcctgggg | 1680 |
| ggaccgtcag tcttcctctt ccccccaaaa cccaaggaca cctcatgat ctcccggacc | 1740 |
| cctgaggtca catgcgtggt ggtggacgtg agccacgaag accctgaggt caagttcaac | 1800 |
| tggtacgtgg acggcgtgga ggtgcataat gccaagacaa agccgcggga ggagcagtac | 1860 |
| aacagcacgt accgtgtggt cagcgtcctc accgtcctgc accaggactg gctgaatggc | 1920 |
| aaggagtaca agtgcaaggt ctccaacaaa gccctcccag cccccatcga gaaaaccatc | 1980 |

| | |
|---|---|
| tccaaagcca aagggcagcc ccgagaacca caggtgtaca ccctgccccc atcccgggat | 2040 |
| gagctgacca agaaccaggt cagcctgacc tgcctggtca aaggcttcta tcccagcgac | 2100 |
| atcgccgtgg agtgggagag caatgggcag ccggagaaca actacaagac cacgcctccc | 2160 |
| gtgctggact ccgacggctc cttcttcctc tacagcaagc tcaccgtgga caagagcagg | 2220 |
| tggcagcagg ggaacgtctt ctcatgctcc gtgatgcatg aggctctgca caaccactac | 2280 |
| acgcagaaga gcctctccct gtctccgggt aaatag | 2316 |

```
<210> SEQ ID NO 19
<211> LENGTH: 1671
<212> TYPE: DNA
<213> ORGANISM: Artificial Sequence
<220> FEATURE:
<223> OTHER INFORMATION: Synthetic Construct

<400> SEQUENCE: 19
```

| | |
|---|---|
| atgcggcttc cgggtgcgat gccagctctg ccctcaaag gcgagctgct gttgctgtct | 60 |
| ctcctgttac ttctggaacc acagatctct cagggcctgg tcgtcacacc cccggggcca | 120 |
| gagcttgtcc tcaatgtctc cagcaccttg gttctgacct gctcgggttc agctccggtg | 180 |
| gtgtgggaac ggatgtccca ggagccccca caggaaatgg ccaaggccca ggatggcacc | 240 |
| ttctccagcg tgctcacact gaccaacctc actgggctag acacgggaga atacttttgc | 300 |
| acccacaatg actcccgtgg actggagacc gatgagcgga acggctcta catctttgtg | 360 |
| ccagatccca ccgtgggctt cctccctaat gatgccgagg aactattcat ctttctcacg | 420 |
| gaaataactg agatcaccat tccatgccga gtaacagacc cacagctggt ggtgacactg | 480 |
| cacgagaaga aggggacgt tgcactgcct gtccccctatg atcaccaacg tggctttttt | 540 |
| ggtatctttg aggacagaag ctacatctgc aaaaccacca ttggggacag ggaggtggat | 600 |
| tctgatgcct actatgtcta cagactccag gtgtcatcca tcaacgtctc tgtgaacgca | 660 |
| gtgcagactg tggtccgcca gggtgagaac atcaccctca tgtgcattgt gatcgggaat | 720 |
| gaggtggtca acttcgagtg gacatacccc cgcaaagaaa gtgggcggct ggtggagccg | 780 |
| gtgactgact cctcttgga tatgccttac cacatccgct ccatcctgca catccccagt | 840 |
| gccgagttag aagactcggg gacctacacc tgcaatgtga cggagagtgt gaatgaccat | 900 |
| caggatgaaa aggccatcaa catcaccgtg gttgagagcg gctacaccgg tggaggtgga | 960 |
| ggtggaggtg gaggtcctaa atcttgtgac aaaactcaca catgcccacc gtgcccagca | 1020 |
| cctgaactcc tggggggacc gtcagtcttc ctcttccccc caaaacccaa ggacaccctc | 1080 |
| atgatctccc ggacccctga ggtcacatgc gtggtggtgg acgtgagcca cgaagaccct | 1140 |
| gaggtcaagt tcaactggta cgtggacggc gtggaggtgc ataatgccaa gacaaagccg | 1200 |
| cgggaggagc agtacaacag cacgtaccgt gtggtcagcg tcctcaccgt cctgcaccag | 1260 |
| gactggctga atggcaagga gtacaagtgc aaggtctcca acaaagccct cccagccccc | 1320 |
| atcgagaaaa ccatctccaa agccaaaggg cagccccgag aaccacaggt gtacaccctg | 1380 |
| cccccatccc gggatgagct gaccaagaac caggtcagcc tgacctgcct ggtcaaaggc | 1440 |
| ttctatccca gcgacatcgc cgtggagtgg gagagcaatg ggcagccgga gaacaactac | 1500 |
| aagaccacgc ctcccgtgct ggactccgac ggctccttct cctctacag caagctcacc | 1560 |
| gtggacaaga gcaggtggca gcaggggaac gtcttctcat gctccgtgat gcatgaggct | 1620 |
| ctgcacaacc actacacgca gaagagcctc tccctgtctc cgggtaaata g | 1671 |

<210> SEQ ID NO 20
<211> LENGTH: 1365
<212> TYPE: DNA
<213> ORGANISM: Artificial Sequence
<220> FEATURE:
<223> OTHER INFORMATION: Synthetic Construct

<400> SEQUENCE: 20

| | |
|---|---|
| atgcggcttc cgggtgcgat gccagctctg gccctcaaag gcgagctgct gttgctgtct | 60 |
| ctcctgttac ttctggaacc acagatctct cagggcctgg tcgtcacacc cccggggcca | 120 |
| gagcttgtcc tcaatgtctc cagcaccttc gttctgacct gctcgggttc agctccggtg | 180 |
| gtgtgggaac ggatgtccca ggagcccca caggaaatgg ccaaggccca ggatggcacc | 240 |
| ttctccagcg tgctcacact gaccaacctc actgggctag acacgggaga atactttgc | 300 |
| acccacaatg actcccgtgg actggagacc gatgagcgga acggctcta catctttgtg | 360 |
| ccagatccca ccgtgggctt cctccctaat gatgccgagg aactattcat ctttctcacg | 420 |
| gaaataactg agatcaccat tccatgccga gtaacagacc cacagctggt ggtgacactg | 480 |
| cacgagaaga aggggacgt tgcactgcct gtccctatg atcaccaacg tggctttttt | 540 |
| ggtatctttg aggacagaag ctacatctgc aaaaccacca ttggggacag ggaggtggat | 600 |
| tctgatgcct actatgtcta cagactccag gtgtcatcca ccggtggagg tggaggtgga | 660 |
| ggtggaggtc ctaaatcttg tgacaaaact cacacatgcc caccgtgccc agcacctgaa | 720 |
| ctcctggggg gaccgtcagt cttcctcttc cccccaaaac ccaaggacac cctcatgatc | 780 |
| tcccggaccc ctgaggtcac atgcgtggtg gtggacgtga gccacgaaga ccctgaggtc | 840 |
| aagttcaact ggtacgtgga cggcgtggag gtgcataatg ccaagacaaa gccgcgggag | 900 |
| gagcagtaca acagcacgta ccgtgtggtc agcgtcctca ccgtcctgca ccaggactgg | 960 |
| ctgaatggca aggagtacaa gtgcaaggtc tccaacaaag ccctcccagc ccccatcgag | 1020 |
| aaaaccatct ccaaagccaa agggcagccc cgagaaccac aggtgtacac cctgcccca | 1080 |
| tcccgggatg agctgaccaa gaaccaggtc agcctgacct gcctggtcaa aggcttctat | 1140 |
| cccagcgaca tcgccgtgga gtgggagagc aatgggcagc cggagaacaa ctacaagacc | 1200 |
| acgcctcccg tgctggactc cgacggctcc ttcttcctct acagcaagct caccgtggac | 1260 |
| aagagcaggt ggcagcaggg gaacgtcttc tcatgctccg tgatgcatga ggctctgcac | 1320 |
| aaccactaca cgcagaagag cctctccctg tctccgggta aatag | 1365 |

<210> SEQ ID NO 21
<211> LENGTH: 2616
<212> TYPE: DNA
<213> ORGANISM: Artificial Sequence
<220> FEATURE:
<223> OTHER INFORMATION: Synthetic Construct

<400> SEQUENCE: 21

| | |
|---|---|
| atggtcagct actgggacac cggggtcctg ctgtgcgcgc tgctcagctg tctgcttctc | 60 |
| acaggatctg gtagaccttt cgtagagatg tacagtgaaa tccccgaaat tatacacatg | 120 |
| actgaaggaa gggagctcgt cattccctgc cgggttacgt cacctaacat cactgttact | 180 |
| ttaaaaaagt ttccacttga cactttgatc cctgatggaa aacgcataat ctgggacagt | 240 |
| agaaagggct tcatcatatc aaatgcaacg tacaaagaaa tagggcttct gacctgtgaa | 300 |
| gcaacagtca atgggcattt gtataagaca aactatctca cacatcgaca aaacctcgagt | 360 |
| tccagctcct cttcctcaag ccagatctct cagggcctgg tcgtcacacc cccggggcca | 420 |

```
gagcttgtcc tcaatgtctc cagcaccttc gttctgacct gctcgggttc agctccggtg    480
gtgtgggaac ggatgtccca ggagccccca caggaaatgg ccaaggccca ggatggcacc    540
ttctccagcg tgctcacact gaccaacctc actgggctag acacgggaga atactttgc     600 acccacaatg actcccgtgg actggagacc gatgagcgga aacggctcta catctttgtg    660
ccagatccca ccgtgggctt cctccctaat gatgccgagg aactattcat ctttctcacg    720
gaaataactg agatcaccat tccatgccga gtaacagacc cacagctggt ggtgacactg    780
cacgagaaga aggggacgt tgcactgcct gtccc ctatg atcaccaacg tggctttttt     840
ggtatctttg aggacagaag ctacatctgc aaaaccacca ttggggacag ggaggtggat    900
tctgatgcct actatgtcta cagactccag gtgtcatcca tcaacgtctc tgtgaacgca    960
gtgcagactg tggtccgcca gggtgagaac atcaccctca tgtgcattgt gatcgggaat   1020
gaggtggtca acttcgagtg gacatacccc cgcaaagaaa gtgggcggct ggtggagccg   1080
gtgactgact tcctcttgga tatgccttac cacatccgct ccatcctgca catccccagt   1140
gccgagttag aagactcggg gacctacacc tgcaatgtga cggagagtgt gaatgaccat   1200
caggatgaaa aggccatcaa catcaccgtg gttgagagcg ctacgtgcg gctcctggga    1260 gaggtgggca cactacaatt tgctgagctg catcggagcc ggacactgca ggtagtgttc   1320
gaggcctacc caccgcccac tgtcctgtgg ttcaaagaca accgcaccct gggcgactcc   1380
agcgctggcg aaatcgccct gtccacgcgc aacgtgtcgg agacccggta tgtgtcagag   1440
ctgacactgg ttcgcgtgaa ggtggcagag gctggccact acaccatgcg ggccttccat   1500
gaggatgctg aggtccagct ctccttccag ctacagatca atgtccctgt ccagtgctg    1560 gagctaagtg agagccaccc tgacagtggg aacagacag tccgctgtcg tggccggggc    1620
atgccccagc cgaacatcat ctggtctgcc tgcagagacc tcaaaaggtg tccacgtgag   1680
ctgccgccca cgctgctggg aacagttcc gaagaggaga gccagctgga gactaacgtg    1740
acgtactggg aggaggagca ggagtttgag gtggtgagca cactgcgtct gcagcacgtg   1800
gatcggccac tgtcggtgcg ctgcacgctg cgcaacgctg tgggccagga cacgcaggag   1860
gtcatcgtgg tgccacactc cttgcccttt accggtggag gtggaggtgg aggtggaggt   1920
cctaaatctt gtgacaaaac tcacacatgc ccaccgtgcc cagcacctga actcctgggg   1980
ggaccgtcag tcttcctctt ccccccaaaa cccaaggaca ccctcatgat ctcccggacc   2040
cctgaggtca catgcgtggt ggtggacgtg agccacgaag accctgaggt caagttcaac   2100
tggtacgtgg acggcgtgga ggtgcataat gccaagacaa agccgcggga ggagcagtac   2160
aacagcacgt accgtgtggt cagcgtcctc accgtcctgc accaggactg gctgaatggc   2220
aaggagtaca agtgcaaggt ctccaacaaa gccctcccag cccccatcga gaaaaccatc   2280
tccaaagcca aagggcagcc ccgagaacca caggtgtaca ccctgccccc atcccgggat   2340
gagctgacca agaaccaggt cagcctgacc tgcctggtca aaggcttcta tcccagcgac   2400
atcgccgtgg agtgggagag caatgggcag ccggagaaca actacaagac cacgcctccc   2460
gtgctggact ccgacggctc cttcttcctc tacagcaagc tcaccgtgga caagagcagg   2520
tggcagcagg ggaacgtctt ctcatgctcc gtgatgcatg aggctctgca caaccactac   2580
acgcagaaga gcctctccct gtctccgggt aaatag                              2616
```

<210> SEQ ID NO 22
<211> LENGTH: 2619
<212> TYPE: DNA
<213> ORGANISM: Artificial Sequence
<220> FEATURE:
<223> OTHER INFORMATION: Synthetic Construct

<400> SEQUENCE: 22

```
atgcggcttc cgggtgcgat gccagctctg gccctcaaag gcgagctgct gttgctgtct      60
ctcctgttac ttctggaacc acagatctct cagggcctgg tcgtcacacc cccggggcca     120
gagcttgtcc tcaatgtctc cagcaccttc gttctgacct gctcgggttc agctccggtg     180
gtgtgggaac ggatgtccca ggagccccca caggaaatgg ccaaggccca ggatggcacc     240
ttctccagcg tgctcacact gaccaacctc actgggctag acacgggaga atactttgc      300
acccacaatg actcccgtgg actggagacc gatgagcgga acggctcta catctttgtg      360
ccagatccca ccgtgggctt cctccctaat gatgccgagg aactattcat ctttctcacg     420
gaaataactg agatcaccat tccatgccga gtaacagacc cacagctggt ggtgacactg     480
cacgagaaga aggggacgt tgcactgcct gtcccctatg atcaccaacg tggcttttt      540
ggtatctttg aggacagaag ctacatctgc aaaaccacca ttggggacag ggaggtggat     600
tctgatgcct actatgtcta cagactccag gtgtcatcca tcaacgtctc tgtgaacgca     660
gtgcagactg tggtccgcca gggtgagaac atcaccctca tgtgcattgt gatcgggaat     720
gaggtggtca acttcgagtg gacatacccc cgcaaagaaa gtgggcggct ggtggagccg     780
gtgactgact cctcttgga tatgccttac cacatccgct ccatcctgca catccccagt     840
gccgagttag aagactcggg gacctacacc tgcaatgtga cggagagtgt gaatgaccat     900
caggatgaaa aggccatcaa catcaccgtg gttgagagcg gctacgtgcg gctcctggga     960
gaggtgggca cactacaatt tgctgagctg catcggagcc ggacactgca ggtagtgttc    1020
gaggcctacc caccgcccac tgtcctgtgg ttcaaagaca accgcacccct gggcgactcc   1080
agcgctggcg aaatcgccct gtccacgcgc aacgtgtcgg agacccggta tgtgtcagag    1140
ctgacactgg ttcgcgtgaa ggtggcagag gctggccact acaccatgcg ggccttccat    1200
gaggatgctg aggtccagct ctccttccag ctacagatca tgtccctgt ccgagtgctg     1260
gagctaagtg agagccaccc tgacagtggg aacagacag tccgctgtcg tggccggggc     1320
atgccccagc cgaacatcat ctggtctgcc tgcagagacc tcaaaaggtg tccacgtgag    1380
ctgccgccca cgctgctggg aacagttcc gaagaggaga ccagctgga gactaacgtg      1440
acgtactggg aggaggagca ggagtttgag gtggtgagca cactgcgtct gcagcacgtg    1500
gatcggccac tgtcggtgcg ctgcacgctg cgcaacgctg tgggccagga cacgcaggag    1560
gtcatcgtgg tgccacactc cttgccctttt agttccagct cctcttcctc aagctcgcct   1620
ttcgtagaga tgtacagtga atccccgaa attatacaca tgactgaagg aagggagctc    1680
gtcattccct gccgggttac gtcacctaac atcactgtta ctttaaaaaa gtttccactt    1740
gacactttga tccctgatgg aaaacgcata atctgggaca gtagaaaggg cttcatcata    1800
tcaaatgcaa cgtacaaaga atagggcttt ctgacctgtg aagcaacagt caatgggcat    1860
ttgtataaga caaactatct cacacatcga caaaccggtg gaggtggagg tggaggtgga    1920
ggtcctaaat cttgtgacaa aactcacaca tgcccaccgt gcccagcacc tgaactcctg    1980
gggggaccgt cagtcttcct cttccccca aacccaagg acaccctcat gatctcccgg     2040
accctgagg tcatgtgcgt ggtggtggac gtgagccacg aagaccctga ggtcaagttc     2100
aactggtacg tggacggcgt ggaggtgcat aatgccaaga caaagccgcg ggaggagcag    2160
tacaacagca cgtaccgtgt ggtcagcgtc ctcaccgtcc tgcaccagga ctggctgaat    2220
```

| | |
|---|---|
| ggcaaggagt acaagtgcaa ggtctccaac aaagccctcc cagcccccat cgagaaaacc | 2280 |
| atctccaaag ccaaagggca gccccgagaa ccacaggtgt acaccctgcc cccatcccgg | 2340 |
| gatgagctga ccaagaacca ggtcagcctg acctgcctgg tcaaaggctt ctatcccagc | 2400 |
| gacatcgccg tggagtggga gagcaatggg cagccggaga caactacaa gaccacgcct | 2460 |
| cccgtgctgg actccgacgg ctccttcttc ctctacagca agctcaccgt ggacaagagc | 2520 |
| aggtggcagc aggggaacgt cttctcatgc tccgtgatgc atgaggctct gcacaaccac | 2580 |
| tacacgcaga agagcctctc cctgtctccg ggtaaatag | 2619 |

<210> SEQ ID NO 23
<211> LENGTH: 1971
<212> TYPE: DNA
<213> ORGANISM: Artificial Sequence
<220> FEATURE:
<223> OTHER INFORMATION: Synthetic Construct

<400> SEQUENCE: 23

| | |
|---|---|
| atggtcagct actgggacac cggggtcctg ctgtgcgcgc tgctcagctg tctgcttctc | 60 |
| acaggatctg gtagaccttt cgtagagatg tacagtgaaa tccccgaaat tatacacatg | 120 |
| actgaaggaa gggagctcgt cattccctgc cgggttacgt cacctaacat cactgttact | 180 |
| ttaaaaaagt ttccacttga cactttgatc cctgatggaa aacgcataat ctgggacagt | 240 |
| agaaagggct tcatcatatc aaatgcaacg tacaaagaaa tagggcttct gacctgtgaa | 300 |
| gcaacagtca tgggcattt gtataagaca aactatctca cacatcgaca aacctcgagt | 360 |
| tccagctcct cttcctcaag ccagatctct cagggcctgg tcgtcacacc cccggggcca | 420 |
| gagcttgtcc tcaatgtctc cagcaccttc gttctgacct gctcgggttc agctccggtg | 480 |
| gtgtgggaac ggatgtccca ggagccccca caggaaatgg ccaaggccca ggatggcacc | 540 |
| ttctccagcg tgctcacact gaccaacctc actgggctag acacgggaga atactttgc | 600 |
| acccacaatg actcccgtgg actggagacc gatgagcgga acggctcta catctttgtg | 660 |
| ccagatccca ccgtgggctt cctccctaat gatgccgagg aactattcat ctttctcacg | 720 |
| gaaataactg agatcaccat tccatgccga gtaacagacc acagctggt ggtgacactg | 780 |
| cacgagaaga aggggacgt tgcactgcct gtcccctatg atcaccaacg tggcttttt | 840 |
| ggtatctttg aggacagaag ctacatctgc aaaaccacca ttggggacag ggaggtggat | 900 |
| tctgatgcct actatgtcta cagactccag gtgtcatcca tcaacgtctc tgtgaacgca | 960 |
| gtgcagactg tggtccgcca gggtgagaac atcccctca tgtgcattgt gatcgggaat | 1020 |
| gaggtggtca cttcgagtg gacataccc cgcaaagaaa gtgggcggct ggtggagccg | 1080 |
| gtgactgact tcctcttgga tatgccttac cacatccgct ccatcctgca catccccagt | 1140 |
| gccgagttag aagactcggg gacctacacc tgcaatgtga cggagagtgt aatgaccat | 1200 |
| caggatgaaa aggccatcaa catcaccgtg gttgagagcg gctacaccgg tggaggtgga | 1260 |
| ggtggaggtg gaggtcctaa atcttgtgac aaaactcaca catgcccacc gtgcccagca | 1320 |
| cctgaactcc tggggggacc gtcagtcttc ctcttccccc caaaacccaa ggacaccctc | 1380 |
| atgatctccc ggacccctga ggtcacatgc gtggtggtgg acgtgagcca cgaagaccct | 1440 |
| gaggtcaagt tcaactggta cgtggacggc gtggaggtgc ataatgccaa gacaaagccg | 1500 |
| cgggaggagc agtacaacag cacgtaccgt gtggtcagcg tcctcaccgt cctgcaccag | 1560 |
| gactggctga atggcaagga gtacaagtgc aaggtctcca acaaagccct cccagccccc | 1620 |
| atcgagaaaa ccatctccaa agccaaaggg cagccccgag aaccacaggt gtacaccctg | 1680 |

| | |
|---|---|
| ccccatccc gggatgagct gaccaagaac caggtcagcc tgacctgcct ggtcaaaggc | 1740 |
| ttctatccca gcgacatcgc cgtggagtgg gagagcaatg ggcagccgga gaacaactac | 1800 |
| aagaccacgc ctcccgtgct ggactccgac ggctccttct tcctctacag caagctcacc | 1860 |
| gtggacaaga gcaggtggca gcaggggaac gtcttctcat gctccgtgat gcatgaggct | 1920 |
| ctgcacaacc actacacgca gaagagcctc tccctgtctc cgggtaaata g | 1971 |

<210> SEQ ID NO 24
<211> LENGTH: 1977
<212> TYPE: DNA
<213> ORGANISM: Artificial Sequence
<220> FEATURE:
<223> OTHER INFORMATION: Synthetic Construct

<400> SEQUENCE: 24

| | |
|---|---|
| atgcggcttc cgggtgcgat gccagctctg ccctcaaag gcgagctgct gttgctgtct | 60 |
| ctcctgttac ttctggaacc acagatctct cagggcctgg tcgtcacacc cccggggcca | 120 |
| gagcttgtcc tcaatgtctc cagcaccttc gttctgacct gctcgggttc agctccggtg | 180 |
| gtgtgggaac ggatgtccca ggagcccca caggaaatgg ccaaggccca ggatggcacc | 240 |
| ttctccagcg tgctcacact gaccaacctc actgggctag acacgggaga atactttgc | 300 |
| acccacaatg actcccgtgg actggagacc gatgagcgga acggctcta catctttgtg | 360 |
| ccagatccca ccgtgggctt cctccctaat gatgccgagg aactattcat ctttctcacg | 420 |
| gaaataactg agatcaccat tccatgccga gtaacagacc cacagctggt ggtgacactg | 480 |
| cacgagaaga aggggacgt tgcactgcct gtccccatg atcaccaacg tggctttttt | 540 |
| ggtatctttg aggacagaag ctacatctgc aaaaccacca ttggggacag ggaggtggat | 600 |
| tctgatgcct actatgtcta cagactccag gtgtcatcca tcaacgtctc tgtgaacgca | 660 |
| gtgcagactg tggtccgcca gggtgagaac atcaccctca tgtgcattgt gatcgggaat | 720 |
| gaggtggtca cttcgagtg gacatacccc cgcaaagaaa gtgggcggct ggtggagccg | 780 |
| gtgactgact tcctcttgga tatgccttac acatccgct ccatcctgca catccccagt | 840 |
| gccgagttag aagactcggg gacctacacc tgcaatgtga cggagagtgt gaatgaccat | 900 |
| caggatgaaa aggccatcaa catcaccgtg gttgagagcg gctacagttc cagctcctct | 960 |
| tcctcaagct cgagaccttt cgtagagatg tacagtgaaa tccccgaaat tatacacatg | 1020 |
| actgaaggaa gggagctcgt cattccctgc cgggttacgt cacctaacat cactgttact | 1080 |
| ttaaaaaagt ttccacttga cactttgatc cctgatggaa aacgcataat ctgggacagt | 1140 |
| agaaagggct tcatcatatc aaatgcaacg tacaaagaaa tagggcttct gacctgtgaa | 1200 |
| gcaacagtca atgggcattt gtataagaca aactatctca cacatcgaca aaccggtgga | 1260 |
| ggtggaggtg gaggtggagg tcctaaatct tgtgacaaaa ctcacacatg cccaccgtgc | 1320 |
| ccagcacctg aactcctggg gggaccgtca gtcttcctct tccccccaaa acccaaggac | 1380 |
| accctcatga tctcccggac ccctgaggtc acatgcgtgg tggtggacgt gagccacgaa | 1440 |
| gaccctgagg tcaagttcaa ctggtacgtg gacggcgtgg aggtgcataa tgccaagaca | 1500 |
| aagccgcggg aggagcagta caacagcacg taccgtgtgg tcagcgtcct caccgtcctg | 1560 |
| caccaggact ggctgaatgg caaggagtac aagtgcaagg tctccaacaa agccctccca | 1620 |
| gcccccatcg agaaaaccat ctccaaagcc aaagggcagc ccgagaacc acaggtgtac | 1680 |
| accctgcccc catcccggga tgagctgacc aagaaccagg tcagcctgac ctgcctggtc | 1740 |
| aaaggcttct atcccagcga catcgccgtg gagtgggaga gcaatgggca gccggagaac | 1800 | aactacaaga ccacgcctcc cgtgctggac tccgacggct ccttcttcct ctacagcaag    1860 ctcaccgtgg acaagagcag gtggcagcag gggaacgtct tctcatgctc cgtgatgcat    1920 gaggctctgc acaaccacta cacgcagaag agcctctccc tgtctccggg taaatag      1977

```
<210> SEQ ID NO 25
<211> LENGTH: 23
<212> TYPE: DNA
<213> ORGANISM: Artificial Sequence
<220> FEATURE:
<223> OTHER INFORMATION: Synthetic Construct

<400> SEQUENCE: 25
```
gactagtatg cggcttccgg gtg                                              23

```
<210> SEQ ID NO 26
<211> LENGTH: 25
<212> TYPE: DNA
<213> ORGANISM: Artificial Sequence
<220> FEATURE:
<223> OTHER INFORMATION: Synthetic Construct

<400> SEQUENCE: 26
```
accggtggat gacacctgga gtctg                                            25

```
<210> SEQ ID NO 27
<211> LENGTH: 24
<212> TYPE: DNA
<213> ORGANISM: Artificial Sequence
<220> FEATURE:
<223> OTHER INFORMATION: Synthetic Construct

<400> SEQUENCE: 27
```
ctatgtctac agactccagg tgtc                                             24

```
<210> SEQ ID NO 28
<211> LENGTH: 25
<212> TYPE: DNA
<213> ORGANISM: Artificial Sequence
<220> FEATURE:
<223> OTHER INFORMATION: Synthetic Construct

<400> SEQUENCE: 28
```
accggtaaag ggcaaggagt gtggc                                            25

```
<210> SEQ ID NO 29
<211> LENGTH: 32
<212> TYPE: DNA
<213> ORGANISM: Artificial Sequence
<220> FEATURE:
<223> OTHER INFORMATION: Synthetic Construct

<400> SEQUENCE: 29
```
cctccaccgg tgtagccgct ctcaaccacg gt                                    32

```
<210> SEQ ID NO 30
<211> LENGTH: 28
<212> TYPE: DNA
<213> ORGANISM: Artificial Sequence
<220> FEATURE:
<223> OTHER INFORMATION: Synthetic Construct

<400> SEQUENCE: 30
```
cccgggacta gtatgcggct tccgggtg                                         28

```
<210> SEQ ID NO 31
<211> LENGTH: 11
<212> TYPE: DNA
<213> ORGANISM: Artificial Sequence
<220> FEATURE:
<223> OTHER INFORMATION: Synthetic Construct

<400> SEQUENCE: 31
ccggttaggg a                                                               11

<210> SEQ ID NO 32
<211> LENGTH: 11
<212> TYPE: DNA
<213> ORGANISM: Artificial Sequence
<220> FEATURE:
<223> OTHER INFORMATION: Synthetic Construct

<400> SEQUENCE: 32
ggcctcccta a                                                               11

<210> SEQ ID NO 33
<211> LENGTH: 59
<212> TYPE: DNA
<213> ORGANISM: Artificial Sequence
<220> FEATURE:
<223> OTHER INFORMATION: Synthetic Construct

<400> SEQUENCE: 33
tgaggtccag ctctccttcc agctacagat caatgtccct gtccgagtgc tggagtagc          59

<210> SEQ ID NO 34
<211> LENGTH: 60
<212> TYPE: DNA
<213> ORGANISM: Artificial Sequence
<220> FEATURE:
<223> OTHER INFORMATION: Synthetic Construct

<400> SEQUENCE: 34
ggccgctact ccagcactcg dacagggaca ttgatctgta gctggaagga gagctggacc         60

<210> SEQ ID NO 35
<211> LENGTH: 407
<212> TYPE: DNA
<213> ORGANISM: Artificial Sequence
<220> FEATURE:
<223> OTHER INFORMATION: Synthetic Construct

<400> SEQUENCE: 35
actagtggcg gccgccacca tggtcagcta ctgggacacc ggggtcctgc tgtgcgcgct         60
gctcagctgt ctgcttctca caggatctgg tagacctttc gtagagatgt acagtgaaat        120
ccccgaaatt atacacatga ctgaaggaag ggagctcgtc attccctgcc gggttacgtc        180
acctaacatc actgttactt taaaaaagtt tccacttgac actttgatcc ctgatggaaa        240
acgcataatc tgggacagta gaaagggctt catcatatca aatgcaacgt acaaagaaat        300
agggcttctg acctgtgaag caacagtcaa tgggcatttg tataagacaa actatctcac        360
acatcgacaa acctcgagtt ccagctcctc ttcctcaagc cagatct                      407

<210> SEQ ID NO 36
<211> LENGTH: 689
<212> TYPE: DNA
<213> ORGANISM: Artificial Sequence
<220> FEATURE:
<223> OTHER INFORMATION: Synthetic Construct
```

<400> SEQUENCE: 36

```
ccacgctgct ggggaacagt tccgaagagg agagccagct ggagactaac gtgacgtact      60
gggaggagga gcaggagttt gaggtggtga gcacactgcg tctgcagcac gtggatcggc     120
cactgtcggt gcgctgcacg ctgcgcaacg ctgtgggcca ggacacgcag gaggtcatcg     180
tggtgccaca ctccttgccc tttagttcca gctcctcttc ctcaagctcg agacctttcg     240
tagagatgta cagtgaaatc cccgaaatta tacacatgac tgaaggaagg gagctcgtca     300
ttccctgccg ggttacgtca cctaacatca ctgttacttt aaaaaagttt ccacttgaca     360
ctttgatccc tgatggaaaa cgcataatct gggacagtag aaagggcttc atcatatcaa     420
atgcaacgta caagaaaata gggcttctga cctgtgaagc aacagtcaat gggcatttgt     480
ataagacaaa ctatctcaca catcgacaaa ccggtggagg tggaggtgga ggtgagggtc     540
ctaaatcttg tgacaaaact cacacatgcc caccgtgccc agcacctgaa ctcctggggg     600
gaccgtcagt cttcctcttc cccccaaaac ccaaggacac cctcatgatc tcccggaccc     660
ctgaggtcac atgcgtggtg gtggacgtg                                       689
```

<210> SEQ ID NO 37
<211> LENGTH: 460
<212> TYPE: DNA
<213> ORGANISM: Artificial Sequence
<220> FEATURE:
<223> OTHER INFORMATION: Synthetic Construct

<400> SEQUENCE: 37

```
gactgtggtc cgccagggtg agaacatcac cctcatgtgc attgtgatcg ggaatgaggt      60
ggtcaacttc gagtggacat accccgcaa agaaagtggg cggctggtgg agccggtgac     120
tgacttcctc ttggatatgc cttaccacat ccgctccatc ctgcacatcc ccagtgccga     180
gttagaagac tcggggacct acacctgcaa tgtgacggag agtgtgaatg accatcagga     240
tgaaaaggcc atcaacatca ccgtggttga gagcggctac accggtggag gtggaggtgg     300
aggtggaggt cctaaatctt gtgacaaaac tcacacatgc ccaccgtgcc cagcacctga     360
actcctgggg ggaccgtcag tcttcctctt ccccccaaaa cccaaggaca ccctcatgat     420
ctcccggacc cctgaggtca catgcgtggt ggtggacgtg                            460
```

<210> SEQ ID NO 38
<211> LENGTH: 766
<212> TYPE: DNA
<213> ORGANISM: Artificial Sequence
<220> FEATURE:
<223> OTHER INFORMATION: Synthetic Construct

<400> SEQUENCE: 38

```
gactgtggtc cgccagggtg agaacatcac cctcatgtgc attgtgatcg ggaatgaggt      60
ggtcaacttc gagtggacat accccgcaa agaaagtggg cggctggtgg agccggtgac     120
tgacttcctc ttggatatgc cttaccacat ccgctccatc ctgcacatcc ccagtgccga     180
gttagaagac tcggggacct acacctgcaa tgtgacggag agtgtgaatg accatcagga     240
tgaaaaggcc atcaacatca ccgtggttga gagcggctac agttccagct cctcttcctc     300
aagctcgaga ccttttcgtag atgtacag tgaaatcccc gaattatac acatgactga     360
aggaagggag ctcgtcattc cctgccgggt tacgtcacct aacatcactg ttactttaaa     420
aaagtttcca cttgacactt tgatccctga tggaaaacgc ataatctggg acagtagaaa     480
gggcttcatc atatcaaatg caacgtacaa agaaataggg cttctgacct gtgaagcaac     540
```

```
agtcaatggg catttgtata agacaaacta tctcacacat cgacaaaccg gtggaggtgg    600
aggtggaggt ggaggtccta aatcttgtga caaaactcac acatgcccac cgtgcccagc    660
acctgaactc ctggggggac cgtcagtctt cctcttcccc ccaaaaccca aggacaccct    720
catgatctcc cggacccctg aggtcacatg cgtggtggtg gacgtg                   766
```

<210> SEQ ID NO 39
<211> LENGTH: 233
<212> TYPE: PRT
<213> ORGANISM: Artificial Sequence
<220> FEATURE:
<223> OTHER INFORMATION: Synthetic Construct

<400> SEQUENCE: 39

```
Met Val Ser Tyr Trp Asp Thr Gly Val Leu Leu Cys Ala Leu Leu Ser
1               5                   10                  15

Cys Leu Leu Leu Thr Gly Ser Gly Arg Pro Phe Val Glu Met Tyr Ser
            20                  25                  30

Glu Ile Pro Glu Ile Ile His Met Thr Glu Gly Arg Glu Leu Val Ile
        35                  40                  45

Pro Cys Arg Val Thr Ser Pro Asn Ile Thr Val Thr Leu Lys Lys Phe
50                  55                  60

Pro Leu Asp Thr Leu Ile Pro Asp Gly Lys Arg Ile Ile Trp Asp Ser
65                  70                  75                  80

Arg Lys Gly Phe Ile Ile Ser Asn Ala Thr Tyr Lys Glu Ile Gly Leu
                85                  90                  95

Leu Thr Cys Glu Ala Thr Val Asn Gly His Leu Tyr Lys Thr Asn Tyr
            100                 105                 110

Leu Thr His Arg Gln Thr Gly Gly Gly Gly Gly Gly Gly Gly Gly Gln
        115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230
```

<210> SEQ ID NO 40
<211> LENGTH: 702
<212> TYPE: DNA
<213> ORGANISM: Artificial Sequence
<220> FEATURE:
<223> OTHER INFORMATION: Synthetic Construct

<400> SEQUENCE: 40

```
atggtcagct actgggacac cggggtcctg ctgtgcgcgc tgctcagctg tcttcttctc    60
acaggatctg gtagaccttt cgtagagatg tacagtgaaa tccccgaaat tatacacatg    120
actgaaggaa gggagctcgt cattccctgc cgggttacgt cacctaacat cactgttact    180
```

-continued

```
ttaaaaaagt tccacttga cactttgatc cctgatggaa aacgcataat ctgggacagt    240
agaaagggct tcatcatatc aaatgcaacg tacaaagaaa tagggcttct gacctgtgaa    300
gcaacagtca atgggcattt gtataagaca aactatctca cacatcgaca aaccggtgga    360
ggtggaggtg gaggtggagg tcagccccga gaaccacagg tgtacaccct gcccccatcc    420
cgggatgagc tgaccaagaa ccaggtcagc ctgacctgcc tggtcaaagg cttctatccc    480
agcgacatcg ccgtggagtg ggagagcaat gggcagccgg agaacaacta caagaccacg    540
cctcccgtgc tggactccga cggctccttc ttcctctaca gcaagctcac cgtggacaag    600
agcaggtggc agcaggggaa cgtcttctca tgctccgtga tgcatgaggc tctgcacaac    660
cactacacgc agaagagcct ctccctgtct ccgggtaaat ag                      702
```

<210> SEQ ID NO 41
<211> LENGTH: 5
<212> TYPE: PRT
<213> ORGANISM: Artificial Sequence
<220> FEATURE:
<223> OTHER INFORMATION: Synthetic Construct

<400> SEQUENCE: 41

Gly Gly Gly Gly Ser
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Construct

<400> SEQUENCE: 42

Gly Gly Gly Gly Gly Gly Gly Gly Gly
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Construct

<400> SEQUENCE: 43

Glu Glu Glu Glu Glu Glu Glu Glu Glu
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic Construct

<400> SEQUENCE: 44

Ser Ser Ser Ser Ser Ser Ser Ser Ser
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Construct

```
<400> SEQUENCE: 45

Gly Gly Gly Gly Gly Cys Pro Pro Cys
1               5

<210> SEQ ID NO 46
<211> LENGTH: 15
<212> TYPE: PRT
<213> ORGANISM: Artificial Sequence
<220> FEATURE:
<223> OTHER INFORMATION: Synthetic Construct

<400> SEQUENCE: 46

Gly Gly Gly Gly Ser Gly Gly Gly Gly Ser Gly Gly Gly Gly Ser
1               5                   10                  15

<210> SEQ ID NO 47
<211> LENGTH: 13
<212> TYPE: PRT
<213> ORGANISM: Artificial Sequence
<220> FEATURE:
<223> OTHER INFORMATION: Synthetic Construct

<400> SEQUENCE: 47

Ser Cys Val Pro Leu Met Arg Cys Gly Gly Cys Cys Asn
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Synthetic Construct

<400> SEQUENCE: 48

Pro Ser Cys Val Pro Leu Met Arg Cys Gly Gly Cys Cys Asn
1               5                   10

<210> SEQ ID NO 49
<211> LENGTH: 9
<212> TYPE: PRT
<213> ORGANISM: Artificial Sequence
<220> FEATURE:
<223> OTHER INFORMATION: Synthetic Construct

<400> SEQUENCE: 49

Gly Asp Leu Ile Tyr Arg Asn Gln Lys
1               5

<210> SEQ ID NO 50
<211> LENGTH: 23
<212> TYPE: PRT
<213> ORGANISM: Artificial Sequence
<220> FEATURE:
<223> OTHER INFORMATION: Synthetic Construct

<400> SEQUENCE: 50

Gly Gly Gly Gly Gly Gly Gly Gly Pro Ser Cys Val Pro Leu Met
1               5                   10                  15

Arg Cys Gly Gly Cys Cys Asn
            20
```

NUCLEIC ACIDS ENCODING FUSION PROTEINS COMPRISING PDGF AND VEGF BINDING PORTIONS AND METHODS OF USING THEREOF

CROSS REFERENCE TO RELATED APPLICATION

This application is a divisional of U.S. patent application Ser. No. 14/210,354, filed Mar. 13, 2014, issued as U.S. Pat. No. 9,637,534 on May 2, 2017, which claims the benefit under 35 § USC 119(e) of prior U.S. Provisional Application No. 61/780,914, filed Mar. 13, 2013, the disclosures of which are hereby incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 159792009510SEQLIST.txt, date recorded: Jun. 21, 2017, size: 91 KB).

FIELD OF THE INVENTION

The present invention relates to fusion proteins that inhibit the PDGF pathway and the VEGF pathway, compositions of these fusion proteins as well as methods for producing and using the same.

BACKGROUND OF THE INVENTION

Formation of new blood vessels, caused by the overproduction of growth factors such as vascular endothelial growth factor (VEGF), is a key component of diseases like tumor growth, age-related macular degeneration (AMD) and proliferative diabetic retinopathy (PDR) (Connolly et al., *J Clin Invest.*, 1989, 84(5):1470-8; Ferrara et al., *Biochem Biophys Res Commun.*, 1989, 161(2):851-9; and Ferrara et al., *Nat Med.*, 1998, 4(3):336-40). Wet AMD is the most severe form of AMD disease that is characterized by abnormal neovascularization beneath the retina and often leads to permanent vision loss. Blocking of VEGF with antibodies, soluble VEGF receptors, or inhibition of VEGF receptor tyrosine kinase activity are strategies that have shown promising preclinical and clinical results in the suppression of retinal neovascularization (Aiello et al., *PNAS*, 1995, 92:10457-10461 and Willet, et al., *Nat Med.*, 2004, 10:145-147). However, recent clinical data shows that new vascular tissue typically does not regress with VEGF inhibition alone, because pericytes, which interact with endothelial cells and contribute to the establishment of the blood-retinal barrier, provide survival signals to neovascular endothelial cells and hence make them resistant to VEGF withdrawal (Benjamin et al., *Development*, 1998, 125(9)1591-8 and Patel S., *Retina*, 2009, 29(6 Suppl):S45-8). Furthermore, platelet-derived growth factor isoform B (PDGF-B) and PDGF receptor-beta (PDGFRβ), found in proliferative retinal membranes, have important roles in recruitment of pericytes for stabilization of the developing vasculature (Robbins et al., *Invest Opth Vis Sci.*, 1994, 35(10):3649-63; Lindahl et al., *Development*, 1997, 124:3943-3953; and Hellström et al., *Development*, 1999, 126:3047-3055).

The VEGF binding function of VEGFR1 (Flt-1) has been mapped to the second extracellular domain (ECD) (Davis-Smyth et al., *EMBO J.*, 1996, 15:4919-4927; Barleon et al., *J Biol Chem.*, 1997, 272:10382-10388; Wiesmann et al., *Cell*, 1997, 91:695-704; and Davis-Smyth et al., *J Biol Chem.*, 1998, 273:3216-3222). A naturally occurring alternatively spliced form of high affinity VEGF-binding receptor, soluble VEGFR1 (sFlt1), exists as a secreted protein that functions primarily as a decoy receptor (Shibuya et al., *Oncogene*, 1990, 5:519-524 and Kendall et al., *PNAS*, 1993, 90:10705-10709). A soluble receptor, VEGF-Trap, engineered for therapeutic use, has the second domain of VEGFR1 fused to the third domain of VEGFR2 (KDR) and to human IgG1 Fc region (Holash et al. 2002). An extracellular region of PDGFRβ was previously shown to antagonize PDGF-B stimulated responses (Duan et al., *J Biol Chem*, 1991, 266(1)413-8 and Ueno et al., *Science*, 1991, 252(5007):844-8). Studies with PDGFRβ-Fc chimera demonstrated that human PDGFRβ ECDs 1 to 3 are sufficient for high-affinity PDGF-B ligand binding (Heidaran et al., *FASEB J.*, 1995, 9(1):140-5 and Lokker et al., *J Biol Chem*, 1997, 272(52):33037-44). An effect of predimerization on high-affinity PDGF-B ligand binding was also described when PDGFRβ ECDs 1 to 3 were fused to glutathione S-transferase (GST) domain (Leppanen et al., *Biochemistry*, 2000, 39(9):2370-5).

Current eye treatments require monthly intravitreal injections for years by a retinal specialist. Therefore, there is a need for improved therapeutic agents and an approach to deliver such therapeutic agents to sites such as the eye.

BRIEF SUMMARY OF THE INVENTION

The invention provided herein discloses, inter alia, fusion proteins that inhibit the PDGF pathway and the VEGF pathway, compositions comprising these fusion proteins and compositions comprising viral particles comprising a nucleic acid encoding the fusion protein, as well as methods for producing and using these fusion proteins and viral particles for the treatment or prevention of a disease such as an ocular disease, an inflammatory disease, an autoimmune disease, or cancer.

Accordingly, in one aspect, the invention provides a fusion protein comprising (a) an extracellular portion of a PDGF receptor, (b) an extracellular portion of a VEGF receptor, and (c) a multimerization domain, wherein the fusion proteins binds to a PDGF and a VEGF. In some embodiments, the fusion protein is arranged from N-terminus to C-terminus in the following order: (a), (b) and (c). In some embodiments, the PDGF receptor is a PDGFRβ. In some embodiments herein, the extracellular portion of the PDGFR comprises the Ig-like domains D1-D3 of the PDGFR. In some embodiments herein, the extracellular portion of the PDGFR comprises the Ig-like domains D1-D4 of the PDGFR. In some embodiments herein, the extracellular portion of the PDGFR comprises the Ig-like domains D1-D5 of the PDGFR. In some embodiments herein, the extracellular portion of the PDGFR comprises the amino acid sequence SEQ ID NO:1, 2, or 3, or an amino acid sequence having at least 85% identity to SEQ ID NO:1, 2, or 3. In some embodiments herein, the extracellular portion of the VEGF receptor comprises an Ig-like domain D2 of a VEGF receptor. In some embodiments herein, the extracellular portion of the VEGF receptor comprises an Ig-like domain D2 of a VEGFR1 (FLT-1). In some embodiments herein, the extracellular portion of the VEGF receptor comprises an Ig-like domain D2 of a VEGFR1 (FLT-1) and an Ig-like domain D3 of a VEGFR2. In some embodiments herein, the extracellular portion of the VEGF receptor comprises the Ig-like domains D1-D3 of a VEGFR1 (FLT-1). In some embodiments herein, the extracellular portion of the VEGF receptor comprises the amino acid sequence of SEQ ID NO:4 or 5, or an amino acid sequence having at least 85% identity to SEQ ID NO:4 or 5. In some embodiments herein, the fusion protein further comprises a linker peptide between the extracellular portion of the PDGF receptor and the extracellular portion of the VEGF receptor, and/or a peptide linker between the extracellular portion of the VEGF receptor and the multimerization domain. In a further embodiment, the peptide linker comprises the amino acid sequence selected from the group consisting of $Gly_9$, $Glu_9$, $Ser_9$, $Gly_5$ Cys-Pro$_t$-Cys, $(Gly_4$-Ser$)_3$, Ser-Cys-Val-Pro-Leu-Met-Arg-Cys-Gly-Gly-Cys-Cys-Asn, Pro-Ser-Cys-Val-Pro-Leu-Met-Arg-Cys-Gly-Gly-Cys-Cys-Asn, Gly-Asp-Leu-Ile-Tyr-Arg-Asn-Gln-Lys, and $Gly_9$-Pro-Ser-Cys-Val-Pro-Leu-Met-Arg-Cys-Gly-Gly-Cys-Cys-Asn. In some embodiments herein, the multimerization domain is a Fc region of an antibody. In a further embodiment, the Fc region comprises a CH3 region of IgG1, IgG2, IgG3, or IgG4, or a CH2 and a CH3 region of IgG1, IgG2, IgG3, or IgG4. In some embodiments herein, the Fc region comprises the amino acid sequence of SEQ ID NO:6, or an amino acid sequence having at least 85% identity to SEQ ID NO:6. In some embodiments herein, the fusion protein comprises the amino acid sequence of SEQ ID NO:13 or 15, or an amino acid sequence having at least 85% identity to SEQ ID NO:13 or 15. In some embodiments herein, the fusion protein is in a multimeric form. In some of the embodiments herein, the fusion protein is in a dimeric form.

In one aspect, the invention provides a fusion protein produced by culturing a host cell comprising a nucleic acid encoding any of the fusion proteins disclosed herein under a condition that produces the fusion protein, and recovering the fusion protein produced by the host cell.

In another aspect, the invention provides a dimeric fusion protein comprising two fusion proteins, wherein each fusion protein comprises any of the fusion proteins disclosed herein.

In yet another aspect, the invention provides a composition comprising any of the fusion proteins disclosed herein and a pharmaceutically acceptable carrier.

In still another aspect, the invention provides a nucleic acid encoding any of the fusion proteins disclosed herein.

In some aspects, the invention also provides a host cell comprising a nucleotide sequence encoding any of the fusion proteins disclosed herein.

In some aspects, the invention provides a method of producing a fusion protein, comprising culturing a host cell comprising a nucleic acid encoding any of the fusion proteins disclosed herein under a condition that produces the fusion protein, and recovering the fusion protein produced by the host cell. In further embodiments, the host cell is a mammalian cell.

In another aspect, the invention provides a method of delivering a fusion protein to a subject comprising administering an effective amount of any of the fusion proteins disclosed herein to the subject. In some embodiments, the subject has macular degeneration or proliferative diabetic retinopathy. In a further embodiment, the macular degeneration is wet age-related macular degeneration or dry age-related macular degeneration. In some embodiments herein, the fusion protein is administered by intravitreal injection to the subject. In some embodiments, the subject has cancer. In some embodiments, the subject has rheumatoid arthritis, osteoarthritis, or asthma. In some embodiments, the subject has uveitis or corneal neovascularization.

In some aspects, the invention provides a vector comprising a nucleotide sequence encoding any of the fusion proteins disclosed herein. In some embodiments, the vector is a viral vector. In a further embodiment, the viral vector is a recombinant adeno-associated virus vector (rAAV). In further embodiments, the rAAV vector comprises an ITR of AAV1, AAV2, AAV3, AAV4, AAV5, AAV6, AAV7, AAV8, AAV9, AAVrh8, or AAVrh10.

In one aspect, the invention also provides an rAAV particle comprising a nucleic acid encoding any of the fusion proteins disclosed herein. In some embodiments, the rAAV particle comprises capsid proteins of AAV1, AAV2, AAV3, AAV4, AAV5, AAV6, AAV7, AAV8, AAV9, AAVrh8, or AAVrh10. In some embodiments, the nucleic acid comprises an ITR from a serotype different from the serotype of the capsid. In a further embodiment, the ITR is an ITR of AAV1, AAV2, AAV3, AAV4, AAV5, AAV6, AAV7, AAV8, AAV9, AAVrh8, or AAVrh10.

In yet another aspect, the invention provides a method of producing an rAAV particle, comprising (a) culturing a host cell under a condition that rAAV particles are produced, wherein the host cell comprises (i) one or more AAV package genes, wherein each said AAV packaging gene encodes an AAV replication or encapsidation protein; (ii) an rAAV pro-vector comprising a nucleotide encoding any of the fusion proteins disclosed herein flanked by at least one AAV ITR, and (iii) an AAV helper function; and (b) recovering the rAAV particles produced by the host cell. In a further embodiment, the rAAV particles are purified.

In still another aspect, the invention provides a method of delivering a viral vector to a subject, comprising administering any of the rAAV particles disclosed herein to the subject, wherein the fusion protein encoded by the rAAV particle is expressed in the subject. In some embodiments, the subject has macular degeneration or proliferative diabetic retinopathy. In a further embodiment, the macular degeneration is wet age-related macular degeneration or dry age-related macular degeneration. In some embodiments herein, the rAAV particle is administered by intravitreal injection to the subject. In some embodiments, the subject has cancer. In some embodiments, the subject has rheumatoid arthritis, osteoarthritis, or asthma. In some embodiments, the subject has uveitis or corneal neovascularization.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

DETAILED DESCRIPTION

Figure 1A:
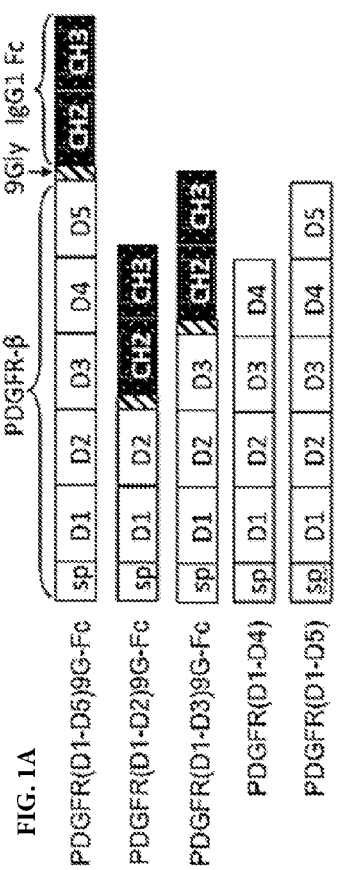
FIGS. 1A and 1B shows generation of truncated PDGFR-β soluble receptors. A) Schematic of the PDGFR-β IgG1 Fc-coupled dimerizing forms, PDGFR(D1-D5)9G-Fc, PDGFR(D1-D2)9G-Fc, and PDGFR(D1-D3)9G-Fc as well as the PDGFR-β monomeric receptor forms, PDGFR(D1-D4) and PDGFR(D1-D5). White blocks indicate PDGFR-β sequences, including the extracellular domains and the signal peptide (sp). Diagonal shaded blocks represent 9Gly linker and dark dotted blocks represent domains CH2 and CH3 of human IgG1 Fc region. B) Western blots of monomeric sPDGFR-β and IgG1 Fc-coupled dimerizing soluble receptor forms under reducing (left panel) and non-reducing (right panel) conditions. Protein was detected with anti-PDGFR-β antibody.

The present invention provides, inter alia, fusion proteins, and compositions thereof, that inhibit the plasma-derived growth factor (PDGF) signaling pathway and the vascular endothelial growth factor (VEGF) signaling pathway. A fusion protein of the invention as described herein comprises an extracellular portion of a PDGF receptor (PDGFR), an extracellular portion of a VEGF receptor (VEGFR), and a multimerization domain, wherein the fusion protein binds to a PDGF and a VEGF for inhibition of PDGF activity and VEGF activity, respectively. Also provided herein are methods for production of the fusion proteins, methods of delivery of the fusion proteins, and methods of using the fusion proteins in the treatment of ocular diseases, autoimmune diseases, inflammatory diseases, and/or cancer.

I. General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4$^{th}$ ed., Cold Spring Harbor Laboratory Press, Cold Spring Harbor, N.Y., 2012); *Current Protocols in Molecular Biology* (F. M. Ausubel, et al. eds., 2003); the series Methods in Enzymology (Academic Press, Inc.); PCR 2: A Practical Approach (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, 6$^{th}$ ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology*

(C. A. Janeway et al., 2004); *Antibodies* (P. Finch, 1997); *Antibodies: A Practical Approach* (D. Catty, ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 2011).

II. Definitions

A "vector," as used herein, refers to a recombinant plasmid or virus that comprises a nucleic acid to be delivered into a host cell, either in vitro or in vivo.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P—$NH_2$) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

A "recombinant viral vector" refers to a recombinant polynucleotide vector comprising one or more heterologous sequences (i.e., nucleic acid sequence not of viral origin). In the case of recombinant AAV vectors, the recombinant nucleic acid is flanked by at least one, preferably two, inverted terminal repeat sequences (ITRs).

A "recombinant AAV vector (rAAV vector)" refers to a polynucleotide vector comprising one or more heterologous sequences (i.e., nucleic acid sequence not of AAV origin) that are flanked by at least one, preferably two, AAV inverted terminal repeat sequences (ITRs). Such rAAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). When a rAAV vector is incorporated into a larger polynucleotide (e.g. in a chromosome or in another vector such as a plasmid used for cloning or transfection), then the rAAV vector may be referred to as a "pro-vector" which can be "rescued" by replication and encapsidation in the presence of AAV packaging functions and suitable helper functions. An rAAV can be in any of a number of forms, including, but not limited to, plasmids, linear artificial chromosomes, complexed with lips, encapsulated within liposomes, and, most preferable, encapsidated in a viral particle, particularly AAV. A rAAV vector can be packaged into an AAV virus capsid to generate a "recombinant adeno-associated virus particle (rAAV particle)".

"Heterologous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector, is a heterologous nucleotide sequence with respect to the vector.

An "inverted terminal repeat" or "ITR" sequence is a term well understood in the art and refers to relatively short sequences found at the termini of viral genomes which are in opposite orientation.

An "AAV inverted terminal repeat (ITR)" sequence, a term well-understood in the art, is an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity, allowing intrastrand base-pairing to occur within this portion of the ITR.

A "helper virus" for AAV refers to a virus that allows AAV (which is a defective parvovirus) to be replicated and packaged by a host cell. A number of such helper viruses have been identified, including adenoviruses, herpesviruses and poxviruses such as vaccinia. The adenoviruses encompass a number of different subgroups, although Adenovirus type 5 of subgroup C (Ad5) is most commonly used. Numerous adenoviruses of human, non-human mammalian and avian origin are known and are available from depositories such as the ATCC. Viruses of the herpes family, which are also available from depositories such as ATCC, include, for example, herpes simplex viruses (HSV), Epstein-Barr viruses (EBV), cytomegaloviruses (CMV) and pseudorabies viruses (PRV).

A "fusion protein" refers to a protein having two or more portions covalently linked together, where each of the portions is derived from different proteins.

"Percent (%) sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various ways that are within the skill in the art, for instance, using publicly available computer software programs, for example, those described in Current Protocols in Molecular Biology (Ausubel et al., eds., 1987), Supp. 30, section 7.7.18, Table 7.7.1, and including BLAST, BLAST-2, ALIGN or Megalign (DNASTAR) software. A preferred alignment program is ALIGN Plus (Scientific and Educational Software, Pennsylvania). Those skilled in the art can determine appropriate parameters for measuring alignment, including any algorithms needed to achieve maximal alignment over the full length of the sequences being compared. For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z, where W is the number of nucleotides scored as identical matches by the sequence alignment program in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

An "isolated" molecule (e.g., nucleic acid or protein) or cell means it has been identified and separated and/or recovered from a component of its natural environment.

An "effective amount" is an amount sufficient to effect beneficial or desired results, including clinical results. An effective amount can be administered in one or more administrations. In terms of a disease state, an effective amount is an amount sufficient to ameliorate, stabilize, or delay development of a disease.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, preventing spread (i.e., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

Reference to "about" a value or parameter herein includes (and describes) embodiments that are directed to that value or parameter per se. For example, description referring to "about X" includes description of "X."

As used herein, the singular form of the articles "a," "an," and "the" includes plural references unless indicated otherwise. For example, the phrase "a rAAV particle" includes one or more rAAV particles.

It is understood that aspects and embodiments of the invention described herein include "comprising," "consisting," and/or "consisting essentially of" aspects and embodiments.

III. Fusion Proteins and Fusion Protein Components

Plasma-Derived Growth Factor (PDGF) Receptor

Plasma-derived growth factors (PDGFs) are involved in many biological activities and have been implicated in a number of diseases such as atherosclerosis, glomerulonephritis, vascular restenosis following angioplasty, and cancer. There are at least four members of the plasma-derived growth factor (PDGF) family of proteins that regulate the PDGF signaling pathway, specifically PDGF-A, PDGF-B, PDGF-C, and PDGF-D. These four PDGFs assemble into disulfide-linked dimers via homo- or heterodimerization. At least five different dimeric isoforms of PDGF have been described to date and include PDGF-AA, PDGF-BB, PDGF-CC, PDGF-DD, and PDGF-AB, all of which bind to PDGF receptors (PDGFRs) to activate the PDGF signaling pathway. There are at least two identified PDGFRs, PDGFR-α and PDGFR-β. Each PDGFR has an extracellular region, a transmembrane domain, and an intracellular region having intracellular tyrosine kinase activity. PDGFRs can dimerize to form the homodimers PDGFR-α/PDGFR-α or PDGFR-β/PDGFR-β and the heterodimer PDGFR-α/PDGFR-β. Each of these PDGFR dimer forms recognize different dimeric isoforms of PDGF. For example, PDGFR-α/PDGFR-α recognizes PDGF-AA, AB, BB and CC ligands, PDGFR-α/PDGFR-β recognizes PDGF-AB, BB, CC, and DD, and PDGFR-β/PDGFR-β recognizes PDGF-BB and DD. Deletion mutagenesis of the PDGF-AA and -BB binding sites have been mapped to amino acids 1-314 of PDGFR-α while the PDGF-BB binding sites have been mapped to amino acids 1-315 of PDGFR-β. The extracellular region of these PDGFRs, which mediate binding to PDGFs contain five immunoglobulin (Ig)-like domains, each ranging from about 88 to about 114 amino acids in length. See Lokker et al., *J Biol Chem.*, 1997, 272(52): 33037-44, Miyazawa et al., *J Biol Chem.*, 1998, 273(39): 25495-502; and Mahadevan et al., *J Biol Chem.*, 1995, 270(46):27595-600, which are incorporated herein by reference their entirety.

The present invention provides an extracellular portion of a PDGF receptor that can be a component of any fusion protein disclosed herein. Accordingly, in one aspect, the invention provides for an extracellular portion of a PDGFR that includes, but is not limited to, PDGFR-α and PDGFR-β. In some of the embodiments herein, the PDGFR is from a mammal, such as a human. There are five Ig-like domains numbered 1, 2, 3, 4, and 5 starting from the N-terminus to the C-terminus of a PDGFR extracellular region. As used herein the terms "extracellular portion of a PDGFR" refers to one or more of the five Ig-like domains in the PDGFR extracellular region. For example, "an extracellular portion of a PDGFR" refers to one or more of any of the five Ig-like domains found in the extracellular region of a PDGFR such as Ig-like domain D1, Ig-like domain D2, Ig-like domain D3, Ig-like domain D4, or Ig-like domain D5. As used herein, terms such as "Ig-like domain D1" or "extracellular domain (ECD) 1" of a PDGFR specifically refers to the first Ig-like domain found at the N-terminus of the extracellular region of PDGFR, "Ig-like domain D2" or "ECD 1" of a PDGFR specifically refers to the second Ig-like domain from the N-terminus of the extracellular region of PDGFR, and so forth. In any of the aspects herein, an extracellular portion of a PDGFR comprises at least one Ig-like domain of one or more PDGFRs selected from the group consisting of PDGFR-α and PDGFR-β. In some aspects, an extracellular portion of a PDGFR comprises at least 1, 2, 3, 4, but no more than 5 Ig-like domains of a PDGFR (e.g., PDGFR-β). In some aspects, an extracellular portion of a PDGFR comprises 1 to 5, 1 to 4, 1 to 3, or 1 to 2 Ig-like domains of a PDGFR (e.g., PDGFR-β). For example, an extracellular portion of a PDGFR can comprise an Ig-like domain D2 of a PDGFR. In another example, an extracellular portion of a PDGFR can comprise of Ig-like domains D1 to D2 of a PDGFR (e.g., PDGFR-β). In yet another example, an extracellular portion of a PDGFR can comprise the Ig-like domains D1 to D3, the Ig-like domains D1 to D4, or the Ig-like domains D1 to D5 of a PDGFR (e.g., PDGFR-β).

An extracellular portion comprising any combination of the five Ig-like domains of each PDGFR are contemplated herein. Accordingly, in one aspect, the present invention provides an extracellular portion of a PDGFR comprising at least one Ig-like domain of two PDGFRs. In some embodiments, an extracellular portion of a PDGFR comprises at least one Ig-like domain from two PDGFRs selected from the group consisting of PDGFR-α and PDGFR-β. For example, a fusion protein as described herein can comprise an extracellular portion of a PDGFR comprising at least one Ig-like domain of PDGFR-α and at least one Ig-like domain of PDGFR-β. In some aspects, an extracellular portion of a PDGFR comprises at least 1, 2, 3, 4, 5, 6, 7, 8, 9, but no more than 10 Ig-like domains of at least two or more PDGFRs. In a further aspect, an extracellular portion of a PDGFR comprises 1 to 10, 1 to 9, 1 to 8, 1 to 7, 1 to 6, 1 to 5, 1 to 4, 1 to 3, or 1 to 2 Ig-like domains of at least two or more PDGFRs. For a further description of Ig-like domains that can be used as part of an extracellular portion of a PDGFR, see U.S. Pat. No. 5,686,572, WO2006113277, and Lokker et al., *J Biol Chem.* 1997, 272(52):33037-44, all of which are incorporated herein by reference in their entirety.

In some aspects, an extracellular portion of a PDGFR comprises the amino acid sequence selected from the group consisting of SEQ ID NOs:1-3. For example, an extracellular portion of a PDGFR comprising the amino acid sequence of SEQ ID NO:1, SEQ ID NO:2, or SEQ ID NO:3 can be a component of any fusion protein disclosed herein. In some embodiments, an extracellular portion of a PDGFR comprises the amino acid sequence selected from the group consisting of SEQ ID NOs:7 and 8.

Amino acid sequence variants of any extracellular portion of a PDGFR provided herein are also contemplated. For example, binding affinity and/or other biological properties of the extracellular portion of a PDGFR can be improved by altering the amino acid sequence encoding the protein. Amino acids sequence variants of an extracellular portion of a PDGFR can be prepared by introducing appropriate modifications into the nucleic acid sequence encoding the protein or by introducing the modification by peptide synthesis. Such modifications include, for example, deletions from, insertions into, and/or substitutions within the amino acid sequence of the extracellular portion of a PDGFR. Any combination of deletion, insertion, and substitution can be made to arrive at the final amino acid construct of the extracellular portion of a PDGFR provided that the final construct possesses the desired characteristics such as binding to a PDGF family protein and/or inhibiting activation of the PDGF pathway. Accordingly, provided herein are variants of an extracellular portion of a PDGFR that can be a component of any fusion protein disclosed herein. In some embodiments, an extracellular portion of a PDGFR comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of any one of Ig-like domains D1, D2, D3, D4, or D5 of a PDGFR-α (e.g., human PDGFR-α). In some embodiments, an extracellular portion of a PDGFR comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of any one of Ig-like domains D1, D2, D3, D4, or D5 of a PDGFR-β (e.g., human PDGFR-β). In some embodiments, an extracellular portion of a PDGFR comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an amino acid sequence selected from the group consisting of SEQ ID NOs:1-3. In some embodiments, an extracellular portion of a PDGFR comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an amino acid sequence selected from the group consisting of SEQ ID NOs:7 and 8.

Without being bound by theory, it is contemplated herein that an extracellular portion of a PDGFR inhibits activation of the PDGF pathway by binding to a PDGF family protein to block its interaction with a PDGFR. Without being bound by theory, it is also contemplated herein that an extracellular portion of a PDGFR can bind to a PDGFR for dominant negative inhibition of the PDGF signaling pathway. In some aspects, an extracellular portion of a PDGFR binds a PDGF family protein selected from the group consisting of PDGF-A, PDGF-B, PDGF-C, and PDGF-D. In some aspects, an extracellular portion of a PDGFR binds a PDGF family protein dimer selected from the group consisting of PDGF-AA, PDGF-AB, PDGF-BB, PDGF-CC, and PDGF-DD. In some aspects, an extracellular portion of a PDGFR binds a PDGFR selected from the group consisting of PDGFR-α and PDGFR-β.

An extracellular portion of a PDGFR may or may not comprise a signal peptide that serves as a signal sequence for secretion of the extracellular portion of a PDGFR from a host cell. The signal peptide can be operably linked to a nucleic acid encoding the protein of interest (e.g., an extracellular portion of a PDGFR). In some embodiments, an extracellular portion of a PDGFR comprises a signal peptide. In some embodiments, an extracellular portion of a PDGFR does not comprise a signal peptide.

Vascular Endothelial Growth Factor (VEGF) Receptor

There are at least five members of the VEGF family of proteins that regulate the VEGF signaling pathway: VEGF-A, VEGF-B, VEGF-C, VEGF-D, and placental growth factor (PlGF). Furthermore, alternative splicing of mRNA that encodes VEGF-A, VEGF-B, and PlGF results in the generation of multiple isoforms of these proteins. For example, alternative splicing of VEGF-A yields nine different isoforms including isoforms $VEGF_{121}$, $VEGF_{165}$, $VEGF_{189}$, and $VEGF_{206}$. The VEGF family of proteins activate the VEGF signaling pathway by binding to the extracellular region of transmembrane VEGF receptors. There are at least three identified VEGF receptors: VEGFR1 (also known as fms-related tyrosine kinase 1 (Flt-1)), VEGFR2 (also known as kinase insert domain receptor (KDR)) and VEGFR3 (also known as fms-like tyrosine kinase 4 (Flt-4)). VEGFRs each contain an extracellular region comprising seven immunoglobulin (Ig)-like domains, a single transmembrane domain segment, a juxtamembrane segment, and an intracellular protein-tyrosine kinase domain. The extracellular regions of VEGFRs bind to different members of the VEGF family of proteins. For example, VEGFR1 binds VEGF-A, VEGF-B, and PlGF; VEGFR2 binds all VEGF-A isoforms, VEGF-C, VEGF-D, and VEGF-E; and VEGFR3 binds to VEGF-C and VEGF-D. See Roskoski, R et al., *Crit Rev Oncol Hematol.*, 2007, 62(3):179-213, which is incorporated herein by reference its entirety, for a review of VEGF and VEGFR mediated signaling.

The present invention provides an extracellular portion of a VEGF receptor that can be a component of any fusion protein disclosed herein. Accordingly, in one aspect, the invention provides for an extracellular portion of a VEGFR that includes, but is not limited to, VEGFR1, VEGFR2, and VEGFR3. In some of the embodiments herein, the VEGFR is from a mammal, such as a human. There are seven extracellular Ig-like domains numbered 1, 2, 3, 4, 5, 6, and 7 starting from the N-terminus to the C-terminus of a VEGFR extracellular region. As used herein the terms "extracellular portion of a VEGFR" refers to one or more of the seven Ig-like domains in the VEGFR extracellular region. For example, "an extracellular portion of a VEGFR" refers to one or more of any of the seven Ig-like domains found in the extracellular region of a VEGFR such as Ig-like domain D1, Ig-like domain D2, Ig-like domain D3, Ig-like domain D4, Ig-like domain D5, Ig-like domain D6, or Ig-like domain D7. As used herein, terms such as "Ig-like domain D1" or "extracellular domain (ECD) 1" of a VEGFR both specifically refer to the first Ig-like domain found at the N-terminus of the extracellular region of VEGFR, "Ig-like domain D2" or "ECD 2" of a VEGFR both specifically refer to the second Ig-like domain from the N-terminus of the extracellular region of VEGFR, and so forth. In any of the aspects herein, an extracellular portion of a VEGFR comprises at least one Ig-like domain of one or more VEGFRs selected from the group consisting of VEGFR1, VEGFR2, and VEGFR3. In some aspects, an extracellular portion of a VEGFR comprises at least 1, 2, 3, 4, 5, 6, but no more than 7 Ig-like domains of a VEGFR (e.g., VEGFR1). In some aspects, an extracellular portion of a VEGFR comprises 1 to 7, 1 to 6, 1 to 5, 1 to 4, 1 to 3, or 1 to 2 Ig-like domains of a VEGFR (e.g., VEGFR1). For example, an extracellular portion of a VEGFR can comprise an Ig-like domain D2 of a VEGFR1. In another example, an extracellular portion of a VEGFR can comprise of Ig-like domains D1 to D3 of a VEGR1. In yet another example, an extracellular portion of a VEGFR can comprise the Ig-like domains D2 to D3 of VEGFR1 or the Ig-like domains D1 to D3 of VEGFR2.

An extracellular portion comprising any combination of the seven Ig-like domains of each VEGFR are contemplated herein. Accordingly, in one aspect, the present invention provides an extracellular portion of a VEGFR comprising at least one Ig-like domain of two or more VEGFRs. In some embodiments, an extracellular portion of a VEGFR comprises at least one Ig-like domain from two or more VEGFRs selected from the group consisting of VEGFR1, VEGFR2, and VEGFR3. For example, a fusion protein as described herein can comprise an extracellular portion of a VEGFR comprising at least one Ig-like domain of VEGFR1 and at least one Ig-like domain of VEGFR2. In another example, a fusion protein as described herein can comprise an extracellular portion of a VEGFR comprising the Ig-like domain D2 of VEGFR1 and the Ig-like domains D3 to D4 of VEGFR2. In another example, a fusion protein as described herein can comprise an extracellular portion of a VEGFR comprising the Ig-like domain D2 of VEGFR1 and the Ig-like domain D3 of VEGFR3. In some aspects, an extracellular portion of a VEGFR comprises at least 1, 2, 3, 4, 5, 6, 7, 8, 9, 10, 11, 12, 13, 14, 15, 16, 17, 18, 19, 20, but no more than 21 Ig-like domains of at least two or more VEGFRs. In a further aspect, an extracellular portion of a VEGFR comprises 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 4, 1 to 3, or 1 to 2 Ig-like domains of at least two or more VEGFRs. For a further description of Ig-like domains that can be used as part of an extracellular portion of a VEGFR, see U.S. Pat. No. 7,928,072, WO2006113277, Davis-Smyth, T., et al., *J Biol Chem*, 1998, 273:3216-3222, Holash, J., et al., *PNAS*, 2002, 99(17):11393-11398, and Pechan, P., et al., *Gene Ther*, 2009, 16:10-16, all of which are incorporated in their entirety by reference.

In some aspects, an extracellular portion of a VEGFR comprises the amino acid sequence of SEQ ID NO:4. In some aspects, an extracellular portion of a VEGFR comprises the amino acid sequence of SEQ ID NO:5. For example, an extracellular portion of a VEGFR comprising the amino acid sequence of SEQ ID NO:4 or SEQ ID NO:5 can be a component of any fusion protein disclosed herein.

Amino acid sequence variants of any extracellular portion of a VEGFR provided herein are also contemplated. For example, binding affinity and/or other biological properties of the extracellular portion of a VEGFR can be improved by altering the amino acid sequence encoding the protein. Amino acids sequence variants of an extracellular portion of a VEGFR can be prepared by introducing appropriate modifications into the nucleic acid sequence encoding the protein or by introducing the modification by peptide synthesis. Such modifications include, for example, deletions from, insertions into, and/or substitutions within the amino acid sequence of the extracellular portion of a VEGFR. Any combination of deletion, insertion, and substitution can be made to arrive at the final amino acid construct of the extracellular portion of a VEGFR provided that the final construct possesses the desired characteristics such as binding to a VEGF family protein and/or inhibiting activation of the VEGF pathway. Accordingly, provided herein are variants of an extracellular portion of a VEGFR that can be a component of any fusion protein disclosed herein. In some embodiments, an extracellular portion of a VEGFR comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of any one of Ig-like domains D1, D2, D3, D4, D5, D6, or D7 of a VEGFR1 (e.g., human VEGFR1). In some embodiments, an extracellular portion of a VEGFR comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of any one of Ig-like domains D1, D2, D3, D4, D5, D6, or D7 of a VEGFR2 (e.g., human VEGFR2). In some embodiments, an extracellular portion of a VEGFR comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of any one of Ig-like domains D1, D2, D3, D4, D5, D6, or D7 of a VEGFR3 (e.g., human VEGFR3). In some embodiments, an extracellular portion of a VEGFR comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an amino acid sequence selected from the group consisting of SEQ ID NOs:4 and 5.

Without being bound by theory, it is contemplated herein that an extracellular portion of a VEGFR inhibits activation of the VEGF pathway by binding to a VEGF family protein to block its interaction with a VEGFR. Without being bound by theory, it is also contemplated herein that an extracellular portion of a VEGFR can bind to a VEGFR for dominant negative inhibition of the VEGF signaling pathway. In some aspects, an extracellular portion of a VEGFR binds a VEGF family protein selected from the group consisting of VEGF-A, VEGF-B, VEGF-C, VEGF-D, and PlGF. In some aspects, an extracellular portion of a VEGFR binds a VEGFR (e.g., VEGFR1, VEGFR2, and/or VEGFR3).

An extracellular portion of a VEGFR may or may not comprise a signal peptide that serves as a signal sequence for secretion of the extracellular portion of a VEGFR from a host cell. The signal peptide can be operably linked to a nucleic acid encoding the protein of interest (e.g., an extracellular portion of a VEGFR). In some embodiments, an extracellular portion of a VEGFR comprises a signal peptide. In some embodiments, an extracellular portion of a VEGFR does not comprise a signal peptide.

Multimerization Domain

The present invention provides a multimerization domain (e.g., an Fc region of an antibody) that can be a component of any fusion protein disclosed herein. Multimerization domains are those portions of multimeric proteins that promote the association of subunits to form, for example dimers, trimers, tetramers, and so forth. As used herein the term "multimerizing domain" may be used to refer to a dimerizing domain, a trimerizing domain, a tetramerizing domain, and so forth. Fusion proteins comprising a multimerization domain can interact with other fusion proteins comprising a multimerization domain to produce fusion protein multimers (e.g., fusion protein dimers). For example, an IgG Fc region is a dimerizing domain that can be fused to an extracellular portion of a PDGFR or an extracellular portion of VEGFR as disclosed herein. A fusion protein comprising an extracellular portion of a PDGFR and an IgG Fc region can dimerize with another fusion protein comprising an IgG Fc region to produce a fusion protein dimer with multispecificity to at least a PDGF. A multimerization domain can be any polypeptide that forms a multimer with another polypeptide. Multimerization domains that can be used are known in the art. See. U.S. Pat. No. 7,928,072 and WO2006/113277. For example, an Fc region of an IgG1 or IgG2 lambda heavy chain, such as the CH3 domain alone or both the CH2 and CH3 domains, can be used as a multimerization domain. Other Fc regions from immunoglobulin isotypes, such as IgA, IgM, IgD, or IgE can also be used as multimerization domains. As used herein the term "Fc region" is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. In one embodiment, the multimerization domain is an Fc region of an antibody. In a further embodiment, the Fc region of an antibody is selected from the group consisting of an IgG Fc region, an IgA Fc region, an IgM Fc region, an IgD Fc region, and an IgE Fc region. In another further embodiment, the Fc region of an antibody is selected from the group consisting of an IgG1 Fc region, an IgG2 Fc region, an IgG3 Fc region, and an IgG4 Fc region. In some aspects, the Fc region comprises a CH3 region of IgG1, IgG2, IgG3, or IgG4. In some aspects, the Fc region comprises a CH2 and a CH3 region of IgG1, IgG2, IgG3, or IgG4. Amino acid sequences encoding immunoglobulins that comprise Fc regions are well known in the art. For example, the IgG1 lambda heavy chain amino acid sequence can be found under Genbank accession no. CAA75032. An Fc region of an immunoglobulin can be obtained by cleavage with the enzyme papain or by other means. In some embodiments, the Fc region comprises the amino acid sequence of SEQ ID NO:6. The multimerization domain of a VEGF can also be used such as the multimerization domain of VEGF-A. VEGF-A is encoded by a nucleic acid shown at Genbank accession no. NM003376. For example, the multimerization domain of VEGF-A is encoded by VEGF-A exon 3 and can be linked to any of the fusion protein components disclosed herein such as the extracellular portion of a PDGFR and/or the extracellular portion of a VEGFR.

In some embodiments, amino acid sequence variants of a multimerization domain are provided herein. For example, it may be desirable to improve the biological properties (e.g., multimerization properties) of the multimerization domain. Amino acids sequence variants of a multimerization domain can be prepared by introducing appropriate modifications into the nucleic acid sequence encoding the protein or by introducing the modification by peptide synthesis. Such modifications include, for example, deletions from, insertions into, and/or substitutions within the amino acid sequence of the multimerization domain. Any combination of deletion, insertion, and substitution can be made to arrive at the final amino acid construct of the multimerization provided that the final construct possesses the desired characteristics such as formation of multimer proteins. Accordingly, provided herein are variants of a multimerization domain (e.g., an Fc region of an antibody) that can be a component of any fusion protein disclosed herein. In some embodiments, an Fc region comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of a CH3 region of IgG1, IgG2, IgG3, or IgG4. In some embodiments, an Fc region comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of a CH2 and a CH3 region of IgG1, IgG2, IgG3, or IgG4. In some embodiments, an Fc region comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:6. Variants of multimerization domains are well known in the art. See for example U.S. Patent Application No. 2012/0251531, which is incorporated herein by reference in its entirety.

Linkers

Components of the fusion protein (e.g., the extracellular portion of a PDGFR, the extracellular portion of a VEGFR, or the multimerization domain) may be linked by a linking moiety such as a peptide linker. Preferably, the linker increases flexibility of the fusion protein components and does not interfere significantly with the structure of each functional component within the fusion protein. In some embodiments, the linker moiety is a peptide linker. In some embodiments, the peptide linker comprises 2 to 100 amino acids. In some embodiments, the peptide linker comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 but no greater than 100 amino acids. In some embodiments, the peptide linker is between 5 to 75, 5 to 50, 5 to 25, 5 to 20, 5 to 15, 5 to 10 or 5 to 9 amino acids in length. Exemplary linkers include linear peptides having at least two amino acid residues such as Gly-Gly, Gly-Ala-Gly, Gly-Pro-Ala, Gly-Gly-Gly-Gly-Ser. Suitable linear peptides include poly glycine, polyserine, polyproline, polyalanine and oligopeptides consisting of alanyl and/or serinyl and/or prolinyl and/or glycyl amino acid residues. In some embodiments, the peptide linker comprises the amino acid sequence selected from the group consisting of $Gly_9$, $Glu_9$, $Ser_9$, $Gly_5$-$Cys$-$Pro_2$-$Cys$, $(Gly_4$-$Ser)_3$, Ser-Cys-Val-Pro-Leu-Met-Arg-Cys-Gly-Gly-Cys-Cys-Asn, Pro-Ser-Cys-Val-Pro-Leu-Met-Arg-Cys-Gly-Gly-Cys-Cys-Asn, Gly-Asp-Leu-Ile-Tyr-Arg-Asn-Gln-Lys, and $Gly_9$-Pro-Ser-Cys-Val-Pro-Leu-Met-Arg-Cys-Gly-Gly-Cys-Cys-Asn.

Linker moieties can also be made from other polymers, such as polyethylene glycol. Such linkers can have from 10 to 1000, 10 to 500, 10 to 250, 10 to 100, or 10 to 50 ethylene glycol monomer units. Suitable polymers should be of a size similar to the size occupied by the appropriate range of amino acid residues. A typical sized polymer would provide a spacing of from about 10-25 angstroms.

The linker moiety may be a protein multivalent linker that has branched "arms" that link multiple fusion protein components in a non-linear fashion. In some embodiments, a multivalent linker has about 3 to 40 amino acid residues, all or some of which provide attachment sites for conjugation with fusion protein components (e.g., the extracellular portion of a PDGFR, the extracellular portion of a VEGFR, or the multimerization domain). Alpha amino groups and alpha carboxylic acids can serve as attachment sites. Exemplary multivalent linkers include, but are not limited to, polylysines, polyornithines, polycysteines, polyglutamic acid and polyaspartic acid. Optionally, amino acid residues with inert side chains, e.g., glycine, alanine and valine, can be included in the amino acid sequence. The linkers may also be a non-peptide chemical entity such as a chemical linker that is suitable for administration (e.g., ocular administration) once attached to a fusion protein component (e.g., the extracellular portion of a PDGFR, the extracellular portion of a VEGFR, and/or the multimerization domain). The chemical linker may be a bifunctional linker, each of which reacts with a fusion protein component (e.g., the extracellular portion of a PDGFR, the extracellular portion of a VEGFR, and/or the multimerization domain). Alternatively, the chemical linker may be a branched linker that has a multiplicity of appropriately spaced reactive groups, each of which can react with a functional group of a fusion protein component (e.g., the extracellular portion of a PDGFR, the extracellular portion of a VEGFR, and/or the multimerization domain). The fusion protein components (e.g., the extracellular portion of a PDGFR, the extracellular portion of a VEGFR, and/or the multimerization domain) are attached by way of reactive functional groups and are spaced such that steric hindrance does not substantially interfere with formation of covalent bonds between some of the reactive functional groups (e.g., amines, carboxylic acids, alcohols, aldehydes and thiols) and the peptide. Examples of linker moieties include, but are not limited to, those disclosed in Tarn, J. P., et al., *J. of Immunol Methods*, 1996, 196:17-32.

The linker moieties may be used to link any of the components of the fusion proteins disclosed herein. For example, a peptide linker (e.g., $Gly_9$) can be used to link the C-terminus end of an extracellular portion of a PDGFR to the N-terminus end of an extracellular portion of a VEGFR and can be further used to link the C-terminus end of the extracellular portion of a VEGR to the N-terminus end of a multimerization domain (e.g., an IgG1 Fc region). In some embodiments, a linker is used between an extracellular portion of a PDGFR and a multimerization domain. In some embodiments, a linker is used between an extracellular portion of a VEGFR and a multimerization domain. In some embodiments, a linker is used between an extracellular portion of a PDGFR and an extracellular portion of a VEGFR. In some embodiments, the fusion protein comprises a linker between an extracellular portion of a PDGFR and an extracellular region of a VEGFR, and a linker between the extracellular region of the VEGFR and a multimerization domain (e.g., Fc region). In some embodiments, a fusion protein comprises at least one linker but no more than four linkers. For example, a fusion protein can comprise (a) an extracellular portion of a PDGFR, (b) an extracellular portion of a VEGFR, (c) a multimerization domain (e.g., an IgG1 Fc region), and at least one linker from the N-terminus to the C-terminus in an order selected from the group consisting of: (1) linker, a, linker, b, linker, c, linker; (2) a, linker, b, linker, c, linker; (3) linker, a, linker, b, linker, c; (4) a, linker, b, linker, c; (5) a, linker, b, c; and (6) a, b, linker, c. In another example, a fusion protein can comprise (a) an extracellular portion of a PDGFR, (b) a multimerization domain (e.g., an IgG1 Fc region), and at least one linker from the N-terminus to the C-terminus in an order selected from the group consisting of: (1) linker, a, linker, b, linker; (2) linker, a, linker, b; (3) a, b, linker; (4) a, linker, b; (5) linker, b, linker, a, linker; (6) linker, b, linker, a; (7) b, a, linker; and (8) b, linker, a.

Fusion Proteins

Provided herein are fusion proteins that have binding specificities to at least two different binding partners (e.g., PDGF and VEGF). In some embodiments, a fusion protein comprises a first binding specificity to a protein of the PDGF family (e.g., PDGF-A, PDGF-B, PDGF-C, or PDGF-D) and a second binding specificity to a VEGF (e.g., VEGF-A VEGF-B, VEGF-C, VEGF-D, or PlGF). In some embodiments, a fusion protein comprises a first binding specificity to a protein dimer of the PDGF family (e.g., PDGF-AA, PDGF-AB, PDGF-BB, PDGF-CC, or PDGF-DD) and a second binding specificity to a VEGF (e.g., VEGF-A VEGF-B, VEGF-C, VEGF-D, or PlGF). In some embodiments, a fusion protein comprises a first binding specificity to a mammalian (e.g., human) PDGF and a second binding specificity to a mammalian (e.g., human) VEGF. In some embodiments, a fusion protein binds to the same PDGF as any of the PDGFRs described herein. In some embodiments, a fusion protein binds to the same component of the PDGF pathway as any one of PDGFR-α or PDGFR-β. In some embodiments, a fusion protein binds to the same PDGF as any one of PDGFR-α/PDGFR-α, PDGFR-β/PDGFR-β, or PDGFR-α/PDGFR-β dimers. In some embodiments, a fusion protein comprises at least one extracellular portion of a PDGFR of any of the PDGFRs described herein. For example, a fusion protein can comprise at least one extracellular portion of PDGFR-α and at least one extracellular portion of PDGFR-β. In another example, a fusion protein can comprise two extracellular portions of PDGFR-β such as Ig-like domain D1-D3 and Ig-like domain D1-D5. In some aspects, a fusion protein comprises an extracellular portion of a PDGFR comprising the amino acid sequence selected from the group consisting of SEQ ID NOs:1-3. In some aspects, a fusion protein comprises an extracellular portion of a PDGFR comprising the amino acid sequence selected from the group consisting of SEQ ID NOs:7 and 8.

In some embodiments, a fusion protein binds to the same component of the VEGF pathway as any of the VEGFRs described herein. In some embodiments, a fusion protein binds to the same component of the VEGF pathway as any one of VEGFR1, VEGFR2, or VEGFR3. In some embodiments, a fusion protein comprises at least one extracellular portion of a VEGFR of any of the VEGFRs described herein. For example, a fusion protein can comprise at least one extracellular portion of VEGFR1 and at least one extracellular portion of VEGFR2. In another example, a fusion protein can comprise two extracellular portions of VEGFR1 such as Ig-like domain D2 and Ig-like domain D1-D3. In some aspects, a fusion protein comprises an extracellular portion of a VEGFR comprising the amino acid sequence selected from the group consisting of SEQ ID NOs:4 and 5. Any of the fusion proteins disclosed herein comprising an extracellular portion of a PDGFR and an extracellular portion of a VEGFR can further comprise a multimerization domain. In some embodiments, the multimerization domain is an Fc region (e.g., an IgG1 Fc region). In some embodiments, the Fc region comprises the amino acid sequence of SEQ ID NO:6. In some embodiments, the fusion protein comprising an extracellular portion of a PDGFR, an extracellular portion of VEGFR, and a multimerization domain inhibits the PDGF and VEGF signaling pathways (e.g., inhibition of PDGF and VEGF activity). Any of the fusion proteins disclosed herein comprising an extracellular portion of a PDGFR, an extracellular portion of VEGFR, and a multimerization domain can further comprise a linker. The linker can be any linker as disclosed herein. In some embodiments, the linker is a peptide linker. In some embodiments, the linker comprises the amino acid sequence selected from the group consisting of $Gly_9$, $Glu_9$, $Ser_9$, $Gly_5$-Cys-Pro$_t$-Cys, $(Gly_4$-Ser$)_3$, Ser-Cys-Val-Pro-Leu-Met-Arg-Cys-Gly-Gly-Cys-Cys-Asn, Pro-Ser-Cys-Val-Pro-Leu-Met-Arg-Cys-Gly-Gly-Cys-Cys-Asn, Gly-Asp-Leu-Ile-Tyr-Arg-Asn-Gln-Lys, and $Gly_9$-Pro-Ser-Cys-Val-Pro-Leu-Met-Arg-Cys-Gly-Gly-Cys-Cys-Asn. In some embodiments, the extracellular portion of a PDGFR comprises an extracellular portion of a mammalian (e.g., human) PDGFR. In some embodiments, the extracellular portion of a VEGFR comprises an extracellular portion of a mammalian (e.g., human) VEGFR. In some embodiments, a fusion protein comprises an extracellular portion of a human PDGFR (e.g., human PDGFR-β) and an extracellular portion of a human VEGFR (e.g., human VEGFR1).

In one aspect, the invention provides a fusion protein comprising: a) an extracellular portion of a PDGFR comprising the amino acid sequence of SEQ ID NO:1, 2, 3, 7, or 8; b) an extracellular portion of a VEGFR comprising the amino acid sequence of SEQ ID NO:4 or 5; and c) a multimerization domain comprising the amino acid sequence of SEQ ID NO:6. In some embodiments, the fusion protein comprises: a) an extracellular portion of a PDGFR comprising the amino acid sequence of SEQ ID NO:1; b) an extracellular portion of a VEGFR comprising the amino acid sequence of SEQ ID NO:4; and c) a multimerization domain comprising the amino acid sequence of SEQ ID NO:6. In some embodiments, the fusion protein comprises: a) an extracellular portion of a PDGFR comprising the amino acid sequence of SEQ ID NO:3; b) an extracellular portion of a VEGFR comprising the amino acid sequence of SEQ ID NO:4; and c) a multimerization domain comprising the amino acid sequence of SEQ ID NO:6.

Provided herein are fusion proteins comprising an extracellular portion of a PDGFR, an extracellular portion of a VEGFR, and a multimerization domain in a specific order. In some embodiments, the fusion protein comprises (a) an extracellular portion of a PDGFR, (b) an extracellular portion of a VEGFR, and (c) a Fc region arranged from the N-terminus to C-terminus in an order of a, b, c. In some of the embodiments, an extracellular portion of a PDGFR comprises the Ig-like domains D1-D3 of a PDGFR (e.g., PDGFR-β). In some embodiments, an extracellular portion of a PDGFR comprises the Ig-like domains D1-D4 of a PDGFR (e.g., PDGFR-β). In some embodiments, an extracellular portion of a PDGFR comprises the Ig-like domains D1-D5 of a PDGFR (e.g., PDGFR-β). In some embodiments, an extracellular portion of a VEGFR comprises the Ig-like domain D2 of a VEGFR (e.g., VEGFR1). In some embodiments, an extracellular portion of a VEGFR comprises the Ig-like domains D1-D3 of a VEGFR (e.g., VEGFR1). In some embodiments, a multimerization domain comprises the Fc region of an IgG1 antibody.

In some embodiments, the fusion protein comprises the amino acid sequence of SEQ ID NO:12. In other embodiments, the fusion protein comprises the amino acid sequence of SEQ ID NO:13. In still other embodiments, the fusion protein comprises the amino acid sequence of SEQ ID NO:14. In yet other embodiments, the fusion protein comprises the amino acid sequence of SEQ ID NO:15.

Fusion proteins comprising at least two or more extracellular portions of a PDGFR, two or more extracellular portions of a VEGFR, and/or two or more multimerization domains are also contemplated. For example, a fusion protein may comprise (a) an extracellular portion of a PDGFR, (b) an extracellular portion of a VEGFR, and (c) a Fc region arranged from the N-terminus to C-terminus in an order of a, a, b, c or in an order of a, b, b, c. Any combination of at least one extracellular portion of a PDGFR, at least one extracellular portion of a VEGFR, and at least one multimerization domain is provided herein as if each combination had been expressly stated herein.

Fusion proteins comprising an extracellular portion of a PDGFR and a multimerization domain are also contemplated. In some embodiments, the fusion protein comprises (a) an extracellular portion of a PDGFR and (b) a Fc region arranged from the N-terminus to C-terminus in an order of a and b. In some embodiments, the fusion protein comprises (a) an extracellular portion of a PDGFR and (b) a Fc region arranged from the N-terminus to C-terminus in an order of b and a. In some embodiments, an extracellular portion of a PDGFR comprises the Ig-like domains D1-D2 of a PDGFR (e.g., PDGFR-β). In some embodiments, an extracellular portion of a PDGFR comprises the Ig-like domains D1-D3 of a PDGFR (e.g., PDGFR-β). In some embodiments, an extracellular portion of a PDGFR comprises the Ig-like domains D1-D4 of a PDGFR (e.g., PDGFR-β). In some embodiments, an extracellular portion of a PDGFR comprises the Ig-like domains D1-D5 of a PDGFR (e.g., PDGFR-β). In some embodiments, a multimerization domain comprises the Fc region of an IgG1 antibody. Any combination of at least one extracellular portion of a PDGFR and at least one multimerization domain is provided herein as if each combination had been expressly stated herein.

In some embodiments, the fusion protein comprises the amino acid sequence of SEQ ID NO:9. In some embodiments, the fusion protein comprises the amino acid sequence of SEQ ID NO:10. In some embodiments, the fusion protein comprises the amino acid sequence of SEQ ID NO:11.

The fusion proteins described in the present invention can comprise modified forms of the extracellular portion of a PDGFR, the extracellular portion of a VEGFR, and/or the multimerization domain. For example, the fusion protein components can have post-translational modifications, including for example, glycosylation, sialylation, acetylation, and phosphorylation.

In some embodiments, amino acid sequence variants of the fusion proteins are provided herein. For example, it may be desirable to improve the binding affinity and/or other biological properties of the extracellular portion of a PDGFR, the extracellular portion of a VEGFR, and/or the multimerization domain. Amino acid sequence variants of the fusion protein may be prepared by introducing appropriate modifications into the nucleotide sequence encoding the extracellular portion of a PDGFR, the extracellular portion of a VEGFR, and/or the multimerization domain, or by introduction through peptide synthesis. Such modifications include, for example, deletions from, insertions into, and/or substitutions of residues within the amino acid sequences of the extracellular portion of a PDGFR, the extracellular portion of a VEGFR, and/or the multimerization domain. Any combination of deletion, insertion, and substitution can be made to arrive at the final construct, provided that the final construct possesses the desired characteristics (e.g., binding to a PDGF, binding to a VEGF, inhibiting activation of a PDGF pathway, multimer formation, and/or inhibiting activation of a VEGF pathway). In some embodiments, the fusion protein comprises at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence of a fusion protein comprising any extracellular portion of a PDGFR, extracellular portion of a VEGFR, and/or multimerization domain as disclosed herein. In some embodiments, a fusion protein variant comprises at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence selected from the group consisting of SEQ ID NOs:12-15. In some embodiments, a fusion protein variant comprises at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence selected from the group consisting of SEQ ID NOs:9-11.

Amino acid residue substitutions disclosed herein also include conservative substitutions. Conservative substitutions are shown in the Table 1 below under the heading of "conservative substitutions". If such substitutions result in a change in biological activity, then more substantial changes, denominated "exemplary substitutions" in Table 1, or as further described below in reference to amino acid classes, may be introduced and the products screened. Amino acid substitutions as shown in Table 1 or as described below in reference to the amino acid classes may be introduced into any of the fusion proteins or protein components (e.g., extracellular portion of a PDGFR, extracellular portion of a VEGFR, multimerization domain, etc.) provided herein.

TABLE 1

Potential amino acid substitutions

| Original Residue | Exemplary Substitutions | Conservative Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the proteins or polypeptides are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe;
(7) large hydrophobic: Norleucine, Met, Val, Leu, Ile.

Non-conservative substitutions entail exchanging a member of one of these classes for another class.

A useful method for identification of certain residues or regions of the fusion protein that are preferred locations for mutagenesis is called "alanine scanning mutagenesis" as described by Cunningham and Wells in Science, 1989, 244:1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the target binding partner. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed fusion polypeptide variants are screened for the desired activity.

Any cysteine residue not involved in maintaining the proper conformation of the fusion proteins or protein components (e.g., extracellular portion of a PDGFR, extracellular portion of a VEGFR, multimerization domain, etc.) also may be substituted, generally with serine, to improve the oxidative stability of the molecule and prevent aberrant crosslinking. Conversely, cysteine bond(s) may be added to the fusion protein or protein components (e.g., extracellular portion of a PDGFR, extracellular portion of a VEGFR, multimerization domain, etc.) to improve its stability.

In further embodiments, proteins or peptides of the invention may comprise one or more non-naturally occurring or modified amino acids. A "non-naturally occurring amino acid residue" refers to a residue, other than those naturally occurring amino acid residues listed above, which is able to covalently bind adjacent amino acid residues(s) in a polypeptide chain. Non-natural amino acids include, but are not limited to homo-lysine, homo-arginine, homo-serine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, citrulline, pentylglycine, pipecolic acid and thioproline. Modified amino acids include natural and non-natural amino acids which are chemically blocked, reversibly or irreversibly, or modified on their N-terminal amino group or their side chain groups, as for example, N-methylated D and L amino acids, side chain functional groups that are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide and a modified amino acid of alanine. Additional non-natural and modified amino acids, and methods of incorporating them into proteins and peptides, are known in the art (see, e.g., Sandberg et al., (1998) *J. Med. Chem.* 41: 2481-91; Xie and Schultz (2005) *Curr. Opin. Chem. Biol.* 9: 548-554; Hodgson and Sanderson (2004) *Chem. Soc. Rev.* 33: 422-430.

Amino acid sequence insertions include amino-("N") and/or carboxy-("C") terminal fusions ranging in length from one residue to a hundred or more residues, as well as intrasequence insertions of single or multiple amino acid residues. Examples of terminal insertions include a fusion protein with an N-terminal methionyl residue or the fusion protein fused to a cytotoxic polypeptide. Other insertional variants of the fusion protein molecule include fusion to the N- or C-terminus of the fusion protein a polypeptide that allows formation of protein multimers.

The present invention provides a signal peptide, also referred herein as a signal sequence, which can be a component of any fusion protein provided herein. For example, a fusion protein comprising an extracellular portion of a PDGFR, an extracellular portion of a VEGFR, and a multimerization domain may further comprise a heterologous peptide, preferably a signal sequence or other peptide having a specific cleavage site at the N-terminus of the mature fusion protein. The heterologous signal sequence selected preferably is one that is recognized and processed (i.e., cleaved by a signal peptidase) by eukaryotic host-cells. For prokaryotic host-cells that do not recognize and process native mammalian signal sequences, the eukaryotic (i.e., mammalian) signal sequence is replaced by a prokaryotic signal sequence selected, for example, from the group consisting of leader sequences from alkaline phosphatase, penicillinase, lpp, or heat-stable enterotoxin II genes. For yeast secretion the native signal sequence may be substituted by, e.g., the yeast invertase leader, factor leader (including *Saccharomyces* and *Kluyveromyces*-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex virus gD signal, are available. A signal peptide can be completely cleaved from the fusion protein as it is produced from host cells or it can be partially cleaved. A mixed population of fusion proteins can be produced from a host cell wherein fusion proteins comprise a completely cleaved signal sequence (e.g., no signal sequence), a partially cleaved signal sequence (e.g., portion of the signal sequence) and/or a non-cleaved signal sequence (e.g., complete signal sequence). For example, a fusion protein further comprising a signal peptide at the N-terminus can be cleaved at the N-terminus by any one of 1, 2, 3, 4, 5, 6, 7, 8, 9, 10, 11, 12, 13, 14, 15, 16, 17, 18, 19, 20, 21, or 22 amino acid residues. In some embodiments, any fusion protein described herein comprises a signal peptide for protein secretion from a cell. In some embodiments, any fusion protein described herein does not comprise a signal peptide for protein secretion from a cell.

The present invention provides a dimeric fusion protein comprising two fusion proteins, wherein each fusion protein comprises any fusion protein disclosed herein. In one embodiment, the dimeric fusion protein comprises two identical fusion proteins. In another embodiment, the dimeric fusion protein comprises two different fusion proteins. The fusion proteins disclosed herein may form multimers of two or more fusion proteins. Multimers (e.g., dimers, trimers, tetramers, etc.) can form from identical fusion proteins (e.g., homomultimer) or form heterologous fusion proteins (e.g., heteromultimer). In another embodiment, the multimeric fusion protein comprises at least one fusion protein comprising the amino acid sequence selected from the group consisting of SEQ ID NOs:12-15, or an amino acid sequence having at least 90% identity to the amino acid sequence selected from the group consisting of SEQ ID NOs:12-15. In another embodiment, the multimeric fusion protein comprises at least one fusion protein comprising the amino acid sequence selected from the group consisting of SEQ ID NOs:9-11, or an amino acid sequence having at least 90% identity to the amino acid sequence selected from the group consisting of SEQ ID NOs:9-11. In an embodiment, the fusion protein is recovered as a protein fusion multimer from a host cell comprising a nucleic acid encoding said fusion protein. In some embodiments, the fusion proteins are glycosylated. For example, the fusion protein may be glycosylated after release from a host cell at the extracellular portion of a PDGFR, the extracellular portion of a VEGFR, and/or multimerization domain.

Also provided herein are pharmaceutical compositions comprising a fusion protein of the invention and a pharmaceutically acceptable carrier. The pharmaceutical compositions may be suitable for a variety of modes of administration described herein, including for example systemic or localized administration. The pharmaceutical compositions can be in the form of eye drops, injectable solutions, or in a form suitable for inhalation (either through the mouth or the nose) or oral administration. In some embodiments, the pharmaceutical compositions comprising a fusion protein described herein and a pharmaceutically acceptable carrier is suitable for administration to human. In some embodiments, the pharmaceutical compositions comprising a fusion protein described herein and a pharmaceutically acceptable carrier is suitable for intravitreal injection or topical application to the eye. Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. The pharmaceutical composition may further comprise additional ingredients, for example preservatives, buffers, tonicity agents, antioxidants and stabilizers, nonionic wetting or clarifying agents, viscosity-increasing agents, and the like. The pharmaceutical compositions described herein can be packaged in single unit dosages or in multidosage forms. The compositions are generally formulated as sterile and substantially isotonic solution. Compositions can also be formulated to have osmotic values that are compatible with the aqueous humor of the eye and ophthalmic tissues. Such osmotic values will generally be in the range of from about 200 to about 400 milliosmoles per kilogram of water ("mOsm/kg"), but will preferably be about 300 mOsm/kg. The retina is considered to have an osmotic value of ~283 mOsm/kg.

IV. Nucleic Acids, Vectors, and Host Cells

Nucleic Acids

Provided herein are isolated nucleic acids encoding any of the fusion proteins components disclosed herein, such as an extracellular portion of a PDGFR, and extracellular portion of a VEGFR, and a multimerization domain. Nucleic acids encoding mammalian PDGFR have been described for both receptor types, PDGFR-α and PDGFR-β. Exemplary nucleic acid sequences can be found at, but are not limited to, Yarden et al., Nature, 1986, 323:226-232; Matsui et al., Science, 1989, 243: 800-803; U.S. patent application Ser. No. 07/771,829 which is a continuation of U.S. patent application Ser. No. 07/309,332, now abandoned, U.S. Pat. No. 5,686,572, and WO2006/113277. mRNA encoding human PDGFR-α and PDGFR-β can be found at Genbank Accession Nos. NM_006206.4 and NM_002609.3, respectively. In some embodiments, an isolated nucleic acid encodes an extracellular portion of a PDGFR comprising an amino acid sequence selected from the group consisting of SEQ ID NOs:1-3. In some embodiments, an isolated nucleic acid encodes an extracellular portion of a PDGFR comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence selected from the group consisting of SEQ ID NOs:1-3. In some embodiments, the isolated nucleic acid encoding an extracellular portion of a PDGFR is selected from the group consisting of SEQ ID NOs:16 and 17. Also provided herein are isolated nucleic acids encoding an extracellular portion of a VEGFR. Nucleic acids encoding mammalian VEGFR have been described for all receptor types. Exemplary nucleic acid sequences can be found at, but are not limited to, U.S. Pat. No. 7,928,072 and WO2006/113277. mRNA encoding human VEGFR1 and VEGFR2 can be found at Genbank Accession Nos. NM_001159920.1 and NM_002253.2, respectively. mRNA encoding human VEGFR3 can be found at Genbank Accession Nos. NM_002020.7 and NM_182925.4. In some embodiments, an isolated nucleic acid encodes an extracellular portion of a VEGFR comprising an amino acid sequence selected from the group consisting of SEQ ID NOs:4 and 5. In some embodiments, an isolated nucleic acid encodes an extracellular portion of a VEGFR comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence selected from the group consisting of SEQ ID NOs:4 and 5. Also provided herein are isolated nucleic acids encoding a multimerization domain (e.g., Fc region). In some embodiments, an isolated nucleic acid encodes a multimerization domain comprising an amino acid sequence of SEQ ID NO:6. In some embodiments, an isolated nucleic acid encodes a multimerization domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence selected from the group consisting of SEQ ID NO:6.

Also provided are isolated nucleic acids encoding a fusion protein as disclosed herein. In some embodiments, an isolated nucleic acid encodes a fusion protein comprising an amino acid sequence selected from the group consisting of SEQ ID NOs:12-15. In some embodiments, an isolated nucleic acid encodes a fusion protein comprising an amino acid sequence selected from the group consisting of SEQ ID NOs:9-11. In some embodiments, an isolated nucleic acid encodes a fusion protein comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence selected from the group consisting of SEQ ID NOs:12-15. In some embodiments, an isolated nucleic acid encodes a fusion protein comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence selected from the group consisting of SEQ ID NOs:9-11. In some embodiments, an isolated nucleic acid encoding a fusion protein comprises the nucleic acid sequence selected from the group consisting of SEQ ID NOs:21-24. In some embodiments, an isolated nucleic acid encoding a fusion protein comprises the nucleic acid sequence selected from the group consisting of SEQ ID NOs:18-20.

An isolated nucleic acid sequence encoding a fusion protein or a component of a fusion protein (e.g., the extracellular portion of a PDGFR, the extracellular portion of a VEGFR, or the multimerization domain) may further include a nucleic acid sequence encoding a linker. In some embodiments, a nucleic acid encodes a linker selected from the group consisting of Gly$_9$, Glu$_9$, Ser$_9$, Gly$_5$-Pro$_7$-Cys, (Gly$_4$-Ser)$_3$, Ser-Cys-Val-Pro-Leu-Met-Arg-Cys-Gly-Gly-Cys-Cys-Asn, Pro-Ser-Cys-Val-Pro-Leu-Met-Arg-Cys-Gly-Gly-Cys-Cys-Asn, Gly-Asp-Leu-Ile-Tyr-Arg-Asn-Gln-Lys, and Gly$_9$-Pro-Ser-Cys-Val-Pro-Leu-Met-Arg-Cys-Gly-Gly-Cys-Cys-Asn.

Isolated nucleic acids may further include a sequence encoding a signal peptide that serves as a signal sequence to secrete the fusion protein from the host cells. In some embodiments, the isolated nucleic acid does not comprise a sequence encoding a signal peptide.

Isolated nucleic acid molecules encoding a fusion protein or a component of a fusion protein (e.g., the extracellular portion of a PDGFR, the extracellular portion of a VEGFR, or the multimerization domain) can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand. The isolated nucleic acids can be obtained from biological sources using any number of cloning methodologies known to those of skill in the art. The isolated nucleic acids can also be prepared by direct chemical synthesis by known methods. Nucleic acids encoding a fusion protein or fusion protein component (e.g., the extracellular portion of a PDGFR, the extracellular portion of a VEGFR, or the multimerization domain) can be prepared by a variety of methods known in the art including, but not limited to, isolation from a natural source or preparation by oligonucleotide-mediated mutagenesis, site-directed mutagenesis, PCR mutagenesis, and cassette mutagenesis of an earlier prepared variant or a non-variant version of the fusion protein or fusion protein component. See *Molecular Cloning: A Laboratory Manual* (Sambrook et al., 4$^{th}$ ed., Cold Spring Harbor Laboratory Press, Cold Spring Harbor, N.Y., 2012) and *Current Protocols in Molecular Biology* (F. M. Ausubel, et al. eds., 2003).

Vectors

The present invention contemplates the use of a nucleic acid delivery vehicle for introduction of one or more nucleic acid sequences encoding for a fusion protein or fusion protein component into a cell for expression of said protein. Examples of nucleic acid delivery vehicles are liposomes, biocompatible polymers, including natural polymers and synthetic polymers; lipoproteins; polypeptides; polysaccharides; lipopolysaccharides; artificial viral envelopes; metal particles; and bacteria, viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts. In some embodiments, the nucleic acid delivery vehicle is an expression vector such as a plasmid. The vector may include any element to establish a conventional function of an expression vector, for example, a promoter, ribosome binding element, terminator, enhancer, selection marker, and origin of replication. The promoter can be a constitutive, inducible or repressible promoter. Exemplary promoters include, but are not limited to, the cytomegalovirus (CMV) immediate early promoter, the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken beta-actin/Rabbit β-globin promoter (CAG promoter; Niwa et al., *Gene,* 1991, 108(2):193-9) and the elongation factor 1-alpha promoter (EF1-alpha) promoter (Kim et al., *Gene,* 1990, 91(2):217-23 and Guo et al., *Gene Ther.,* 1996, 3(9):802-10). A number of expression vectors capable of delivering nucleic acids to a cell (e.g., bacterial cell, yeast cell, plant cell, or mammalian cell) are known in the art and may be used herein for production of a fusion protein or fusion protein component in the cell. For example, *E. coli* can be used to produce a fusion protein if transformed with a plasmid, such as pBR322 (Mandel et al., *J. Mol. Biol.,* 1970, 53:154), engineered to comprise a nucleic acid encoding the fusion protein. Expressed fusion proteins or fusion protein components can be harvested from the cells and purified according to conventional techniques known in the art and as described herein.

Host Cells

Provided herein are host cells comprising a nucleic acid encoding a fusion protein described herein. Nucleic acids encoding fusion proteins or fusion protein components (e.g., an extracellular portion of a PDGFR, an extracellular portion of a VEGFR, and/or a multimerization domain) can be provided to a target cell by any means known in the art. In some embodiments, the nucleic acid encoding a protein of interest (e.g., a fusion protein) is in a viral vector and the vector has been packaged, then the virions can be used to infect cells. In some embodiments, the nucleic acid encoding a protein of interest (e.g., a fusion protein) is in an expression vector such as a plasmid. Transfection or transformation procedures as are appropriate for the particular cells can be used for introducing a nucleic acid encoding a protein of interest (e.g., fusion protein) into a target cell. Formulations utilizing polymers, liposomes, or nanospheres can be used for delivery of nucleic acids encoding a protein of interest (e.g., a fusion protein). Cells which can be transformed or transfected with recombinant constructs according to the invention may be any which are convenient to one of skill in the art. Exemplary cell types which may be used include bacteria, yeast, fungi, insect, plant, and mammalian cells. Exemplary mammalian cells which may be used include, but are not limited to, fibroblasts, hepatocytes, endothelial cells, stem cells, hematopoietic cells, epithelial cells, myocytes, neuronal cells, and keratinocytes. Additional exemplary mammalian cell lines that can be used include, but are not limited to, COS cells, VERO cells, HeLa cells, Chinese hamster ovary (CHO) cells, 293 cells, NSO cells, SP20 cells, 3T3 fibroblast cells, W138 cells, BHK cells, HEPG2 cells, DUX cells and MDCK cells. These cells can be used to produce and harvest the protein of interest. In some embodiments, transformed or transfected cells can be provided to a cell or mammalian host. Suitable cells for delivery to a cell or mammalian host include any mammalian cell type from any organ, tumor, or cell line. For example, human, murine, goat, ovine, bovine, dog, cat, and porcine cells can be used.

The term "host cell" includes a cell which has been or can be a recipient for a vector(s) of this invention and the progeny thereof. The progeny may not necessarily be completely identical (in morphology or in genomic of total DNA complement) to the original parent cell due to natural, accidental, or deliberate mutation. Host cells are preferably eukaryotic cells, preferably mammalian cells, most preferably human cells.

V. Methods of Producing Fusion Proteins and Fusion Protein Components

Provided herein are methods for producing fusion proteins or fusion protein components (e.g., an extracellular portion of a PDGFR, an extracellular portion of a VEGFR, and/or a multimerization domain) of the invention as disclosed herein. In some aspects, a method is provided for producing any fusion protein as disclosed herein comprising culturing a host cell comprising a nucleic acid encoding any of the fusion proteins disclosed herein under a condition that produces the fusion protein, and recovering the fusion protein produced by the host cell. In some embodiments, a nucleic acid encoding a fusion protein is selected from the group consisting of SEQ ID NOs:18-24.

(1) Culturing the Host Cells

Cells used to produce the fusion proteins or fusion protein components (e.g., an extracellular portion of a PDGFR, an extracellular portion of a VEGFR, and/or a multimerization domain) of the invention are grown in media known in the art and suitable for culture of the selected host cells.

Examples of suitable media include Ham's F10 (Sigma), Minimal Essential Medium (MEM, Sigma), RPMI 1640 (Sigma), Dulbecco's Modified Eagle's Medium (DMEM, Sigma), and Luria Broth (LB). In addition, any of the media described in Ham et al., *Meth. Enz.* 58:44 (1979), Barnes et al., *Anal. Biochem.* 102:255 (1980), U.S. Pat. No. 4,767,704; 4,657,866; 4,927,762; 4,560,655; or 5,122,469; WIPO Publication Nos. WO 90/03430; WO 87/00195; or U.S. Pat. Re. 30,985 may be used as culture media for the cells. A given medium is generally supplemented as necessary with hormones and/or other growth factors (such as insulin, transferrin, or epidermal growth factor), DHFR, salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH, and the like, are those previously used with the cell selected for expression, and will be apparent to one of skill in the art. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0. If an inducible promoter is used in the expression vector, protein expression is induced under conditions suitable for the activation of the promoter. For example, if a PhoA promoter is used for controlling transcription, the transformed host cells may be cultured in a phosphate-limiting medium for induction. A variety of other inducers may be used, according to the vector construct employed, as is known in the art.

(2) Purification of Fusion Proteins or Fusion Protein Components

When using recombinant techniques, the fusion proteins or fusion protein components (e.g., an extracellular portion of a PDGFR, an extracellular portion of a VEGFR, and/or a multimerization domain) described herein can be produced intracellularly, in the periplasmic space, or secreted directly into the medium. If the polypeptides are produced intracellularly, as a first step, protein recovery typically involves disrupting the cell, generally by such means as osmotic shock, sonication or lysis. Once cells are disrupted, particulate debris from either host cells or lysed fragments is removed, for example, by centrifugation or ultrafiltration. Where the polypeptides are secreted into the medium, supernatants from such expression systems are generally first filtered and concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

Compositions of fusion proteins or fusion protein components (e.g., an extracellular portion of a PDGFR, an extracellular portion of a VEGFR, and/or a multimerization domain) prepared from such cells can be purified using, for example, hydroxylapatite chromatography, gel electrophoresis, dialysis, and affinity chromatography. In some embodiments, protein A or protein G is used as an affinity ligand for use in affinity chromatography. The suitability of protein A as an affinity ligand depends on the species and isotype of any immunoglobulin Fc region that is present in the fusion proteins (Lindmark et al., *J. Immunol. Meth.* 62:1-13 (1983). In some embodiments, protein A is used as an affinity ligand for isolating and purifying fusion proteins or fusion protein components (e.g., an extracellular portion of a PDGFR, an extracellular portion of a VEGFR, and/or a multimerization domain) as described herein. In some embodiments, protein G is used as an affinity ligand for isolating and purifying fusion proteins or fusion protein components (e.g., an extracellular portion of a PDGFR, an extracellular portion of a VEGFR, and/or a multimerization domain) as described herein. The matrix to which the affinity ligand is attached is most often agarose, but other matrices are available. Mechanically stable matrices such as controlled pore glass or poly(styrene-divinyl)benzene allow for faster flow rates and shorter processing times than can be achieved with agarose. Other techniques for protein purification, such as fractionation on an ion-exchange column, ethanol precipitation, Reverse Phase HPLC, chromatography on silica, heparin, SEPHAROSE™, or anion or cation exchange resins (such as a polyaspartic acid column), as well as chromatofocusing, SDS-PAGE, and ammonium sulfate precipitation are also available depending on the fusion proteins or fusion protein components (e.g., an extracellular portion of a PDGFR, an extracellular portion of a VEGFR, and/or a multimerization domain) to be recovered. In some embodiments, the recovered fusion protein is substantially pure. In a further embodiment, the recovered fusion protein is at least any of 90%, 91%, 92%, 93%, 94%, 95%, 96%, 97%, 98%, or 99% pure. Following any preliminary purification step or steps, the mixture comprising the fusion proteins or fusion protein components (e.g., an extracellular portion of a PDGFR, an extracellular portion of a VEGFR, and/or a multimerization domain) of interest and contaminants may be subjected to low pH hydrophobic interaction chromatography using an elution buffer at a pH between about 2.5-4.5, preferably performed at low salt concentrations (e.g., from about 0-0.25 M salt).

In general, various methodologies for preparing fusion proteins or fusion protein components (e.g., an extracellular portion of a PDGFR, an extracellular portion of a VEGFR, and/or a multimerization domain) for use in research, testing, and clinical applications are well-established in the art, consistent with the above-described methodologies and/or as deemed appropriate by one skilled in the art for a particular fusion proteins or fusion protein components of interest.

(3) Biological Activities of Fusion Proteins or Fusion Protein Components

Proteins may be purified and identified using commonly known methods such as fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins, ligand affinity using a suitable binding partner immobilized on a matrix, centrifugation, ELISA, BIACore, Western blot assay, amino acid and nucleic acid sequencing, and biological activity.

The fusion proteins or fusion protein components disclosed herein may be characterized or assessed for biological activities including, but not limited to, affinity to a target binding partner (e.g., a PDGF and/or VEGF family protein), competitive binding (e.g., blocking of target binding partner to PDGFR or VEGFR), inhibitory activity (e.g., inhibition of PDGF or VEGF pathway activation), inhibition of cell proliferation, inhibition of tumor growth, and inhibition of angiogenesis (e.g., choroidal neovascularization). In some embodiments, the fusion proteins or fusion protein components disclosed herein can be assessed for biological activity in vivo or in vitro. In any of the assays described herein, the assay is performed at a temperature of 4° C., 20-28° C. (e.g., 25° C.), or 37° C.

The fusion proteins or fusion protein components disclosed herein can be assessed for affinity to a binding partner such as a PDGF family protein (e.g., PDGF-A, PDGF-B, PDGF-C, or PDGF-D), a dimer of a PDGF family protein (e.g., PDGF-AA, PDGF-AB, PDGF-BB, PDGF-CC, or PDGF-DD) or a VEGF family protein (e.g., VEGF-A VEGF-B, VEGF-C, VEGF-D or PlGF). Many methods for assessing binding affinity are known in the art and can be used to identify the binding affinities of fusion proteins or fusion protein components to a binding partner. Binding affinities can be expressed as dissociation constant (Kd) values or half maximal effective concentration (EC50) values. Techniques for determining binding affinities (e.g., Kd values) are well known in the art such as Enzyme-Linked Immunosorbent Assay (ELISA) and BIAcore. See Harlow and Lane, *Antibodies: A Laboratory Manual*, CSH Publications, N Y (1988); Ausubel et al., *Current Protocols in Molecular Biology*, John Wiley & Sons, New York, (2009); Altschuh et al., *Biochem.*, 31:6298 (1992); and the BIAcore method disclosed by Pharmacia Biosensor, all of which are incorporated herein by reference. For example, binding affinities of the fusion proteins to a binding partner can be determined using ELISA. In some embodiments, binding of fusion proteins to PDGF-BB is assayed using ELISA. In this exemplary assay, secreted fusion proteins were serially diluted, mixed with human PDGF BB ligand at a 20 pM final concentration and incubated overnight at room temperature on an orbital shaker platform. After incubation, the amount of unbound PDGF-BB is measured by a human PDGF-specific ELISA (Human PDGF-BB DuoSet Product #DY220, R&D Systems). Statistical significance in binding affinities is analyzed using Prism 5.0d (GraphPad Software, Inc) and was calculated using the 2-way ANOVA test followed by Bonferroni correction. In a further example, binding of a fusion protein to a VEGF family protein is assayed using ELISA. In an exemplary assay, secreted fusion proteins are serially diluted, mixed with human VEGF at a 20 pM final concentration and incubated overnight at room temperature on an orbital shaker platform. The amount of unbound VEGF is then measured by a human VEGF-specific ELISA (Human VEGF Quantikine ELISA kit Cat# DVE00, R&D Systems).

In any of the embodiments herein, a fusion protein has an EC50 of ≤≤100 nM, ≤10 nM, ≤1 nM, ≤0.1 nM, ≤0.01 nM, or ≤0.001 nM (e.g., $10^{-8}$M or less, e.g., from $10^{-8}$M to $10^{-13}$M, e.g., from $10^{-9}$M to $10^{-13}$ M) for inhibition of an activity (e.g., inhibition of PDGF activity and/or VEGF activity). In any of the embodiments herein, a fusion protein has a Kd for a binding partner (e.g., PDGF and/or VEGF) of less than about any of about 1.0 mM, 500 μM, 100 μM, 50 μM, 25 μM, 10 μM, 900 nM, 800 nM, 700 nM, 600 nM, 500 nM, 400 nM, 350 nM, 300 nM, 250 nM, 200 nM, 150 nM, 100 nM, 95 nM, 90 nM, 85 nM, 80 nM, 75 nM, 70 nM, 65 nM, 60 nM, 55 nM, 50 nM, 45 nM, 40 nM, 35 nM, 30 nM, 25 nM, 20 nM, 15 nM, 10 nM, 5 nM, 1 nM, 900 pM, 800 pM, 700 pM, 600 pM, 500 pM, 400 pM, 300 pM, 200 pM, 100 pM, 50 pM, 25 pM, 12.5 pM, 6.25 pM, 5 pM, 4 pM, or 3 pM, inclusive, including any values in between these numbers. In some embodiments, the fusion protein variants described herein bind to a binding partner with a higher affinity compared to the binding affinity of a wild-type fusion protein described herein. In some aspects, the fusion protein variant binds to a binding partner with at least any of 10, 20, 30, 40, 50, 60, 70, 80, 90, 100, 200, 300, 400, 500, 600, 700, 800, 900, 1000, 1500, 2000, 2500, 3000, 3500, 4000, 4500, 5000, 6000, 7000, 8000, 9000, or 10,000, inclusive, including any value in between these numbers, higher fold affinity compared to the binding of the binding partner by a fusion protein comprising the amino acid sequence selected from the group consisting of SEQ ID NOs:9-15.

In some embodiments, the fusion proteins disclosed herein can be assessed for anti-proliferative activities such as reduction of cell proliferation. Many methods for assessing anti-proliferative properties for a fusion protein are known in the art. In one exemplary assay, human umbilical vein endothelial cells (HUVECs) can be used to demonstrate inhibition of VEGF-dependent and/or PDGF-dependent cell proliferation by a fusion protein described herein. In this assay, the fusion protein is applied to HUVECs in the presence of VEGF and/or PDGF and cell proliferation is measure. For example, HUVECs (HUVEC—Cambrex Bio Science Walkersville, Inc) are seeded in a 96 well plate at a density of 2,000 cells/well in Media 199 (Invitrogen) supplemented with 5% Fetal Bovine Serum (Invitrogen) and settled overnight. After incubation, the media is replaced with Media 199 (Invitrogen) supplemented with 5% Fetal Bovine Serum (Invitrogen) containing an equal volume (5 μl) of harvested cell culture and recombinant hVEGF-165 ligand alone at a final concentration of 10 ng/ml (R&D Systems Cat#293-VE), or in combination with PDGF-BB ligand at a final concentration of 20 ng/ml (R&D Systems Cat#220-BB) in a final volume of 100 μl per well. Cells are incubated at 37° C. in 5% $CO_2$ for three to four days. Cell Titer 96 $AQ_{ueous}$ One Solution Reagent (Promega Cat# G3580) is added at 20 μl/well and absorbance at 490 nm is taken four hours later to determine inhibition of cell proliferation by the fusion protein. In some embodiments, anti-angiogenic properties for a fusion protein are measured using techniques well known in the art. In an exemplary assay, an animal model of wet age-related macular degeneration is used to assay inhibition of neovascularization in the eye by the fusion protein. In this assay, the eyes of normal adult mouse is treated with a single intravitreal injection of a fusion protein or an rAAV particle comprising a nucleic acid encoding a fusion protein into the left eye (OS) on study day 0 while the right eye (OD) is left naïve to treatment. CNV is induced in both eyes using a laser (e.g., 3 burns placed per eye. 200 mW power, 50 μm spot, 100 ms) on study day 28. Mice are perfused with FITC-Dextran and euthanized on study day 42. The eyes are collected, fixed in 10% neutral buffered formalin and choroidal flatmounts are subsequently prepared in order to examine the extent of neovascularization. The number of burns without CNV in the treated (OS) eye is compared to the contralateral (OD) eye to determine the efficacy of the fusion protein. See, e.g., Example 5.

VI. Viral Particles and Methods of Producing Viral Particles

Also provided herein are viral particles comprising a nucleic acid encoding a fusion protein described herein. Viral vectors can be used for delivery of a nucleic acid encoding a fusion protein or fusion protein component for expression of the protein in a target cell within a particular target tissue (e.g., a diseased tissue). Many species of virus are known, and many have been studied for purposes of delivering nucleic acids to target cells. The exogenous nucleic acid can be inserted into a vector such as adenovirus, partially-deleted adenovirus, fully-deleted adenovirus, adeno-associated virus (AAV), retrovirus, lentivirus, and so forth for delivery to a cell. In some embodiments, the cell is in an individual and the virus is delivered via an intravenous, intramuscular, intraportal or other route of administration. The most commonly used viral vectors include those derived from adenoviruses, adeno-associated viruses (AAV) and retroviruses, including lentiviruses, such as human immunodeficiency virus (HIV). For exemplary viral vectors see U.S. Pat. No. 7,928,072 and WO2006/113277, both of which are incorporated herein by reference in their entirety.

In some embodiments, the viral particle is a recombinant AAV particle comprising a nucleic acid comprising one or two AAV ITRs and a sequence encoding a fusion protein described herein flanked by one or two ITRs. The nucleic acid is encapsidated in the AAV particle. The AAV particle also comprises capsid proteins. In some embodiments, the nucleic acid comprises operatively linked components in the direction of transcription, control sequences including transcription initiation and termination sequences, and the protein coding sequence(s) of interest (e.g., nucleic acid encoding a fusion protein). These components are flanked on the 5' and 3' end by functional AAV ITR sequences. By "functional AAV ITR sequences" it is meant that the ITR sequences function as intended for the rescue, replication and packaging of the AAV virion. See Davidson et al., *PNAS*, 2000, 97(7)3428-32; Passini et al., *J. Virol.*, 2003, 77(12):7034-40; and Pechan et al., *Gene Ther.*, 2009, 16:10-16, all of which are incorporated herein in their entirety by reference. For practicing some aspects of the invention, the recombinant vectors comprise at least all of the sequences of AAV essential for encapsidation and the physical structures for infection by the rAAV. AAV ITRs for use in the vectors of the invention need not have a wild-type nucleotide sequence (e.g., as described in Kotin, *Hum. Gene Ther.*, 1994, 5:793-801), and may be altered by the insertion, deletion or substitution of nucleotides or the AAV ITRs may be derived from any of several AAV serotypes. More than 40 serotypes of AAV are currently known, and new serotypes and variants of existing serotypes continue to be identified. See Gao et al., *PNAS*, 2002, 99(18): 11854-6; Gao et al., *PNAS*, 2003, 100(10):6081-6; and Bossis et al., *J. Virol.*, 2003, 77(12):6799-810. Use of any AAV serotype is considered within the scope of the present invention. In some embodiments, a rAAV vector is a vector derived from an AAV serotype, including without limitation, AAV1, AAV2, AAV3, AAV4, AAV5, AA6, AAV7, AAV8, AAV9, AAVrh.8, and AAVrh.10. In some embodiments, the nucleic acid in the AAV comprises an ITR of AAV1, AAV2, AAV3, AAV4, AAV5, AA6, AAV7, AAV8, AAV9, AAVrh.8, or AAVrh.10. In some embodiments, a nucleic acid encoding a fusion protein selected from the group consisting of SEQ ID NOs:12-15 is flanked by at least one AAV ITR. In some embodiments, the nucleic acid is selected from the group consisting of SEQ ID Nos:21-24. In further embodiments, the rAAV particle comprises capsid proteins of AAV1, AAV2, AAV3, AAV4, AAV5, AA6, AAV7, AAV8, AAV9, AAVrh.8, or AAVrh.10.

Different AAV serotypes are used to optimize transduction of particular target cells or to target specific cell types within a particular target tissue (e.g., a diseased tissue). A rAAV particle can comprise viral proteins and viral nucleic acids of the same serotype or a mixed serotype. For example, a rAAV particle can comprise AAV2 capsid proteins and at least one AAV2 ITR or it can comprise AAV2 capsid proteins and at least one AAV1 ITR. In another example, a rAAV particle can comprise AAV1 capsid proteins and at least one AAV2 ITR. In yet another example, a rAAV particle can comprise capsid proteins from both AAV1 and AAV2, and further comprise at least one AAV2 ITR. Any combination of AAV serotypes for production of a rAAV particle is provided herein as if each combination had been expressly stated herein.

The rAAV particles can be produced using methods know in the art. See, e.g., U.S. Pat. Nos. 6,566,118, 6,989,264, 6,995,006. In practicing the invention, host cells for producing rAAV particles include mammalian cells, insect cells, plant cells, microorganisms and yeast. Host cells can also be packaging cells in which the AAV rep and cap genes are stably maintained in the host cell or producer cells in which the AAV vector genome is stably maintained. Exemplary packaging and producer cells are derived from 293, A549 or HeLa cells. AAV vectors are purified and formulated using standard techniques known in the art.

In some aspects, a method is provided for producing any rAAV particle as disclosed herein comprising (a) culturing a host cell under a condition that rAAV particles are produced, wherein the host cell comprises (i) one or more AAV package genes, wherein each said AAV packaging gene encodes an AAV replication or encapsidation protein; (ii) an rAAV pro-vector comprising a nucleic acid encoding any fusion protein disclosed herein flanked by at least one AAV ITR, and (iii) an AAV helper function; and (b) recovering the rAAV particles produced by the host cell. In some embodiments, a nucleic acid encodes a fusion protein selected from the group consisting of SEQ ID NOs:12-15. In some embodiments, said at least one AAV ITR is selected from the group consisting of AAV1, AAV2, AAV3, AAV4, AAV5, AA6, AAV7, AAV8, AAV9, AAVrh.8, and AAVrh.10 ITR. In some embodiments, said encapsidation protein is selected from the group consisting of AAV1, AAV2, AAV3, AAV4, AAV5, AA6, AAV7, AAV8, AAV9, AAVrh.8, and AAVrh.10 capsid protein. In a further embodiment, the rAAV particles are purified. The term "purified" as used herein includes a preparation of rAAV particles devoid of at least some of the other components that may also be present where the rAAV particles naturally occur or are initially prepared from. Thus, for example, isolated rAAV particles may be prepared using a purification technique to enrich it from a source mixture, such as a culture lysate or production culture supernatant. Enrichment can be measured in a variety of ways, such as, for example, by the proportion of DNase-resistant particles (DRPs) present in a solution, or by infectivity, or it can be measured in relation to a second, potentially interfering substance present in the source mixture, such as contaminants, including production culture contaminants or in-process contaminants, including helper virus, media components, and the like.

Also provided herein are pharmaceutical compositions comprising a rAAV particle comprising a nucleic acid encoding a fusion protein of the invention and a pharmaceutically acceptable carrier. The pharmaceutical compositions may be suitable for a variety of modes of administration described herein, including for example systemic or localized administration. A pharmaceutical composition of a rAAV comprising a nucleic acid encoding a fusion protein described herein can be introduced systemically, e.g., by intravenous injection, by catheter, see U.S. Pat. No. 5,328, 470, or by stereotactic injection, Chen et al., 1994, PNAS, 91: 3054-3057. The pharmaceutical compositions can be in the form of eye drops, injectable solutions, or in a form suitable for inhalation or oral administration. In some embodiments, the pharmaceutical compositions comprising a fusion protein described herein and a pharmaceutically acceptable carrier is suitable for administration to human. In some embodiments, the pharmaceutical compositions comprising a fusion protein described herein and a pharmaceutically acceptable carrier is suitable for intravitreal injection or topical application to the eye. Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. The pharmaceutical composition may further comprise additional ingredients, for example preservatives, buffers, tonicity agents, antioxidants and stabilizers, nonionic wetting or clarifying agents, viscosity-increasing agents, and the like. The pharmaceutical compositions described herein can be packaged in single unit dosages or in multidosage forms. The compositions are generally formulated as sterile and substantially isotonic solution. Compositions can also be formulated to have osmotic values that are compatible with the aqueous humor of the eye and ophthalmic tissues. Such osmotic values will generally be in the range of from about 200 to about 400 mOsm/kg, but will preferably be about 300 mOsm/kg. Ophthalmic solutions useful for storing and/or delivering expression vectors or viral vectors have been disclosed, for example, in WO03077796A2.

VII. Methods of Treatment Using Fusion Proteins and Viral Particles

The methods of the present invention use any fusion protein disclosed herein. In some embodiments, the fusion protein binds a PDGF protein or a VEGF protein. In some embodiments, the fusion protein binds a PDGFR protein and a VEGFR protein. The fusion proteins described herein may have one or more of the following characteristics: (a) bind one or more proteins of the PDGF family such as PDGF-A, PDGF-B, PDGF-C, or PDGF-D; (b) bind one or more proteins of the VEGF family such as VEGF-A, VEGF-B, VEGF-C, VEGF-D, or PlGF; (c) block binding of a PDGF family protein to a PDGF receptor; (d) block binding of a VEGF family protein to a VEGF receptor; (e) inhibit activation of the PDGF signaling pathway and/or VEGF signaling pathway; (f) treat and/or prevent a disease such as an ocular disease, autoimmune disease, inflammatory disease, or cancer. The activities of fusion proteins may be measured in vitro and/or in vivo.

The present invention provides methods of treating a disease (such as an ocular disease, an inflammatory disease, an autoimmune disease, or cancer) by administering an effective amount of any fusion protein described herein to an individual. In some embodiments, a method of treating a disease comprises administering an effective amount of a composition comprising the fusion protein to an individual. In some embodiments, a method of treating a disease comprises administering an effective amount of a rAAV comprising a nucleic acid encoding the fusion protein to an individual. Methods of treating or preventing one or more aspects or symptoms of a disease (such as an ocular disease, an inflammatory disease, an autoimmune disease, or cancer) by administering an effective amount of any fusion protein described herein to an individual are also provided. In some embodiments, a method of treating or preventing one or more aspects or symptoms of a disease comprises administering an effective amount of a composition comprising the fusion protein to an individual. In some embodiments, a method of treating or preventing one or more aspects or symptoms of a disease comprises administering an effective amount of a rAAV comprising a nucleic acid encoding the fusion protein to an individual.

The methods described herein can be used for the treatment of a variety of diseases, including, but not limited to, inflammatory disease, ocular disease, autoimmune disease, or cancer. In some embodiments, the disease to be treated includes, but is not limited to, rheumatoid arthritis, inflammatory arthritis, osteoarthritis, cancer, age-related macular degeneration (AMD) (such as wet AMD or dry AMD), ocular disease characterized by neovascularization (such as choroidal neovascularization), uveitis (such as anterior uveitis or posterior uveitis), retinitis pigmentosa, and diabetic retinopathy.

In certain embodiments, the methods and compositions of the invention can be used to treat an autoimmune disease. In some embodiments, the autoimmune disease is rheumatoid arthritis, multiple sclerosis, or systemic lupus erythematosus. Rheumatoid arthritis (RA) is a chronic autoimmune disease that leads to inflammation of the joints. While RA principally affects synovial joints, it can affect surrounding tissues and organs. The pathology of RA involves an inflammatory process that can lead to the destruction of cartilage and the ankylosis (fusion) of joints. Other pathological manifestations of RA include vasculitis (inflammation of the blood vessels), which can affect nearly any organ system and can cause additional complications, including polyneuropathy, cutaneous ulceration, and visceral infarction. Pleuropulmonary manifestations include pleuritis, interstitial fibrosis, Caplan's syndrome, pleuropulmonary nodules, pneumonitis, rheumatoid lung disease and arteritis. Other manifestations include the development of inflammatory rheumatoid nodules on a variety of periarticular structures such as extensor surfaces, as well as on pleura and meninges. Weakness and atrophy of skeletal muscle are common.

In certain embodiments, the methods and compositions of the invention can be used to treat an inflammatory disease. In some embodiments, the inflammatory disease is inflammatory arthritis, osteoarthritis, psoriasis, chronic inflammation, irritable bowel disease, lung inflammation or asthma Inflammatory arthritis refers to inflammation of the joints that can result from an autoimmune disease such as, e.g., ankylosing spondylitis, juvenile idiopathic arthritis, mixed connective tissue disease, psoriatic arthritis, reactive arthritis, scleroderma, Sjogren's Syndrome, Still's Disease, and systemic lupus erythematosus. Inflammatory arthritis can also be caused by certain types of bacteria (such as with reactive arthritis) or by deposits of crystalline structures in the joints (such as with gout and pseudogout). The characteristic symptoms of inflammatory arthritis are pain and swelling of one or more joints, which may be warmer than the other joints. Stiffness of the joints following prolonged inactivity (such as in the morning or after sitting for a length of time) is a very common symptom. Patients with inflammatory arthritis usually have multiple joint complaints. Osteoarthritis, also known as degenerative arthritis or degenerative joint disease, is a group of mechanical abnormalities involving degradation of joints, including articular cartilage and subchondral bone. Symptoms may include joint pain, tenderness, stiffness, locking, and sometimes an effusion (i.e., the presence of increased intra-articular fluid). A variety of causes, e.g., hereditary, developmental, metabolic, obesity-related, and mechanical, may initiate processes leading to loss of cartilage. As breakdown products from the cartilage are released into the synovial space, the cells lining the joint attempt to remove them. New bone outgrowths, or "spurs" can form. Often, when bone becomes less well protected by cartilage, bone may be exposed and damaged. These bone changes, in combination with inflammation of the joint, cause pain. As a result of decreased movement secondary to pain, regional muscles may atrophy, and ligaments may become more lax.

Persistent and unregulated angiogenesis occurs in a multiplicity of disease states such as cancer. In cancer, cells divide and grow uncontrollably, forming malignant tumors, which vascularize and invade nearby parts of the body. The cancer may also spread (metastasize) to more distant parts of the body through the lymphatic system or bloodstream. The causes of cancer can be environmental (due to exposure to chemicals, radiation or due to lifestyle), hereditary, or infectious. In some embodiments, the methods and compositions of the invention can be used to treat cancer. In some embodiments, the cancer is prostate cancer, breast cancer, lung cancer, esophageal cancer, colon cancer, rectal cancer, liver cancer, urinary tract cancer (e.g., bladder cancer), kidney cancer, lung cancer (e.g., non-small cell lung cancer), ovarian cancer, cervical cancer, endometrial cancer, pancreatic cancer, stomach cancer, thyroid cancer, skin cancer (e.g., melanoma), hematopoietic cancers of lymphoid or myeloid lineage, head and neck cancer, nasopharyngeal carcinoma (NPC), glioblastoma, teratocarcinoma, neuroblastoma, adenocarcinoma, cancers of mesenchymal origin such as a fibrosarcoma or rhabdomyosarcoma, soft tissue sarcoma and carcinoma, choriocarcinioma, hepatoblastoma, Karposi's sarcoma or Wilm's tumor.

Other diseases that are associated with angiogenesis can be treated with the methods and compositions disclosed herein. These diseases include atherosclerosis, retrolental fibroplasia, thyroid hyperplasias (including grave's disease), nephrotic syndrome, preclampasia, ascites, pericardial effusion (such as associated with pericarditis) and pleural effusion.

In some embodiments, the methods and compositions of the invention can be used to treat an ocular disease. In some embodiments, the ocular disease is AMD such as wet AMD or dry AMD, uveitis, retinitis pigmentosa, neovascular glaucoma, diabetic retinopathy, and other eye diseases that involve a local inflammatory process. In some embodiments, the ocular disease is characterized by neovascularization, such as choroidal neovascularization. In some embodiments, the ocular disease is a result of corneal transplantation. In some embodiments, the invention provides methods of treating or preventing one or more aspects or symptoms of an ocular disease including, but not limited to, formation of ocular drusen, inflammation in the eye or eye tissue and loss of vision. In certain embodiments, the compositions and methods described herein can be used to detect and/or treat uveitis, i.e., inflammation of the uvea, the middle layer of the eye beneath the sclera. Uveitis is estimated to be responsible for approximately 10%-20% of the blindness in the United States. The uvea is traditionally divided into 3 areas, from front to back, the iris, ciliary body, and choroid. The prime functions of the uvea are nutrition and gas exchange, light absorption, and secretion of the aqueous humour by the cilliary processes. Uveitis is typically associated with exposure to toxins, infection, and/or autoimmune disorders. However, in many cases, the cause is unknown. Uveitis can affect one or both eyes. Symptoms may develop rapidly and can include blurred vision, floating dark spots in the field of vision, eye pain, eye redness, and sensitivity to light. The most common form of uveitis is anterior uveitis, or iritis, which involves inflammation of the iris. Pars plantis refers to inflammation of the uvea in the middle of the eye, i.e., between the iris and the choroid. Posterior uveitis affects the back of the eye, i.e., the choroid Inflammation associated with posterior uveitis can also affect the retina (retinitis) or the blood vessels at the back of the eye (vasculitis).

In certain embodiments, the methods and compositions of the invention can be used to treat retinitis pigmentosa (RP). RP is a heritable eye disease that is caused by abnormalities of the photoreceptors (rods and cones) or the retinal pigment epithelium of the retina. The disease can lead to progressive sight loss and often blindness. The symptoms of RP include decreased vision at night or in low light, loss of side (peripheral) vision, and, in advanced cases, loss of central vision. The diagnosis of RP relies upon the documentation of progressive loss in photoreceptor cell function via visual field testing and electroretinography. At least 35 genetic loci are known to cause "non-syndromic retinitis pigmentosa" (i.e., RP that is not the result of another disease or part of a wider syndrome).

In certain embodiments, the methods and compositions of the invention can be used to treat diabetic retinopathy. Diabetic retinopathy refers to damage to the retina caused by the complications of diabetes. Specifically, vascular walls are compromised by hyperglycemia, changing the formation of the blood-retinal barrier and making the retinal blood vessels more permeable. The damaged blood vessels least fluid and lipids into the macula, causing the macular to swell (i.e., macular edema), which blurs vision. As the disease progresses, it enters a proliferative stage, in which blood vessels grow along the retina and in the vitreous humour that fills the eye. These blood vessels can bleed, cloud vision, and e.g., destroy the retina, cause retinal detachment, or cause neovascular glaucoma.

In certain embodiments, the methods and compositions of the invention can be used to treat age-related macular degeneration (AMD). AMD is characterized by progressive loss of central vision which occurs as a result of damage to the photoreceptor cells in an area of the retina called the macula. AMD has been broadly classified into two clinical states: a wet form and a dry form, with the dry form making up to 80-90% of total cases. Dry AMD is characterized by the formation of macular drusen, tiny yellow or white accumulations of extracellular material that builds up between Bruch's membrane and the retinal pigment epithelium of the eye. Wet AMD, which accounts for approximately 90% of serious vision loss, is associated with neovascularization, wherein blood vessels grow up from the choroid beneath the retina, and with the leakage of these new vessels. The accumulation of blood and fluid can cause retinal detachment followed by rapid photoreceptor degeneration and loss of vision in either form of AMD. It is generally accepted that the wet form of AMD is preceded by and arises from the dry form.

Methods of delivering an effective amount of a fusion protein to a subject are provided herein. The fusion protein can be delivered to a subject in a composition. The fusion protein can also be delivered to a subject by a rAAV comprising a nucleic acid encoding the fusion protein. Compositions comprising the fusion protein or the rAAV comprising a nucleic acid encoding the fusion protein are contemplated herein.

The compositions described herein can be administered to an individual via any route, including, but not limited to, intravenous (e.g., by infusion pumps), intraperitoneal, intraocular, intra-arterial, intrapulmonary, oral, inhalation, intravesicular, intramuscular, intra-tracheal, subcutaneous, intraocular, intrathecal, transdermal, transpleural, intraarterial, topical, inhalational (e.g., as mists of sprays), mucosal (such as via nasal mucosa), subcutaneous, transdermal, gastrointestinal, intraarticular, intracisternal, intraventricular, intracranial, intraurethral, intrahepatic, and intratumoral. In some embodiments, the compositions are administered intravascularly, such as intravenously (IV) or intraarterially. In some embodiments, the compositions are administered directly into arteries. In some embodiments, the compositions are administered systemically (for example by intravenous injection). In some embodiments, the compositions are administered locally (for example by intraarterial or intraocular injection).

In some embodiments, the compositions are administered directly to the eye or the eye tissue. In some embodiments, the compositions are administered topically to the eye, for example, in eye drops. In some embodiments, the compositions are administered by injection to the eye (intraocular injection) or to the tissues associated with the eye. The compositions can be administered, for example, by intraocular injection, periocular injection, subretinal injection, intravitreal injection, trans-septal injection, subscleral injection, intrachoroidal injection, intracameral injection, subconjunctival injection, sub-Tenon's injection, retrobulbar injection, peribulbar injection, or posterior juxtascleral delivery. These methods are known in the art. For example, for a description of exemplary periocular routes for retinal drug delivery, see Raghava et al., *Expert Opin. Drug Deliv.*, 2004, 1(1):99-114. The compositions may be administered, for example, to the vitreous, aqueous humor, sclera, conjunctiva, the area between the sclera and conjunctiva, the retina choroids tissues, macula, or other area in or proximate to the eye of an individual. The compositions can also be administered to the individual as an implant. Preferred implants are biocompatible and/or biodegradable sustained release formulations which gradually release the compounds over a period of time. Ocular implants for drug delivery are well-known in the art. See, e.g., U.S. Pat. Nos. 5,501,856, 5,476,511, and 6,331,313. The compositions can also be administered to the individual using iontophoresis, including, but are not limited to, the ionophoretic methods described in U.S. Pat. No. 4,454,151 and U.S. Pat. App. Pub. No. 2003/0181531 and 2004/0058313.

The optimal effective amount of the compositions can be determined empirically and will depend on the type and severity of the disease, route of administration, disease progression and health, mass and body area of the individual. Such determinations are within the skill of one in the art. For example, when administered intraocularly, the amount of a rAAV comprising a nucleic acid encoding a fusion protein described herein can be administered to an individual as a DNAse particle resistant (drps) titer of about $10^4$ to about $10^{14}$ drps per dose. In some embodiments, the amount of a rAAV comprising a nucleic acid encoding fusion protein can be administered to an individual at about $10^5$ to about $10^{13}$, about $10^6$ to about $10^{12}$, about $10^7$ to about $10^{11}$, about $10^8$ to about $10^{10}$, about $10^9$ to about $10^{10}$, about $10^{10}$ to about $10^{11}$, or about $10^{11}$ to about $10^{12}$ drps per dose.

Compositions comprising a fusion protein may be administered in a single daily dose, or the total daily dose may be administered in divided dosages of two, three, or four times daily. Compositions comprising a fusion protein can also be administered six times a week, five times a week, four times a week, three times a week, twice a week, once a week, once every two weeks, once every three weeks, once a month, once every two months, once every three months, once every six months, once every nine months, or once every year. Compositions comprising a rAAV comprising a nucleic acid encoding a fusion protein can be administered less frequently, for example, once every three months, every four months, once every five months, once every six months, once every seven months, once every eight months, once every nine months, once every ten months, once every eleven months, or once every year. In some embodiments, a single dose of a composition comprising a rAAV comprising a nucleic acid encoding a fusion protein described herein is administered once a year. The compositions may also be administered in a sustained release formulation, such as in an implant which gradually releases the composition for use over a period of time, and which allows for the composition to be administered less frequently, such as once a month, once every 2-6 months, once every year, or even a single administration. The sustained release devices (such as pellets, nanoparticles, microparticles, nanospheres, microspheres, and the like) may be administered by injection or surgical implanted in various locations in the eye or tissue associated with the eye, such as intraocular, intravitreal, subretinal, periocular, subconjunctival, or sub-Tenons.

Compositions of the invention (e.g., a fusion protein or a rAAV comprising a nucleic acid encoding a fusion protein) can be used either alone or in combination with one or more additional therapeutic agents. For example, the compositions of the invention can be administered alone or in combination with other therapeutic agents known to have a beneficial effect on age-related macular degeneration (AMD), retinal attachment or damaged retinal tissue. Exemplary therapeutic agents include complement inhibitors, anti-angiogenics, anti-VEGF agents (including, but not limited to Macugen (pegaptanib sodium), Eylea (VEGF Trap-Eye), and anti-VEGF antibody, such as Lucentis® or Avastin®), and anti-PDGF agents (such as Fostiva™). The compositions of the invention can be administered in combination with nutritional supplements shown to be beneficial in lowering the risk of macular degeneration progressing to advanced stages, e.g., vitamin C, vitamin E, beta carotene, zinc oxide, and copper. Other useful cofactors include symptom-alleviating cofactors, including antiseptics, antibiotics, antiviral and antifungal agents, and analgesics and anesthetics. In some embodiments, a combination is provided as a simultaneous administration, wherein a fusion protein or a rAAV comprising a nucleic acid encoding a fusion protein and at least one therapeutic agent is administered together in the same composition or administered simultaneously in different compositions. In some embodiments, a combination is provided as a separate administration, wherein the administration of a fusion protein or a rAAV comprising a nucleic acid encoding a fusion protein can occur prior to, simultaneously, and/or following administration of at least one therapeutic agent. The interval between sequential administration can be in terms of at least (or, alternatively, less than) minutes, hours, or days.

The compositions described herein can also be used in conjunction with other AMD therapies, such as photodynamic therapy. Photodynamic therapy entails the intravenous administration of Visudyne (verteporfin), after which light of a specific wavelength is applied to the abnormal blood vessels. The light activates the Visudyne and obliterates the vessels. Alternatively, the compositions described herein can be used in conjunction with laser therapy, which entails using a high-energy laser beam to destroy abnormal blood vessels under the macula.

VIII. Articles of Manufacture and Kits

Also provided are kits or articles of manufacture comprising the compositions described herein (e.g., fusion proteins or rAAV particles) in suitable packaging. Suitable packaging for compositions (such as ophthalmic compositions) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The present invention also provides kits comprising compositions described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing any methods described herein. For example, in some embodiments, the kit comprises a fusion protein described herein and/or a rAAV encoding a fusion protein described herein, a pharmaceutically acceptable carrier suitable for intraocular injection, and one or more of: a buffer, a diluent, a filter, a needle, a syringe, and a package insert with instructions for performing intraocular injection.

EXAMPLES

Example 1: Production of sPDGFR-β/Fc Fusion Proteins

The PDGF-beta receptor (PDGFR-β) ectodomain contains 5 extracellular domains (ECD) numbered 1 to 5 from N-terminus to C-terminus of the protein. The full length PDGFR-β ectodomain was used to generate several truncated soluble PDGFR-β (PDGFR-β) monomeric and dimeric proteins (FIG. 1A).

Two PDGFR-β monomeric constructs were made that contained a PDGFR-β signal peptide (SP) at the N-terminus of the full length PDGFR-β ectodomain, PDGFR(D1-D5) (SEQ ID NO:7), or at the N-terminus of a PDGFR-β ectodomain containing the first four ECDs, PDGFR(D1-D4) (SEQ ID NO:8). Three PDGFR-β dimeric constructs were produced by fusing all five, first three, or first three domains of the PDGFR-β ectodomain (ECD) to the N-terminus of human immunoglobulin G1 heavy-chain fragment (IgG1 Fc) via a peptide linker consisting of nine glycine residues (9Gly) and were termed PDGFR(D1-D5)9G-Fc (SEQ ID NO:9), PDGFR(D1-D3)9G-Fc (SEQ ID NO:10) and PDGFR(D1-D2)9G-Fc (SEQ ID NO:11), respectively. Similar to the monomeric constructs, all dimeric constructs contained an SP at the N-terminus of the fused full-length or truncated PDGFR-β ectodomains. For construction of PDGFR(D1-D2)9G-Fc, the plasmid pCMV6-XL5-PDG-FRB (Cat.# SC309979; Origene, Rockville, Md.) was used as a template together with primers that introduced the restriction sites SpeI (PDGFRBPR6SpeI F: 5'-GACTAG-TATGCGGCTTCCGGGTG (SEQ ID NO:25) and AgeI (PDGFRBPR7AgeI R: 5'-ACCGGTGGATGACACCTG-GAGTCTG (SEQ ID NO:26) into the template. Amplification of the PCR products was achieved with the following cycling parameters: 1 cycle at 50° C. for 2 min, 1 cycle at 95° C. for 10 min; 40 cycles of 95° C. for 15 sec, and 60° C. for 60 sec. The PCR product was inserted into pCR-Blunt II-TOPO plasmid using TOPO Cloning Kit (Invitrogen) and the sequence of the PCR product insert was verified by sequencing before subcloning into SpeI and AgeI sites of plasmid pCMV/K-D2-9Gly-Fc (See Pechan P., et al. *Gene Ther*. (2009), 16:10-16 for a description of the pCMV/K-D2-9Gly-Fc) to generate plasmid pCMV-PDGFR-S-(D1-D2)-9Gly-Fc with the open reading frame of PDGFR(D1-D2)9G-Fc (SEQ ID NO:20) under control of CMV promoter and SV40 polyadenylation sequence. For construction of PDGFR(D1-D5)9G-Fc, the plasmid pCMV6-XL5-PDG-FRB (Cat.# SC309979; Origene, Rockville, Md.) was used as a template together with primers that introduced the restriction sites AccI (PDGFRB-PR1-Acc F: 5'-CTATGTC-TACAGACTCCAGGTGTC (SEQ ID NO:27) and AgeI (D5-PR9-AgeI-Rev R: 5'-ACCGG-TAAAGGGCAAGGAGTGTGGC (SEQ ID NO:28) into the template. Amplification of the PCR products was achieved with the following cycling parameters: 1 cycle at 50° C. for 2 min, 1 cycle at 95° C. for 10 min; 40 cycles of 95° C. for 15 sec, and 60° C. for 60 sec. The PCR product was then inserted into pCR-Blunt II-TOPO plasmid using TOPO Cloning Kit (Invitrogen) and the sequence of PCR product insert in the pTOPO-PDGFRB (D3-D5) was verified by sequencing. The 622 base pair (bp) SpeI-AccI fragment from plasmid pCMV-PDGFR-S-(D1-D2)-9Gly-Fc was inserted into SpeI and AccI sites of plasmid pTOPO-PDGFRB (D3-5) to generate plasmid pTOPO-PDGFR(D1-D5). The 1,596 bp SpeI-AgeI fragment from plasmid pTOPO-PDGFR(D1-D5) was then inserted into the SpeI and AgeI sites of plasmid pCMV-PDGFR-S-(D1-D2)-9Gly-Fc to generate the plasmid pCMV-PDGFR-(D1-D5)-9Gly-Fc with the open reading frame of PDGFR(D1-D5)9G-Fc (SEQ ID NO:18) under control of the CMV promoter and SV40 polyadenylation sequence. For construction of PDGFR(D1-D3)9G-Fc, the plasmid pCMV-PDGFR (D1-5)9G-Fc was used as a template together with primers that introduced the restriction sites SpeI (PDGF02 F: 5'-CCTCCACCGGTG-TAGCCGCTCTCAACCACGGT (SEQ ID NO:29) and AgeI (PDGF03 R: 5'-CCCGGGACTAGTATGCGGCTTC-CGGGTG (SEQ ID NO:30) into the template. Amplification of the PCR product was achieved with the following cycling parameters: 1 cycle at 95° C. for 1 min; 35 cycles of 95° C. for 30 sec, 60° C. for 30 sec, and 72° C. for 1 min. The PCR product was inserted into the Spe I and Age I sites of plasmid pCMV-PDGFR (D1-5)9G-Fc to complete the open reading frame of PDGFR (D1-3)9G-Fc (SEQ ID NO:19). For construction of PDGFR(D1-D5), the 5307 bp AgeI-EagI fragment of plasmid pCMV-sPDGFR(D1-D5)-9G-Fc was ligated to an annealed oligonucleotide fragment consisting of oligonucleotides D5-SV40 F: CCGGTTAGGGA (SEQ ID NO:31) and D5-SV40 B-2: GGCCTCCCTAA (SEQ ID NO:32) to generate plasmid pCMVPDGFRB (D1-D5) with the open reading frame of PDGFR(D1-D5) (SEQ ID NO:16) under control of the CMV promoter and SV40 polyadenylation sequence. For the construct PDGFR(D1-D4), a 4924 bp BbvCI-EagI fragment of plasmid pCMV-sPDGFR (D1-D5)-9G-Fc was ligated to an annealed oligonucleotide fragment consisting of oligonucleotides D4-SV40 F: TGAGGTCCAGCTCTCCTTCCAGCTACAGATCAAT-GTCCCTGTCCGAGTGCTGGAGTA GC (SEQ ID NO:33) and D4-SV40 B: GGCCGCTACTCCAGCACTCGGACA-GGGACATTGATCTGTAGCTGGAAGGAGAGCTG GACC (SEQ ID NO:34) to generate plasmid pCMV-PDG-FRB (D1-D4) with the open reading frame of PDGFR(D1-D4) (SEQ ID NO:17) under control of the CMV promoter and SV40 polyadenylation sequence.

Figure 1B:
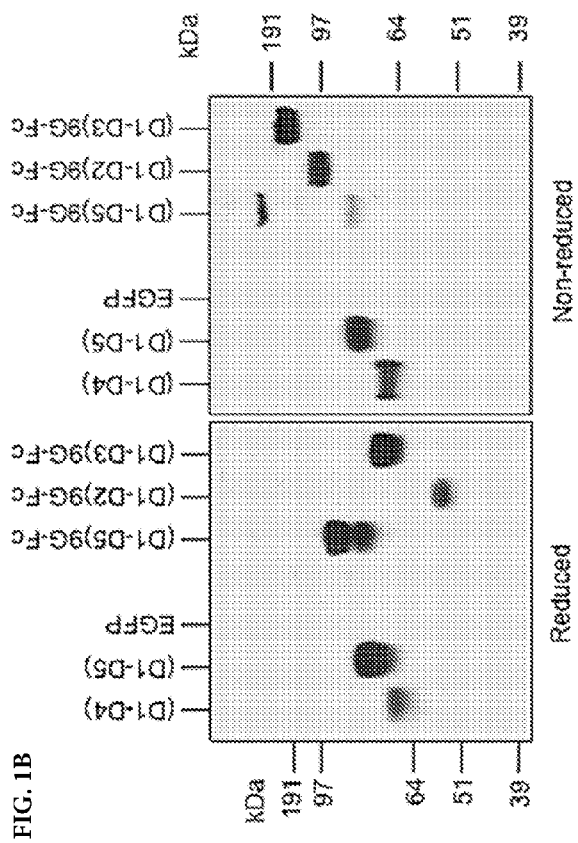

The predicted molecular weights for the mature proteins, excluding the SP region, was 56.2 kDa for PDGFR(D1-D5) and 43.6 kDa for PDGFR(D1-D4). The predicted molecular weights for the mature proteins as monomers, excluding the SP region, were 82.7 kDa for PDGFR(D1-D5)9G-Fc, 46.7 kDa for PDGFR(D1-D2)9G-Fc, and 58.2 kDa for PDGFR (D1-D3)9G-Fc. The plasmids encoding these protein constructs were used for transfection of 293 cells. Media from the cells was collected 72 hours post-transfection and crude conditioned media (CM) was used for analysis of secreted PDGFR(D1-D5), PDGFR(D1-D4), PDGFR(D1-D5)9G-Fc, PDGFR(D1-D2)9G-Fc and PDGFR(D1-D3)9G-Fc proteins. Production of PDGFR(D1-D5)9G-Fc, PDGFR(D1-D2)9G-Fc and PDGFR(D1-D3)9G-Fc protein homodimers by cells transfected with their respective constructs was confirmed by Western blot analysis. Briefly, secreted proteins purified from cell culture media was loaded into reducing or non-reducing polyacrylamide gel electrophoresis (PAGE) gels. Enhanced Green Fluorescent protein (EGFP) purified from cell culture media of cells transfected with an EGFP construct was also loaded on the gels and used as a control. After separating the proteins on the SDS-PAGE gels (NuPAGE Novex 4-12% Bis-Tris, Invitrogen), the proteins were transferred to nitrocellulose membranes. The membranes were probed with a biotinylated goat anti-human PDGFR-β antibody (R&D Systems), followed by labeling with Streptavidin conjugated to horseradish peroxidase (R&D Systems) and developed with chemiluminescence reagent (Thermo-Scientific Pierce) prior to imaging. The mobility of PDGFR (D1-D5)9G-Fc, PDGFR(D1-D2)9G-Fc and PDGFR(D1-D3)9G-Fc proteins changed under reducing and non-reducing conditions while the mobility of the PDGFR(D1-D5) and PDGFR(D1-D4) monomer proteins remained unchanged indicating that the PDGFR-β/Fc fusion proteins formed homodimers (FIG. 1B).

Figure 2A:
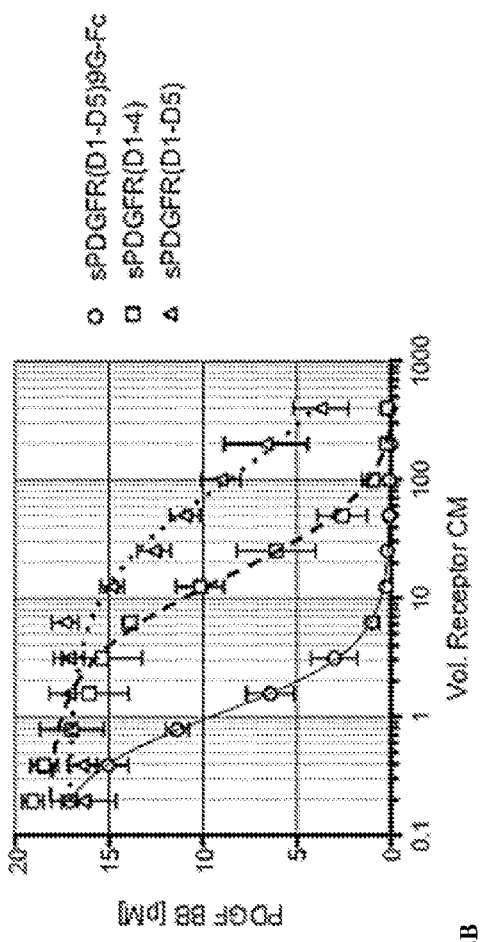
FIGS. 2A and 2B shows a volumetric PDGF BB binding assay of truncated PDGFR-soluble receptors. A) Monomeric PDGFR-β soluble receptor forms PDGFR(D1-D4) and PDGFR(D1-D5) as compared to the full-size IgG1 Fc-coupled dimerizing form PDGFR(D1-D5)9G-Fc. B) Dimeric IgG1 Fc-coupled sPDGFR-β soluble receptor forms PDGFR(D1-D2)9G-Fc and PDGFR(D1-D3)9G-Fc as compared to the IgG1 Fc-coupled dimerizing form PDGFR (D1-D5)9G-Fc. Increasing volumes (μl) of conditioned media (CM) containing soluble receptors (x axis) from representative transfections were incubated overnight with human PDGF BB ligand and the amount of unbound ligand (y axis) was measured by ELISA. Data expressed as mean±SD (n=3); all receptors were significantly different in PDGF binding affinities by 2-way ANOVA; Bonferroni Test; ***P<0.001.
Figure 2B:
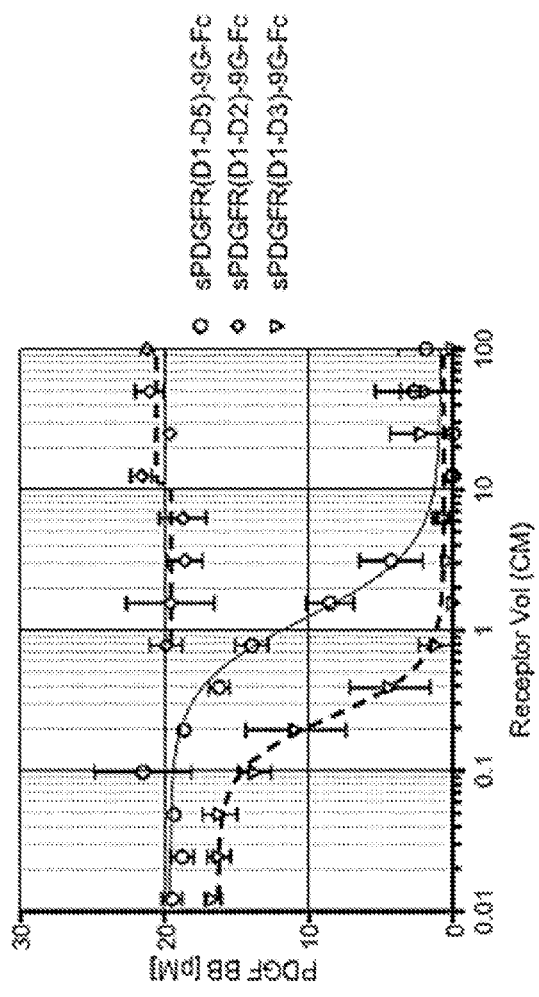

The relative binding affinity between PDGF BB ligand and the PDGFR-β monomeric and dimeric proteins was determined using a cell-free volumetric PDGF binding assay system (FIG. 2). For production of PDGFR-β monomeric and dimeric proteins, 293 cells were transfected with plasmids encoding PDGFR(D1-D5), PDGFR(D1-D4), PDGFR (D1-D5)9G-Fc, PDGFR(D1-D2)9G-Fc, or PDGFR(D1-D3) 9G-Fc proteins and cell culture media was harvested 72 hours post-transfection. The presence of secreted PDGFR-β monomeric and dimeric proteins was confirmed by ELISA and Western blot analysis prior to binding affinity analysis. Secreted proteins were serially diluted, mixed with human PDGF BB ligand (20 pM final concentration) and incubated overnight at room temperature on an orbital shaker platform. The amount of unbound PDGF BB was then measured by a human PDGF-specific ELISA (Human PDGF-BB DuoSet Product #DY220, R&D Systems). Statistical significance in binding affinities was analyzed using Prism 5.0d (GraphPad Software, Inc) and was calculated using the 2-way ANOVA test followed by Bonferroni correction. Binding affinity analysis showed that monomeric PDGFR(D1-D4) protein bound PDGF with significantly (*P<0.001) higher affinity than monomeric PDGFR(D1-D5) protein that contained all 5 ECDs (FIG. 2A). However, the dimeric full length PDGFR (D1-D5)9G-Fc protein, that served as a positive control for PDGF binding was a significantly (*P<0.001) better PDGF binder than both monomeric PDGFR(D1-D4) and PDGFR(D1-D5) (FIG. 2A). Out of three dimeric IgG1 Fc-coupled PDGFR-β constructs generated, the construct with first three ECDs, PDGFR(D1-D3)9G-Fc, was a significantly (*P<0.001) better PDGF binder than the full-size PDGFR(D1-D5)9G-Fc protein, while the construct with the first two ECDs, PDGFR(D1-D2)9G-Fc showed no PDGF-binding affinity (FIG. 2**B).

Example 2: Generation of Hybrid VEGFR1/PDGFR-β and PDGFR-β/VEGFR-1 Proteins

Figure 3:
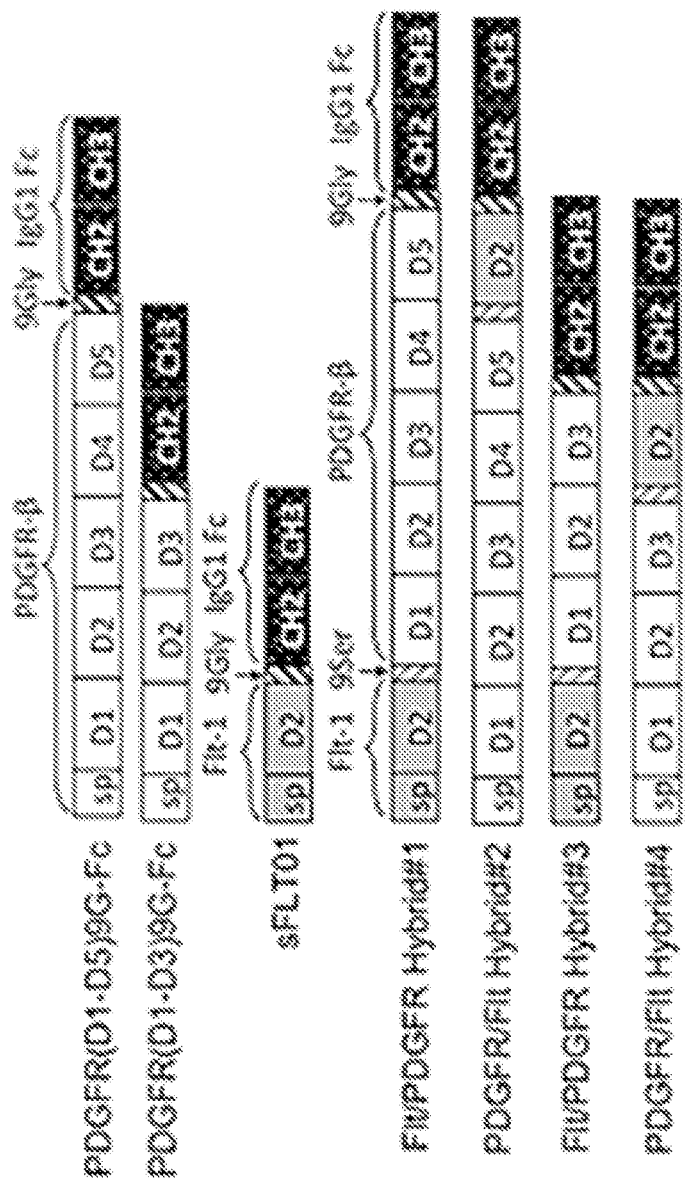
FIG. 3 is a schematic of VEGFR1/PDGFR-β and PDGFR-β/VEGFR1 hybrid proteins, Hybrids 1 to 4, and their parental constructs PDGFR(D1-D5)9G-Fc, PDGFR (D1-D3)9G-Fc and sFLT01. White blocks indicate PDGFR-β sequences, grey blocks indicate VEGFR1 (Flt-1) sequences, including their extracellular domains and signal peptides (sp). Diagonal shaded blocks represent 9Gly or 9Ser linkers and dark dotted blocks represent domains CH2 and CH3 of the human IgG1 Fc region.
Figure 4:
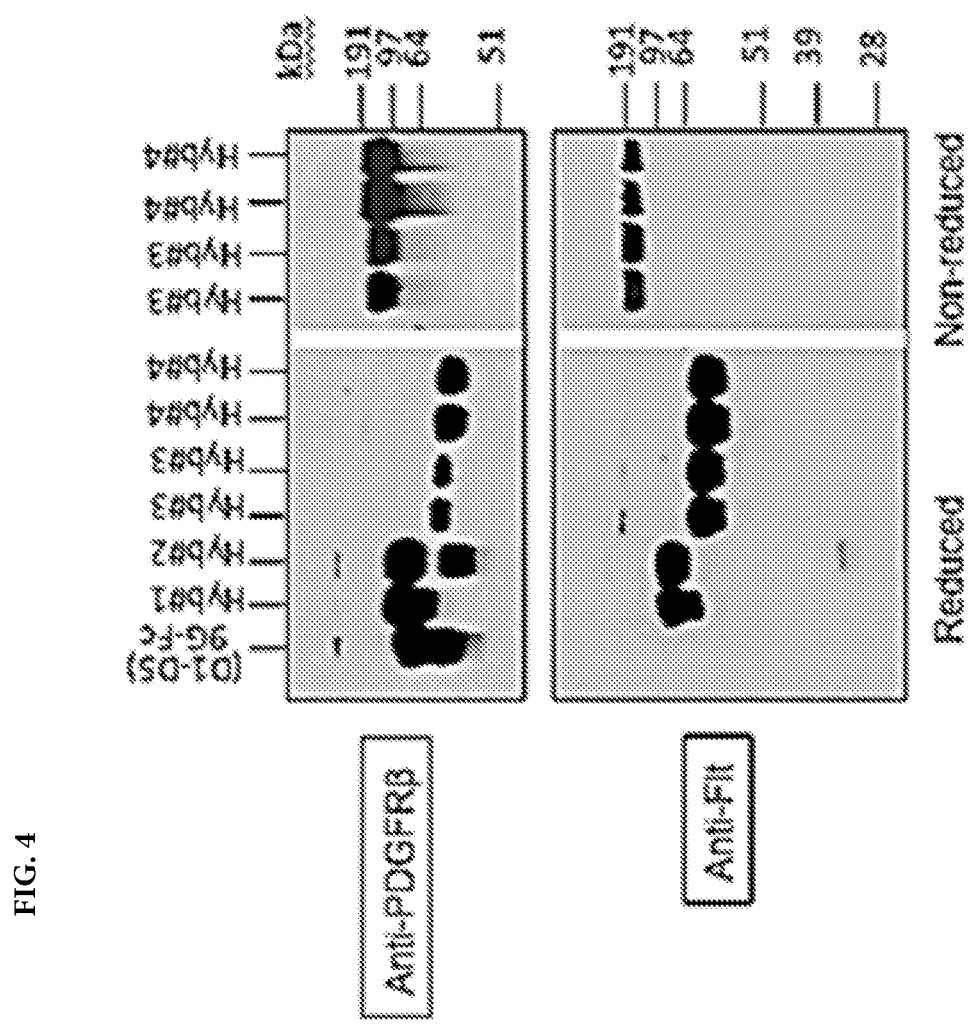
FIG. 4 is a Western blot of VEGFR1/PDGFR-β and PDGFR-β/VEGFR1 hybrid proteins, Hybrids 1 to 4, as compared to full-size IgG1 Fc-coupled dimerizing form PDGFR(D1-D5)9G-Fc (shown as (D1-D5)9G-Fc) under reducing (left panel) and non-reducing (right panel) conditions. Protein was detected with anti-PDGFR-β antibody and anti-Flt-1 antibody. Samples containing Hybrids 3 and 4 were duplicates from individual transfections.

The Flt-1 receptor (VEGFR-1) ectodomain contains 7 extracellular domains (ECD) numbered 1 to 7 from N-terminus to C-terminus of the protein. In order to block both PDGF BB and VEGF ligands, fusion proteins comprising ECDs of PDGFR-β and VEGFR1 were generated and termed hybrid proteins (FIG. 3).

A previously generated VEGF-binding protein, sFLT01, consisting of ECD 2 of human VEGFR1 linked to a human immunoglobulin G1 heavy-chain fragment (IgG1 Fc) was used to generate DNA constructs encoding the VEGFR1/PDGFR-β or PDGFR-β/VEGFR1 hybrid proteins. See Pechan P., et al. *Gene Ther*. (2009), 16:10-16 for a description of the sFLT01 protein, which is incorporated herein by reference in its entirety. VEGFR1/PDGFR-β Hybrid 1 (SEQ ID NO:12) was constructed by linking a fragment from sFLT01 containing the VEGFR1 signal peptide (SP) and VEGFR1 ECD 2 to the N-terminus of PDGFR-β ECD 1-5 via a peptide linker consisting of nine serine residues (9Ser) which was further linked to IgG1 Fc via a peptide linker consisting of nine glycine residues (9Gly). PDGFR-β/VEGFR1 Hybrid 2 (SEQ ID NO:13) was constructed by linking PDGFR-β ECD 1-5 and the PDGFR-β SP to the N-terminus of VEGFR1 ECD 2 via a 9Ser peptide linker which was further linked to IgG1 Fc via a 9Gly peptide linker. VEGFR1/PDGFR-β Hybrid 3 (SEQ ID NO:14) and PDGFR-β/VEGFR1 Hybrid 4 (SEQ ID NO:15) were composed similarly to Hybrids 1 and 2, respectively, with the exception that PDGFR-β ECD 1-3 was used instead of PDGFR-β ECD 1-5. For construction of VEGFRUP-DGFR-β Hybrid 1, a 372 bp SpeI-XhoI fragment Kozak-SP-D2-9Ser encoding a VEGFR1 signal peptide fused to a VEGFR1 domain D2 comprising a 9-Serine (9Ser) linker (SEQ ID NO:35) was inserted into SpeI and XhoI sites of plasmid pTOPO-PDGFR(D1-D5) to generate plasmid pTOPO-(D2-9Ser)-PDGFR(D1-D5). The SpeI-AgeI fragment from plasmid pTOPO-(D2-9Ser)-PDGFR(D1-D5) was inserted into SpeI-AgeI sites of plasmid pCMV-PDGFR-(D1-D5)-9Gly-Fc to create pCMV-F(D2-9S)-P(D1-D5)-9G-Fc or pCMV-Hybrid 1 with the open reading frame of VEGFRUPDGFR-β Hybrid 1 (SEQ ID NO:21) under control of CMV promoter and SV40 polyadenylation sequence. For construction of PDGFR-β/VEGFR1 Hybrid 2, a 678 bp BstBI-BmgXI fragment containing synthetic DNA (GenScript) (SEQ ID NO:36) was ligated with 5626 bp BstBI-BmgXI fragment of plasmid pCMV-sPDGFR(D1-D5)-9G-Fc to create pCMV-P(D1-D5)-95-F(D2)-9G-Fc or pCMV-Hybrid 2 with an open reading frame of PDGFR-β/VEGFR-1 Hybrid 2 (SEQ ID NO:22) under control of CMV promoter and SV40 polyadenylation sequence. For construction of VEGFRUPDGFR-β Hybrid 3, a 452 bp BmgBI-PshAI fragment containing synthetic DNA (GenScript) (SEQ ID NO:37) was ligated with 5334 bp BmgBI-PshAI fragment of plasmid pCMV-P(D1-D5)-9S-F(D2)-9G-Fc or pCMV-Hybrid 2 to create pCMV-F(D2-9S)-P(D1-D3)-9G-Fc or pCMV-Hybrid 3 with open reading frame of VEG-FRUPDGFR-β Hybrid 3 (SEQ ID NO:23) under control of CMV promoter and SV40 polyadenylation sequence. For construction of PDGFR-β/VEGFR1 Hybrid 4, a 758 bp BmgBI-PshAI fragment containing synthetic DNA (GenScript) (SEQ ID NO:38) was ligated with 5021 bp BmgBI-PshAI fragment of plasmid pCMV-P(D1-D5)-9S-F(D2)-9G-Fc or pCMV-Hybrid 2 to create pCMV-P(D1-D3)-9S-F (D2)-9G-Fc or pCMV-Hybrid 4 with open reading frame of PDGFR-β/VEGFR1 Hybrid 4 (SEQ ID NO:24) under control of CMV promoter and SV40 polyadenylation sequence.

Production of Hybrid 1, Hybrid 2, Hybrid 3, and Hybrid 4 protein homodimers by cells transfected with their respective constructs was confirmed by Western blot analysis. Briefly, secreted proteins from cell culture media were loaded into reducing or non-reducing polyacrylamide gel electrophoresis (PAGE) gels. PDGFR(D1-D5)9G-Fc protein was also loaded on the gels and used as a control. After separating the proteins on the SDS-PAGE gels, (NuPAGE Novex 4-12% Bis-Tris, Invitrogen), the proteins were transferred to nitrocellulose membranes. The membranes were probed with a biotinylated goat anti-human PDGFR-β antibody (R&D Systems), followed by labeling with Streptavidin conjugated to horseradish peroxidase (R&D Systems) and developed with chemiluminescence reagent (ThermoScientific Pierce) prior to imaging. The protein mobility of Hybrids 1, 2, 3, and 4 under non-reducing conditions as compared to reducing conditions confirmed that the hybrid proteins dimerized (FIG. 4). PDGFR(D1-D5)9G-Fc and Hybrids 1 and 2, which all contain five PDGFR-β ECDs, showed two PDGFR-positive bands under reducing conditions, suggesting a possible proteolytic cleavage of these proteins in the area of the fifth PDGFR-β ECD (FIG. 4, left panel). Hybrids 3 and 4, which contain only the first three PDGFR-β ECDs, do not appear to be cleaved indicating that they do not contain the proteolytic cleavage site seen in Hybrids 1 and 2 (FIG. 4, left panel).

Example 3: Inhibition of HUVEC Proliferation by PDGFR-β/VEGFR1 Hybrid Proteins

Figure 5A:
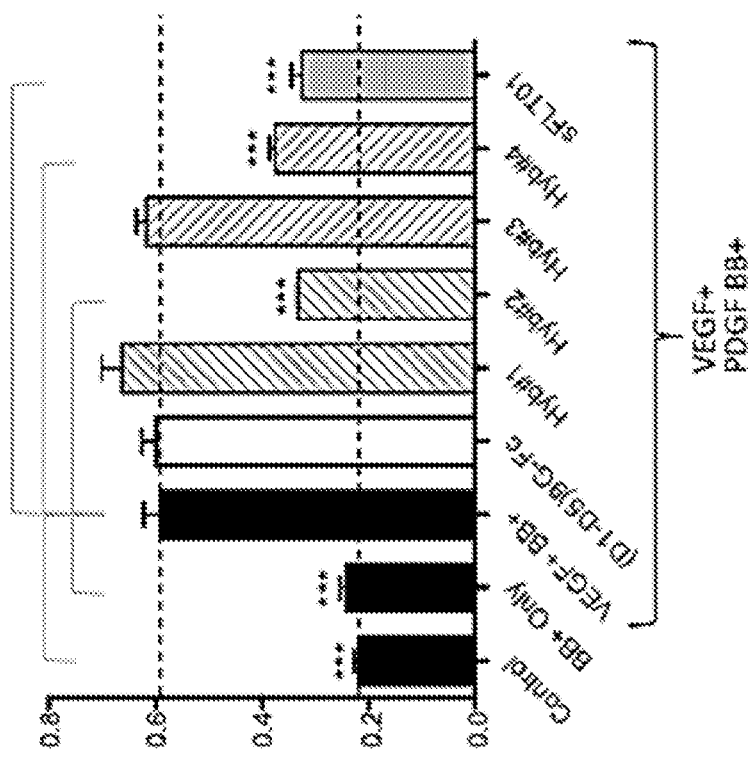
FIGS. 5A and 5B shows graphs demonstrating inhibition of VEGF-induced and VEGF+PDGF-β-induced proliferation of human umbilical vein endothelial cells (HUVECs) by hybrid protein, Hybrids 1 to 4. A) HUVEC proliferation assay with VEGF only: Inhibitory effect of 5 μl conditioned media (CM) containing soluble receptors on HUVEC proliferation was compared in the presence of VEGF (10 ng/ml) only. B) HUVEC competitive proliferation assay in the presence of VEGF (10 ng/ml) and PDGF (20 ng/ml): Inhibitory effect of 5 μl CM containing soluble receptors on HUVEC proliferation was compared in the presence of both ligands, VEGF and PDGF. Samples from three independent transfections (n=3) were evaluated in one assay. Data expressed as mean±SD. One-way ANOVA; Tukey's Test; ***p<0.001 for difference between positive control VEGF+ alone or VEGF+ in combination with PDGF BB+ versus other samples. Control=EGFP CM; VEGF+=EGFP CM+10 ng/ml VEGF; BB+ Only=EGFP CM+20 ng/ml; VEGF+BB+ =EGFP CM+10 ng/ml VEGF+20 ng/ml PDGF BB.
Figure 5B:
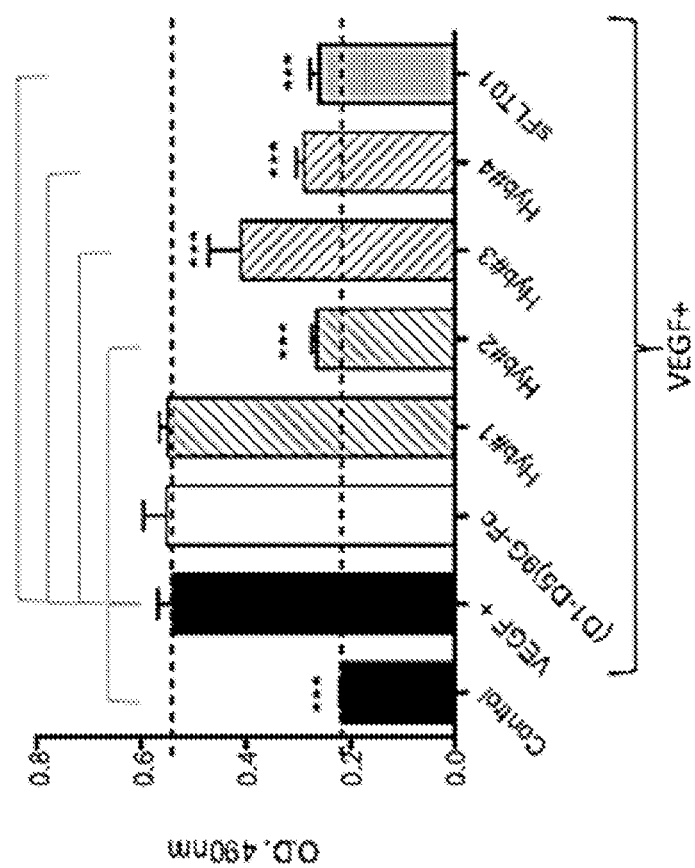

Hybrid PDGFR-β/VEGFR1 proteins were tested for their ability to inhibit VEGF- and/or PDGFR-β-induced proliferation of human umbilical vein endothelial cells (HUVECs). For production of hybrid proteins, 293 cells were transfected with constructs encoding Hybrid 1, Hybrid 2, Hybrid 3, or Hybrid 4 and the cell culture media containing the secreted hybrid proteins was harvested 72 hours after transfection. The harvested cell culture was applied to HUVECs in the presence of VEGF ligand. HUVECs (HUVEC—Cambrex Bio Science Walkersville, Inc) were seeded in a 96 well plate at a density of 2,000 cells/well in Media 199 (Invitrogen) supplemented with 5% Fetal Bovine Serum (Invitrogen) and settled overnight. After incubation, the media was replaced with Media 199 (Invitrogen) supplemented with 5% Fetal Bovine Serum (Invitrogen) containing an equal volume (50) of harvested cell culture generated from three independent receptor or control transfections together with recombinant hVEGF-165 ligand alone at a final concentration of 10 ng/ml (R&D Systems Cat#293-VE), or in combination with PDGF-BB ligand at a final concentration of 20 ng/ml (R&D Systems Cat#220-BB) in a final volume of 100 µl per well. Negative controls consisted of an equal volume (50) of harvested cell culture from cells transfected with an EGFP construct at a 100 µL final volume per well. Positive controls included harvested cell culture of an equal volume (5 µl) from cells transfected with an EGFP construct in the presence of VEGF ligand or VEGF and PDGF BB ligand 100 µL final volume per well. Cells were incubated at 37° C. in 5% $CO_2$ for three to four days. Cell Titer 96 $AQ_{ueous}$ One Solution Reagent (Promega Cat# G3580) was added at 20 µl/well and absorbance at 490 nm was taken four hours later. In the VEGF-dependent HUVEC proliferation assay, Hybrid 2, Hybrid 3, and Hybrid 4 significantly blocked HUVEC proliferation with Hybrids 2 and 4 having a similar potency as sFLT01 (FIG. 5A). In comparison to Hybrids 2, 3, and 4, Hybrid 1 did not block VEGF-induced HUVEC proliferation and had similar levels of anti-proliferative activity as PDGFR(D1-D5)9G-Fc protein that lacks VEGFR1 ECDs (FIG. 5A). The proteolytic excision of the dimerizing IgG1-Fc sequence in Hybrid 1 probably eliminated its VEGF binding ability, because dimerization is a limiting factor for VEGFR1 D2 mediated VEGF binding when other ECDs are not present (Pechan P., et al. *Gene Ther.* (2009), 16:10-16). In Hybrid 2, however, proteolytic cleavage separated the molecule into PDGFR-β ECDs and sFLT01-containing units that were still able to bind VEGF (FIG. 5A). The harvested hybrid PDGFR-β/VEGFR1 proteins were also tested in a HUVEC competitive proliferation assay. In this assay, harvested cell culture was applied to HUVECs in the presence of both VEGF ligand and PDGF BB ligand as described above. Results from this assay were similar to the previous assay in that Hybrid 2 and Hybrid 4 significantly blocked HUVEC proliferation with Hybrids 2 and 4 having a similar potency as sFLT01 (FIG. 5B). Hybrid 1 also did not block HUVEC proliferation in the presence of both ligands. In contrast to the last assay, Hybrid 3 had weaker ant-proliferative potency in the presence of both ligands and was comparable to activity of the PDGFR (D1-D5)9G-Fc protein that lacks VEGFR1 ECDs (FIG. 5B). Statistical significance for both HUVEC proliferation assays was analyzed using Prism 5.0d (GraphPadSoftware Inc) and calculated using the one-way ANOVA test followed by Tukey's Test.

Example 4: Binding Affinities for PDGFR-β/VEGFR1 Hybrid Proteins

Figure 6A:
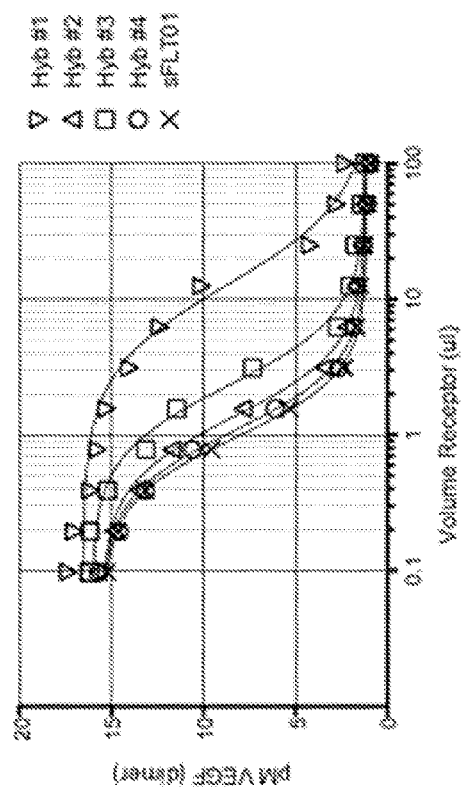
FIGS. 6A and 6B shows volumetric binding assays of hybrid proteins. A) PDGF BB volumetric binding assay of Hybrid proteins 1 to 4 as compared to PDGFR(D1-D5)9G-Fc. B) VEGF volumetric binding assay of Hybrid proteins 1 to 4 as compared to sFLT01. Increasing conditioned media volumes containing soluble receptors (x axis) from representative transfections were incubated overnight with either human PDGF BB or VEGF ligands and the amount of unbound ligand (y axis) was measured by ELISA in triplicates.
Figure 6B:
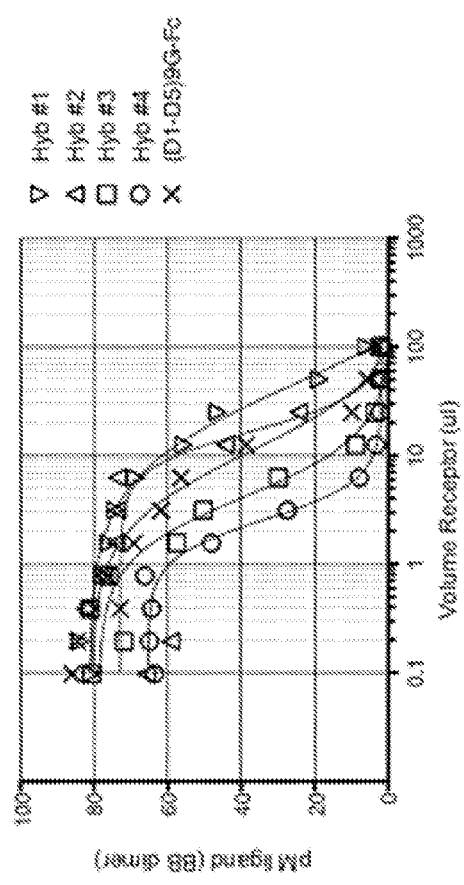

The relative binding affinities between both VEGF and PDGF BB ligands and the PDGFR-β/VEGFR1 hybrid proteins was determined using a cell-free volumetric PDGF or VEGF binding assay system (FIG. 6). For production of hybrid PDGFR-β/VEGFR1 proteins, 293 cells were transfected with plasmids encoding Hybrid 1, Hybrid 2, Hybrid 3, or Hybrid 4. Cells were also transfected with plasmids encoding PDGFR(D1-D5)9G-Fc or sFLT01 proteins for use as binding controls. Cell culture media was harvested 72 hours post-transfection and the presence of secreted proteins was confirmed by ELISA and Western blot analysis prior to binding affinity analysis. Secreted proteins were serially diluted, mixed with human VEGFR1 ligand (20 pM final concentration) or human PDGF BB ligand (80 pm final concentration) and incubated overnight at room temperature on an orbital shaker platform. The amount of unbound PDGF BB was then measured by a human VEGF-specific ELISA (Human VEGF Quantikine ELISA kit Cat# DVE00, R&D Systems) or a human PDGF-specific ELISA (Human PDGF-BB DuoSet, R&D Systems). Comparison of all four hybrids in the VEGF binding assay showed that Hybrid 1 was the weakest VEGF binder (FIG. 6A). VEGF binding comparison of Hybrid 3, Hybrid 4 and sFLT01 in conditioned media harvested from three individual transfections in one assay showed that Hybrid 4 bound VEGF similarly to sFLT01 and was a stronger VEGF binder than Hybrid 3 (FIG. 6A). Comparison of all four hybrids in the PDGF binding assay demonstrated that Hybrid 1 was also the weakest PDGF binder while Hybrid 4 demonstrated the best binding out of all four hybrids (FIG. 6B).

Figure 7B:
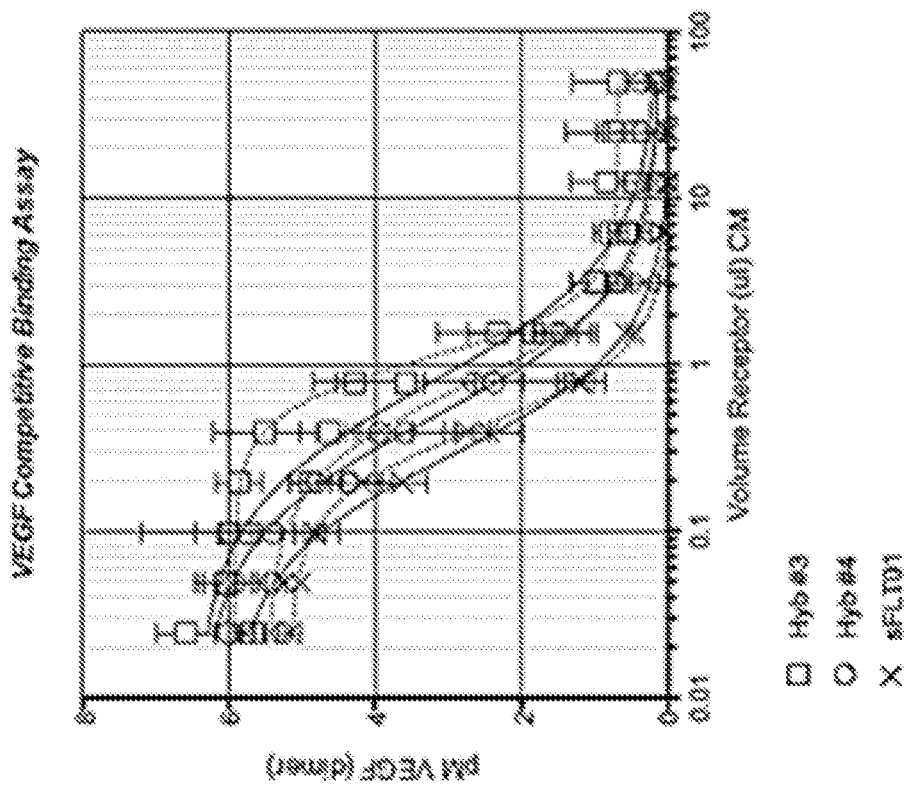
FIGS. 7A and 7B shows competitive VEGF and PDGF cell-free binding assays of hybrid proteins. A) Comparison of Hybrid 3 (Hyb#3), Hybrid 4 (Hyb #4), and PDGFR(D1-D3)9G-Fc in increasing conditioned media volumes (x-axis) and the amount of the unbound PDGF ligand (y axis) as measured by PDGF BB ELISA. B) Comparison of Hybrid 3 (Hyb#3), Hybrid 4 (Hyb #4), and sFltT01 in increasing conditioned media volumes (x-axis) and the amount of the unbound VEGF ligand (y axis) as measured by VEGF ELISA.
Figure 7A:
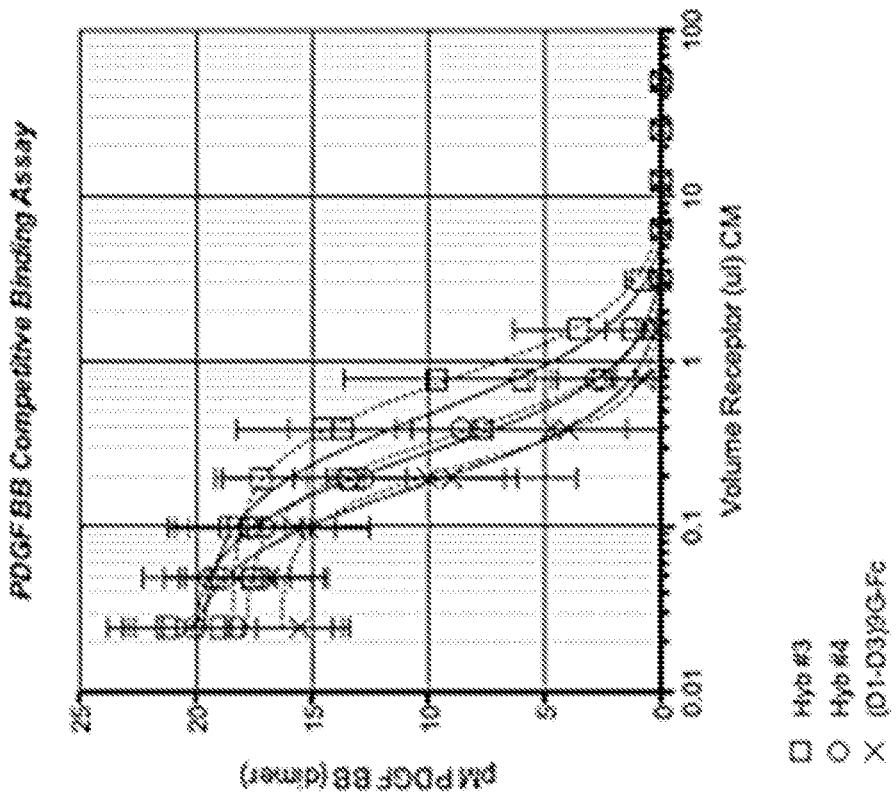

Competitive VEGF and PDGF cell-free binding assays were conducted using conditioned media harvested from 293 cells transfected with constructs encoding Hybrid 3, Hybrid 4, PDGFR(D1-D3)9G-Fc, or sFLT01 proteins. Cell culture media was harvested 72 hours post-transfection and the presence of secreted proteins was confirmed by ELISA and Western blot analysis prior to binding affinity analysis. Secreted proteins were serially diluted, mixed with both human PDGF BB ligand (20 pM final concentration) and human VEGFR1 ligand (20 pM final concentration) and incubated overnight at room temperature on an orbital shaker platform. The amount of unbound PDGF-BB and VEGF ligands was subsequently measured by a human VEGF-specific ELISA (Human VEGF Quantikine ELISA kit Cat# DVE00, R&D Systems) or a human PDGF-specific ELISA (Human PDGF-BB DuoSet, R&D Systems). Comparison of Hybrid 3 and Hybrid 4 to the PDGF BB binding control (PDGFR(D1-D3)9G-Fc) and VEGF binding control (sFLT01) showed that Hybrid 3 and Hybrid 4 both bound to PDGF BB (FIG. 7A) and VEGF (FIG. 7B) ligands, with Hybrid 4 demonstrating a higher binding affinity to both ligands. PDGF binding comparison using cell culture media from cells expressing Hybrid 3, Hybrid 4, PDGFR(D1-D5) 9G-Fc, or PDGFR(D1-D3)9G-Fc demonstrated that Hybrid 4 had a similar affinity to the best PDGF binder, PDGFR (D1-D3)9G-Fc (FIG. 7A) while PDGFR(D1-D5)9G-Fc was a significantly weaker PDGF binder than all of Hybrids 1 to 4 (FIG. 6B) or PDGFR(D1-D3)9G-Fc (FIG. 2B).

Example 5: Inhibition of Laser-Induced CNV in Mice by Hybrid PDGFR-β/VEGFR1 Proteins Adeno-associated virus (AAV) vectors are attractive tools for intraocular gene delivery because of their nonpathogenic nature, minimal toxicity and immunogenicity, their ability to transduce nondividing cells, and their potential for a lifetime expression of a therapeutic protein (Ali et al. 1996; Ali et al. 1997; Ali et al., 1998; Lai et al. 2005).

Figure 8:
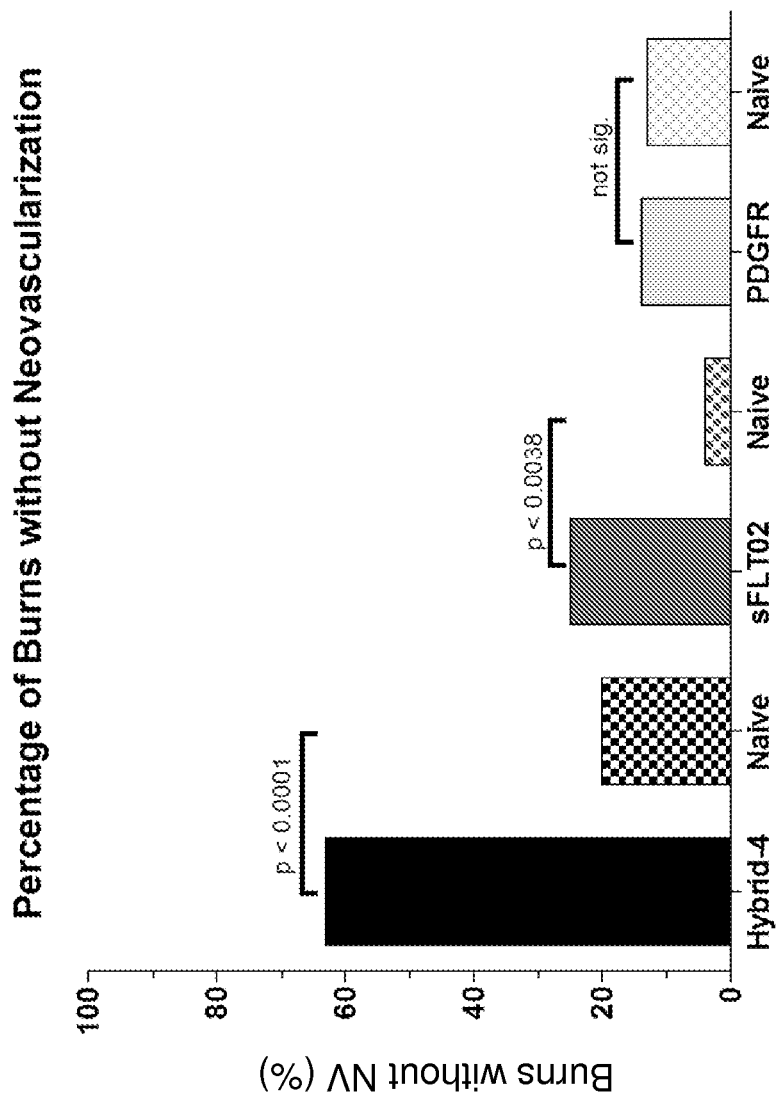
FIG. 8 is a graph showing in vivo efficacy of AAV2.Hybrid 4 intravitreal delivery in a mouse choroidal neovascularization (CNV) laser model. Number of burns without neovascularization (NV) in the AAV2.Hybrid 4 (shown as Hybrid-4), AAV2.sFLT02 (shown as sFLT02), AAV2.PDGFR (shown as PDGFR) treated (left) eye was compared to the untreated contralateral (right; Naive) eye. Data from both eyes (n=20 eyes per treatment) was expressed as percentage of burns without CNV. The PDGFR portion used for construction of AAV2.PDGFR was PDGFR (D1-D3)9G-Fc.

For adeno-associated virus-mediated delivery of Hybrid 4, the CMV promoter was replaced by a chicken beta-actin promoter-CMV intron/enhancer and the an expression cassette comprising the promoter and the fragment encoding Hybrid 4 was inserted into the RsrII and MluI sites of a previral plasmid vector pAAVSP70. See Ziegler et al. *Mol Ther.*, 2004; 9: 231-240. The total size of the resulting AAV genome in plasmid sp70.BR/Hybrid 4 was 4.6 kb. The recombinant vector AAV2.Hybrid 4 was produced by triple transfection of 293 cells using helper plasmids p5rep-D-CMVcap and pHelper (Stratagene, La Jolla, Calif., USA), and purified according to the manufacture's protocol using an iodixanol step gradient and HiTrap Heparin column (GE Healthcare Life Sciences, Piscataway, N.J., USA) on an A "KTA FPLC system (GE Healthcare Life Sciences, Piscataway, N.J.). See Vincent at al., *J Virol.*, 1997; 71: 1897-1905. The AAV2.Hybrid 4 viral preparation had a titer of 2.2E12 drps (DNase resistant particles) per ml. Viral titers were determined using a real-time TaqMan PCR assay (ABI Prism 7700; Applied Biosystems, Foster City, Calif., USA). AAV2.sFLT02 was constructed as previously described in U.S. Pat. No. 7,928,072 using a nucleic acid (SEQ ID NO:40) encoding for the VEGFR1 D2-9Gly-CH3 protein (SEQ ID NO:39). AAV2.Hybrid 4, AAV2.sFLT02, or AAV2.PDGFR (PDGFR=PDGFR(D1-D3)9G-Fc) was administered by intravitreal delivery in a mouse choroidal neovascularization (CNV) laser model to assess the in vivo efficacy of Hybrid 4 in the inhibition of CNV. Briefly, the eyes of normal adult C57BL/6 mice were treated with a single intravitreal injection of 1 E9 drps of AAV2.Hybrid 4, AAV2.sFLT02, or AAV2.PDGFR into the left eye (OS) on study day 0 while the right eye (OD) was left naïve to treatment. CNV was induced in both eyes using a laser (3 burns placed per eye. 200 mW power, 50 μm spot, 100 ms) on study day 28. Mice were perfused with 5 mg/mL of $2.0 \times 10^6$ molecular weight FITC-Dextran and euthanized on study day 42. The eyes were collected, fixed in 10% neutral buffered formalin and choroidal flatmounts were subsequently prepared in order to examine the extent of neovascularization. The number of burns without CNV in the treated (OS) eye was compared to the contralateral (OD) eye. Analysis of in vivo efficacy demonstrated that a single intravitreal injection of AAV2.Hybrid 4 was more effective than AAV2.sFLT02 in the inhibition of retinal neovascularization (FIG. 8). Furthermore, AAV2.PDGFR did not inhibit retinal neovascularization in the murine laser-induced CNV model (FIG. 8).

Sequences

```
PDGFR extracellular region D1-D3 amino acid sequence
                                                    (SEQ ID NO: 1)
LVVTPPGPELVLNVSSTFVLTCSGSAPVVWERMSQEPPQEMAKAQDGTFSSVLTLTNLT

GLDTGEYFCTHNDSRGLETDERKRLYIFVPDPTVGFLPNDAEELFIFLTEITEITIPCRVTD

PQLVVTLHEKKGDVALPVPYDHQRGFFGIFEDRSYICKTTIGDREVDSDAYYVYRLQVS

SINVSVNAVQTVVRQGENITLMCIVIGNEVVNFEWTYPRKESGRLVEPVTDFLLDMPYHI

RSILHIPSAELEDSGTYTCNVTESVNDHQDEKAINITVVESGY

PDGFR extracellular region D1-D4 amino acid sequence
                                                    (SEQ ID NO: 2)
LVVTPPGPELVLNVSSTFVLTCSGSAPVVWERMSQEPPQEMAKAQDGTFSSVLTLTNLT

GLDTGEYFCTHNDSRGLETDERKRLYIFVPDPTVGFLPNDAEELFIFLTEITEITIPCRVTD

PQLVVTLHEKKGDVALPVPYDHQRGFFGIFEDRSYICKTTIGDREVDSDAYYVYRLQVS

SINVSVNAVQTVVRQGENITLMCIVIGNEVVNFEWTYPRKESGRLVEPVTDFLLDMPYHI

RSILHIPSAELEDSGTYTCNVTESVNDHQDEKAINITVVESGYVRLLGEVGTLQFAELHRS

RTLQVVFEAYPPPTVLWFKDNRTLGDSSAGEIALSTRNVSETRYVSELTLVRVKVAEAG

HYTMRAFHEDAEVQLSFQLQINVPVRVLE

PDGFR extracellular region D1-D5 amino acid sequence
                                                    (SEQ ID NO: 3)
LVVTPPGPELVLNVSSTFVLTCSGSAPVVWERMSQEPPQEMAKAQDGTFSSVLTLTNLT

GLDTGEYFCTHNDSRGLETDERKRLYIFVPDPTVGFLPNDAEELFIFLTEITEITIPCRVTD
```

```
                                          -continued
PQLVVTLHEKKGDVALPVPYDHQRGFFGIFEDRSYICKTTIGDREVDSDAYYVYRLQVS

SINVSVNAVQTVVRQGENITLMCIVIGNEVVNFEWTYPRKESGRLVEPVTDFLLDMPYHI

RSILHIPSAELEDSGTYTCNVTESVNDHQDEKAINITVVESGYVRLLGEVGTLQFAELHRS

RTLQVVFEAYPPPTVLWFKDNRTLGDSSAGEIALSTRNVSETRYVSELTLVRVKVAEAG

HYTMRAFHEDAEVQLSFQLQINVPVRVLELSESHPDSGEQTVRCRGRGMPQPNIIWSAC

RDLKRCPRELPPTLLGNSSEEESQLETNVTYWEEEQEFEVVSTLRLQHVDRPLSVRCTLR

NAVGQDTQEVIVVPHSLPFK

VEGFR1 extracellular region D2 amino acid sequence
                                                  (SEQ ID NO: 4)
RPFVEMYSEIPEIIHMTEGRELVIPCRVTSPNITVTLKKFPLDTLIPDGKRIIWDSRKGFIISN

ATYKEIGLLTCEATVNGHLYKTNYLTHRQT

VEGFR1 extracellular region D1-D3 amino acid sequence
                                                  (SEQ ID NO: 5)
PELSLKGTQHIMQAGQTLHLQCRGEAAHKWSLPEMVSKESERLSITKSACGRNGKQFCS

TLTLNTAQANHTGFYSCKYLAVPTSKKKETESAIYIFISDTGRPFVEMYSEIPEIIHMTEGR

ELVIPCRVTSPNITVTLKKFPLDTLIPDGKRIIWDSRKGFIISNATYKEIGLLTCEATVNGHL

YKTNYLTHRQTNTIIDVQISTPRPVKLLRGHTLVLNCTATTPLNTRVQMTWSYPDEKNK

RASVRRRIDQSNSHANIFYSVLTIDKMQNKDKGLYTCRVRSGPSFKSVNTSVHIYDK

IgG1 Fc region amino acid sequence
                                                  (SEQ ID NO: 6)
PKSCDKTHTCPPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGK

PDGFR(D1-D5) amino acid sequence with secretory peptide
(underlined)
                                                  (SEQ ID NO: 7)
MRLPGAMPALALKGELLLLSLLLLLEPQISQGLVVTPPGPELVLNVSSTFVLTCSGSAPV

VWERMSQEPPQEMAKAQDGTFSSVLTLTNLTGLDTGEYFCTHNDSRGLETDERKRLYIF

VPDPTVGFLPNDAEELFIFLTEITEITIPCRVTDPQLVVTLHEKKGDVALPVPYDHQRGFF

GIFEDRSYICKTTIGDREVDSDAYYVYRLQVSSINVSVNAVQTVVRQGENITLMCIVIGN

EVVNFEWTYPRKESGRLVEPVTDFLLDMPYHIRSILHIPSAELEDSGTYTCNVTESVNDH

QDEKAINITVVESGYVRLLGEVGTLQFAELHRSRTLQVVFEAYPPPTVLWFKDNRTLGD

SSAGEIALSTRNVSETRYVSELTLVRVKVAEAGHYTMRAFHEDAEVQLSFQLQINVPVR

VLELSESHPDSGEQTVRCRGRGMPQPNIIWSACRDLKRCPRELPPTLLGNSSEEESQLET

NVTYWEEEQEFEVVSTLRLQHVDRPLSVRCTLRNAVGQDTQEVIVVPHSLPFK

PDGFR(D1-D4) amino acid sequence with secretory peptide
(underlined)
                                                  (SEQ ID NO: 8)
MRLPGAMPALALKGELLLLSLLLLLEPQISQGLVVTPPGPELVLNVSSTFVLTCSGSAPV

VWERMSQEPPQEMAKAQDGTFSSVLTLTNLTGLDTGEYFCTHNDSRGLETDERKRLYIF

VPDPTVGFLPNDAEELFIFLTEITEITIPCRVTDPQLVVTLHEKKGDVALPVPYDHQRGFF

GIFEDRSYICKTTIGDREVDSDAYYVYRLQVSSINVSVNAVQTVVRQGENITLMCIVIGN

EVVNFEWTYPRKESGRLVEPVTDFLLDMPYHIRSILHIPSAELEDSGTYTCNVTESVNDH

QDEKAINITVVESGYVRLLGEVGTLQFAELHRSRTLQVVFEAYPPPTVLWFKDNRTLGD

SSAGEIALSTRNVSETRYVSELTLVRVKVAEAGHYTMRAFHEDAEVQLSFQLQINVPVR

VLE
```

-continued

PDGFR(D1-D5)9G-Fc amino acid sequence with secretory peptide (underlined)
(SEQ ID NO: 9)
<u>MRLPGAMPALALKGELLLLSLLLLLEPQISQ</u>GLVVTPPGPELVLNVSSTFVLTCSGSAPV

VWERMSQEPPQEMAKAQDGTFSSVLTLTNLTGLDTGEYFCTHNDSRGLETDERKRLYIF

VPDPTVGFLPNDAEELFIFLTEITEITIPCRVTDPQLVVTLHEKKGDVALPVPYDHQRGFF

GIFEDRSYICKTTIGDREVDSDAYYVYRLQVSSINVSVNAVQTVVRQGENITLMCIVIGN

EVVNFEWTYPRKESGRLVEPVTDFLLDMPYHIRSILHIPSAELEDSGTYTCNVTESVNDH

QDEKAINITVVESGYVRLLGEVGTLQFAELHRSRTLQVVFEAYPPPTVLWFKDNRTLGD

SSAGEIALSTRNVSETRYVSELTLVRVKVAEAGHYTMRAFHEDAEVQLSFQLQINVPVR

VLELSESHPDSGEQTVRCRGRGMPQPNIIWSACRDLKRCPRELPPTLLGNSSEEESQLET

NVTYWEEEQEFEVVSTLRLQHVDRPLSVRCTLRNAVGQDTQEVIVVPHSLPFKGGGGG

GGGGPKSCDKTHTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYTQKSLSLSPG

K

PDGFR(D1-D3)9G-Fc amino acid sequence with secretory peptide (underlined)
(SEQ ID NO: 10)
<u>MRLPGAMPALALKGELLLLSLLLLLEPQISQ</u>GLVVTPPGPELVLNVSSTFVLTCSGSAPV

VWERMSQEPPQEMAKAQDGTFSSVLTLTNLTGLDTGEYFCTHNDSRGLETDERKRLYIF

VPDPTVGFLPNDAEELFIFLTEITEITIPCRVTDPQLVVTLHEKKGDVALPVPYDHQRGFF

GIFEDRSYICKTTIGDREVDSDAYYVYRLQVSSINVSVNAVQTVVRQGENITLMCIVIGN

EVVNFEWTYPRKESGRLVEPVTDFLLDMPYHIRSILHIPSAELEDSGTYTCNVTESVNDH

QDEKAINITVVESGYGGGGGGGGGPKSCDKTHTCPPCPAPELLGGPSVFLFPPKPKDTL

MISRTPEVTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSV

MHEALHNHYTQKSLSLSPGK

PDGFR(D1-D2)9G-Fc amino acid sequence with secretory peptide (underlined)
(SEQ ID NO: 11)
<u>MRLPGAMPALALKGELLLLSLLLLLEPQISQ</u>GLVVTPPGPELVLNVSSTFVLTCSGSAPV

VWERMSQEPPQEMAKAQDGTFSSVLTLTNLTGLDTGEYFCTHNDSRGLETDERKRLYIF

VPDPTVGFLPNDAEELFIFLTEITEITIPCRVTDPQLVVTLHEKKGDVALPVPYDHQRGFF

GIFEDRSYICKTTIGDREVDSDAYYVYRLQVSSGGGGGGGGGPKSCDKTHTCPPCPAPEL

LGGPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDGSFFLYSKLTV

DKSRWQQGNVFSCSVMHEALHNHYTQKSLSLSPGK

Hybrid 1 amino acid sequence
(SEQ ID NO: 12)
MVSYWDTGVLLCALLSCLLLTGSGRPFVEMYSEIPEIIHMTEGRELVIPCRVTSPNITVTL

KKFPLDTLIPDGKRIIWDSRKGFIISNATYKEIGLLTCEATVNGHLYKTNYLTHRQTSSSSS

SSSSQISQGLVVTPPGPELVLNVSSTFVLTCSGSAPVVWERMSQEPPQEMAKAQDGTFSS

-continued

VLTLTNLTGLDTGEYFCTHNDSRGLETDERKRLYIFVPDPTVGFLPNDAEELFIFLTEITEI

TIPCRVTDPQLVVTLHEKKGDVALPVPYDHQRGFFGIFEDRSYICKTTIGDREVDSDAYY

VYRLQVSSINVSVNAVQTVVRQGENITLMCIVIGNEVVNFEWTYPRKESGRLVEPVTDF

LLDMPYHIRSILHIPSAELEDSGTYTCNVTESVNDHQDEKAINITVVESGYVRLLGEVGTL

QFAELHRSRTLQVVFEAYPPPTVLWFKDNRTLGDSSAGEIALSTRNVSETRYVSELTLVR

VKVAEAGHYTMRAFHEDAEVQLSFQLQINVPVRVLELSESHPDSGEQTVRCRGRGMPQ

PNIIWSACRDLKRCPRELPPTLLGNSSEEESQLETNVTYWEEEQEFEVVSTLRLQHVDRP

LSVRCTLRNAVGQDTQEVIVVPHSLPFTGGGGGGGGGPKSCDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFFLYSKLTVDK

SRWQQGNVFSCSVMHEALHNHYTQKSLSLSPGK

Hybrid 2 amino acid sequence
(SEQ ID NO: 13)
MRLPGAMPALALKGELLLLSLLLLLEPQISQGLVVTPPGPELVLNVSSTFVLTCSGSAPV

VWERMSQEPPQEMAKAQDGTFSSVLTLTNLTGLDTGEYFCTHNDSRGLETDERKRLYIF

VPDPTVGFLPNDAEELFIFLTEITEITIPCRVTDPQLVVTLHEKKGDVALPVPYDHQRGFF

GIFEDRSYICKTTIGDREVDSDAYYVYRLQVSSINVSVNAVQTVVRQGENITLMCIVIGN

EVVNFEWTYPRKESGRLVEPVTDFLLDMPYHIRSILHIPSAELEDSGTYTCNVTESVNDH

QDEKAINITVVESGYVRLLGEVGTLQFAELHRSRTLQVVFEAYPPPTVLWFKDNRTLGD

SSAGEIALSTRNVSETRYVSELTLVRVKVAEAGHYTMRAFHEDAEVQLSFQLQINVPVR

VLELSESHPDSGEQTVRCRGRGMPQPNIIWSACRDLKRCPRELPPTLLGNSSEEESQLET

NVTYWEEEQEFEVVSTLRLQHVDRPLSVRCTLRNAVGQDTQEVIVVPHSLPFSSSSSSSS

SRPFVEMYSEIPEIIHMTEGRELVIPCRVTSPNITVTLKKFPLDTLIPDGKRIIWDSRKGFIIS

NATYKEIGLLTCEATVNGHLYKTNYLTHRQTGGGGGGGGGPKSCDKTHTCPPCPAPEL

LGGPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDGSFFLYSKLTV

DKSRWQQGNVFSCSVMHEALHNHYTQKSLSLSPGK

Hybrid 3 amino acid sequence
(SEQ ID NO: 14)
MVSYWDTGVLLCALLSCLLLTGSGRPFVEMYSEIPEIIHMTEGRELVIPCRVTSPNITVTL

KKFPLDTLIPDGKRIIWDSRKGFIISNATYKEIGLLTCEATVNGHLYKTNYLTHRQTSSSSS

SSSSQISQGLVVTPPGPELVLNVSSTFVLTCSGSAPVVWERMSQEPPQEMAKAQDGTFSS

VLTLTNLTGLDTGEYFCTHNDSRGLETDERKRLYIFVPDPTVGFLPNDAEELFIFLTEITEI

TIPCRVTDPQLVVTLHEKKGDVALPVPYDHQRGFFGIFEDRSYICKTTIGDREVDSDAYY

VYRLQVSSINVSVNAVQTVVRQGENITLMCIVIGNEVVNFEWTYPRKESGRLVEPVTDF

LLDMPYHIRSILHIPSAELEDSGTYTCNVTESVNDHQDEKAINITVVESGYTGGGGGGG

GPKSCDKTHTCPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKSLSLSPGK

-continued

Hybrid 4 amino acid sequence
(SEQ ID NO: 15)

MRLPGAMPALALKGELLLLSLLLLLEPQISQGLVVTPPGPELVLNVSSTFVLTCSGSAPV

VWERMSQEPPQEMAKAQDGTFSSVLTLTNLTGLDTGEYFCTHNDSRGLETDERKRLYIF

VPDPTVGFLPNDAEELFIFLTEITEITIPCRVTDPQLVVTLHEKKGDVALPVPYDHQRGFF

GIFEDRSYICKTTIGDREVDSDAYYVYRLQVSSINVSVNAVQTVVRQGENITLMCIVIGN

EVVNFEWTYPRKESGRLVEPVTDFLLDMPYHIRSILHIPSAELEDSGTYTCNVTESVNDH

QDEKAINITVVESGYSSSSSSSSSRPFVEMYSEIPEIIHMTEGRELVIPCRVTSPNITVTLKK

FPLDTLIPDGKRIIWDSRKGFIISNATYKEIGLLTCEATVNGHLYKTNYLTHRQTGGGGG

GGGGPKSCDKTHTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYTQKSLSLSPG

K

PDGFR(D1-D5) open reading frame
(SEQ ID NO: 16)

ATGCGGCTTCCGGGTGCGATGCCAGCTCTGGCCCTCAAAGGCGAGCTGCTGTTGCTG

TCTCTCCTGTTACTTCTGGAACCACAGATCTCTCAGGGCCTGGTCGTCACACCCCCG

GGGCCAGAGCTTGTCCTCAATGTCTCCAGCACCTTCGTTCTGACCTGCTCGGGTTCA

GCTCCGGTGGTGTGGGAACGGATGTCCCAGGAGCCCCCACAGGAAATGGCCAAGGC

CCAGGATGGCACCTTCTCCAGCGTGCTCACACTGACCAACCTCACTGGGCTAGACAC

GGGAGAATACTTTTGCACCCACAATGACTCCCGTGGACTGGAGACCGATGAGCGGA

AACGGCTCTACATCTTTGTGCCAGATCCCACCGTGGGCTTCCTCCCTAATGATGCCG

AGGAACTATTCATCTTTCTCACGGAAATAACTGAGATCACCATTCCATGCCGAGTAA

CAGACCCACAGCTGGTGGTGACACTGCACGAGAAGAAAGGGGACGTTGCACTGCCT

GTCCCCTATGATCACCAACGTGGCTTTTTTGGTATCTTTGAGGACAGAAGCTACATCT

GCAAAACCACCATTGGGGACAGGGAGGTGGATTCTGATGCCTACTATGTCTACAGA

CTCCAGGTGTCATCCATCAACGTCTCTGTGAACGCAGTGCAGACTGTGGTCCGCCAG

GGTGAGAACATCACCCTCATGTGCATTGTGATCGGGAATGAGGTGGTCAACTTCGAG

TGGACATACCCCCGCAAAGAAAGTGGGCGGCTGGTGGAGCCGGTGACTGACTTCCT

CTTGGATATGCCTTACCACATCCGCTCCATCCTGCACATCCCCAGTGCCGAGTTAGA

AGACTCGGGGACCTACACCTGCAATGTGACGGAGAGTGTGAATGACCATCAGGATG

AAAAGGCCATCAACATCACCGTGGTTGAGAGCGGCTACGTGCGGCTCCTGGGAGAG

GTGGGCACACTACAATTTGCTGAGCTGCATCGGAGCCGGACACTGCAGGTAGTGTTC

GAGGCCTACCCACCGCCCACTGTCCTGTGGTTCAAAGACAACCGCACCCTGGGCGA

CTCCAGCGCTGGCGAAATCGCCCTGTCCACGCGCAACGTGTCGGAGACCCGGTATGT

GTCAGAGCTGACACTGGTTCGCGTGAAGGTGGCAGAGGCTGGCCACTACACCATGC

GGGCCTTCCATGAGGATGCTGAGGTCCAGCTCTCCTTCCAGCTACAGATCAATGTCC

CTGTCCGAGTGCTGGAGCTAAGTGAGAGCCACCCTGACAGTGGGGAACAGACAGTC

CGCTGTCGTGGCCGGGGCATGCCCCAGCCGAACATCATCTGGTCTGCCTGCAGAGAC

CTCAAAAGGTGTCCACGTGAGCTGCCGCCCACGCTGCTGGGGAACAGTTCCGAAGA

GGAGAGCCAGCTGGAGACTAACGTGACGTACTGGGAGGAGGAGCAGGAGTTTGAG

GTGGTGAGCACACTGCGTCTGCAGCACGTGGATCGGCCACTGTCGGTGCGCTGCAC

-continued

GCTGCGCAACGCTGTGGGCCAGGACACGCAGGAGGTCATCGTGGTGCCACACTCCT

TGCCCTTTTAA

PDGFR(D1-D4) open reading frame
(SEQ ID NO: 17)
ATGCGGCTTCCGGGTGCGATGCCAGCTCTGGCCCTCAAAGGCGAGCTGCTGTTGCTG

TCTCTCCTGTTACTTCTGGAACCACAGATCTCTCAGGGCCTGGTCGTCACACCCCCG

GGGCCAGAGCTTGTCCTCAATGTCTCCAGCACCTTCGTTCTGACCTGCTCGGGTTCA

GCTCCGGTGGTGTGGGAACGGATGTCCCAGGAGCCCCCACAGGAAATGGCCAAGGC

CCAGGATGGCACCTTCTCCAGCGTGCTCACACTGACCAACCTCACTGGGCTAGACAC

GGGAGAATACTTTTGCACCCACAATGACTCCCGTGGACTGGAGACCGATGAGCGGA

AACGGCTCTACATCTTTGTGCCAGATCCCACCGTGGGCTTCCTCCCTAATGATGCCG

AGGAACTATTCATCTTTCTCACGGAAATAACTGAGATCACCATTCCATGCCGAGTAA

CAGACCCACAGCTGGTGGTGACACTGCACGAGAAGAAAGGGGACGTTGCACTGCCT

GTCCCCTATGATCACCAACGTGGCTTTTTTGGTATCTTTGAGGACAGAAGCTACATCT

GCAAAACCACCATTGGGGACAGGGAGGTGGATTCTGATGCCTACTATGTCTACAGA

CTCCAGGTGTCATCCATCAACGTCTCTGTGAACGCAGTGCAGACTGTGGTCCGCCAG

GGTGAGAACATCACCCTCATGTGCATTGTGATCGGGAATGAGGTGGTCAACTTCGAG

TGGACATACCCCCGCAAAGAAAGTGGGCGGCTGGTGGAGCCGGTGACTGACTTCCT

CTTGGATATGCCTTACCACATCCGCTCCATCCTGCACATCCCCAGTGCCGAGTTAGA

AGACTCGGGGACCTACACCTGCAATGTGACGGAGAGTGTGAATGACCATCAGGATG

AAAAGGCCATCAACATCACCGTGGTTGAGAGCGGCTACGTGCGGCTCCTGGGAGAG

GTGGGCACACTACAATTTGCTGAGCTGCATCGGAGCCGGACACTGCAGGTAGTGTTC

GAGGCCTACCCACCGCCCACTGTCCTGTGGTTCAAAGACAACCGCACCCTGGGCGA

CTCCAGCGCTGGCGAAATCGCCCTGTCCACGCGCAACGTGTCGGAGACCCGGTATGT

GTCAGAGCTGACACTGGTTCGCGTGAAGGTGGCAGAGGCTGGCCACTACACCATGC

GGGCCTTCCATGAGGATGCTGAGGTCCAGCTCTCCTTCCAGCTACAGATCAATGTCC

CTGTCCGAGTGCTGGAGTAG

PDGFR(D1-D5)9G-Fc open reading frame
(SEQ ID NO: 18)
ATGCGGCTTCCGGGTGCGATGCCAGCTCTGGCCCTCAAAGGCGAGCTGCTGTTGCTG

TCTCTCCTGTTACTTCTGGAACCACAGATCTCTCAGGGCCTGGTCGTCACACCCCCG

GGGCCAGAGCTTGTCCTCAATGTCTCCAGCACCTTCGTTCTGACCTGCTCGGGTTCA

GCTCCGGTGGTGTGGGAACGGATGTCCCAGGAGCCCCCACAGGAAATGGCCAAGGC

CCAGGATGGCACCTTCTCCAGCGTGCTCACACTGACCAACCTCACTGGGCTAGACAC

GGGAGAATACTTTTGCACCCACAATGACTCCCGTGGACTGGAGACCGATGAGCGGA

AACGGCTCTACATCTTTGTGCCAGATCCCACCGTGGGCTTCCTCCCTAATGATGCCG

AGGAACTATTCATCTTTCTCACGGAAATAACTGAGATCACCATTCCATGCCGAGTAA

CAGACCCACAGCTGGTGGTGACACTGCACGAGAAGAAAGGGGACGTTGCACTGCCT

GTCCCCTATGATCACCAACGTGGCTTTTTTGGTATCTTTGAGGACAGAAGCTACATCT

GCAAAACCACCATTGGGGACAGGGAGGTGGATTCTGATGCCTACTATGTCTACAGA

CTCCAGGTGTCATCCATCAACGTCTCTGTGAACGCAGTGCAGACTGTGGTCCGCCAG

GGTGAGAACATCACCCTCATGTGCATTGTGATCGGGAATGAGGTGGTCAACTTCGAG

TGGACATACCCCCGCAAAGAAAGTGGGCGGCTGGTGGAGCCGGTGACTGACTTCCT

-continued

```
CTTGGATATGCCTTACCACATCCGCTCCATCCTGCACATCCCCAGTGCCGAGTTAGA

AGACTCGGGGACCTACACCTGCAATGTGACGGAGAGTGTGAATGACCATCAGGATG

AAAAGGCCATCAACATCACCGTGGTTGAGAGCGGCTACGTGCGGCTCCTGGGAGAG

GTGGGCACACTACAATTTGCTGAGCTGCATCGGAGCCGGACACTGCAGGTAGTGTTC

GAGGCCTACCCACCGCCCACTGTCCTGTGGTTCAAAGACAACCGCACCCTGGGCGA

CTCCAGCGCTGGCGAAATCGCCCTGTCCACGCGCAACGTGTCGGAGACCCGGTATGT

GTCAGAGCTGACACTGGTTCGCGTGAAGGTGGCAGAGGCTGGCCACTACACCATGC

GGGCCTTCCATGAGGATGCTGAGGTCCAGCTCTCCTTCCAGCTACAGATCAATGTCC

CTGTCCGAGTGCTGGAGCTAAGTGAGAGCCACCCTGACAGTGGGGAACAGACAGTC

CGCTGTCGTGGCCGGGGCATGCCCCAGCCGAACATCATCTGGTCTGCCTGCAGAGAC

CTCAAAAGGTGTCCACGTGAGCTGCCGCCCACGCTGCTGGGGAACAGTTCCGAAGA

GGAGAGCCAGCTGGAGACTAACGTGACGTACTGGGAGGAGGAGCAGGAGTTTGAG

GTGGTGAGCACACTGCGTCTGCAGCACGTGGATCGGCCACTGTCGGTGCGCTGCAC

GCTGCGCAACGCTGTGGGCCAGGACACGCAGGAGGTCATCGTGGTGCCACACTCCT

TGCCCTTTACCGGTGGAGGTGGAGGTGGAGGTGGAGGTCCTAAATCTTGTGACAAA

ACTCACACATGCCCACCGTGCCCAGCACCTGAACTCCTGGGGGGACCGTCAGTCTTC

CTCTTCCCCCCAAAACCCAAGGACACCCTCATGATCTCCCGGACCCCTGAGGTCACA

TGCGTGGTGGTGGACGTGAGCCACGAAGACCCTGAGGTCAAGTTCAACTGGTACGT

GGACGGCGTGGAGGTGCATAATGCCAAGACAAAGCCGCGGGAGGAGCAGTACAAC

AGCACGTACCGTGTGGTCAGCGTCCTCACCGTCCTGCACCAGGACTGGCTGAATGGC

AAGGAGTACAAGTGCAAGGTCTCCAACAAAGCCCTCCCAGCCCCCATCGAGAAAAC

CATCTCCAAAGCCAAAGGGCAGCCCCGAGAACCACAGGTGTACACCCTGCCCCCAT

CCCGGGATGAGCTGACCAAGAACCAGGTCAGCCTGACCTGCCTGGTCAAAGGCTTC

TATCCCAGCGACATCGCCGTGGAGTGGGAGAGCAATGGGCAGCCGGAGAACAACTA

CAAGACCACGCCTCCCGTGCTGGACTCCGACGGCTCCTTCTTCCTCTACAGCAAGCT

CACCGTGGACAAGAGCAGGTGGCAGCAGGGGAACGTCTTCTCATGCTCCGTGATGC

ATGAGGCTCTGCACAACCACTACACGCAGAAGAGCCTCTCCCTGTCTCCGGGTAAAT

AG
```

PDGFR(D1-D3)9G-Fc open reading frame (SEQ ID NO: 19)

```
ATGCGGCTTCCGGGTGCGATGCCAGCTCTGGCCCTCAAAGGCGAGCTGCTGTTGCTG

TCTCTCCTGTTACTTCTGGAACCACAGATCTCTCAGGGCCTGGTCGTCACACCCCCG

GGGCCAGAGCTTGTCCTCAATGTCTCCAGCACCTTCGTTCTGACCTGCTCGGGTTCA

GCTCCGGTGGTGTGGGAACGGATGTCCCAGGAGCCCCCACAGGAAATGGCCAAGGC

CCAGGATGGCACCTTCTCCAGCGTGCTCACACTGACCAACCTCACTGGGCTAGACAC

GGGAGAATACTTTTGCACCCACAATGACTCCCGTGGACTGGAGACCGATGAGCGGA

AACGGCTCTACATCTTTGTGCCAGATCCCACCGTGGGCTTCCTCCCTAATGATGCCG

AGGAACTATTCATCTTTCTCACGGAAATAACTGAGATCACCATTCCATGCCGAGTAA

CAGACCCACAGCTGGTGGTGACACTGCACGAGAAGAAAGGGGACGTTGCACTGCCT

GTCCCCTATGATCACCAACGTGGCTTTTTTGGTATCTTTGAGGACAGAAGCTACATCT

GCAAAACCACCATTGGGGACAGGGAGGTGGATTCTGATGCCTACTATGTCTACAGA

CTCCAGGTGTCATCCATCAACGTCTCTGTGAACGCAGTGCAGACTGTGGTCCGCCAG
```

-continued

```
GGTGAGAACATCACCCTCATGTGCATTGTGATCGGGAATGAGGTGGTCAACTTCGAG

TGGACATACCCCCGCAAAGAAAGTGGGCGGCTGGTGGAGCCGGTGACTGACTTCCT

CTTGGATATGCCTTACCACATCCGCTCCATCCTGCACATCCCCAGTGCCGAGTTAGA

AGACTCGGGGACCTACACCTGCAATGTGACGGAGAGTGTGAATGACCATCAGGATG

AAAAGGCCATCAACATCACCGTGGTTGAGAGCGGCTACACCGGTGGAGGTGGAGGT

GGAGGTGGAGGTCCTAAATCTTGTGACAAAACTCACACATGCCCACCGTGCCCAGC

ACCTGAACTCCTGGGGGACCGTCAGTCTTCCTCTTCCCCCCAAAACCCAAGGACAC

CCTCATGATCTCCCGGACCCCTGAGGTCACATGCGTGGTGGTGGACGTGAGCCACGA

AGACCCTGAGGTCAAGTTCAACTGGTACGTGGACGGCGTGGAGGTGCATAATGCCA

AGACAAAGCCGCGGGAGGAGCAGTACAACAGCACGTACCGTGTGGTCAGCGTCCTC

ACCGTCCTGCACCAGGACTGGCTGAATGGCAAGGAGTACAAGTGCAAGGTCTCCAA

CAAAGCCCTCCCAGCCCCCATCGAGAAAACCATCTCCAAAGCCAAAGGGCAGCCCC

GAGAACCACAGGTGTACACCCTGCCCCCATCCCGGGATGAGCTGACCAAGAACCAG

GTCAGCCTGACCTGCCTGGTCAAAGGCTTCTATCCCAGCGACATCGCCGTGGAGTGG

GAGAGCAATGGGCAGCCGGAGAACAACTACAAGACCACGCCTCCCGTGCTGGACTC

CGACGGCTCCTTCTTCCTCTACAGCAAGCTCACCGTGGACAAGAGCAGGTGGCAGC

AGGGGAACGTCTTCTCATGCTCCGTGATGCATGAGGCTCTGCACAACCACTACACGC

AGAAGAGCCTCTCCCTGTCTCCGGGTAAATAG
```

PDGFR(D1-D2)9G-Fc open reading frame
(SEQ ID NO: 20)
```
ATGCGGCTTCCGGGTGCGATGCCAGCTCTGGCCCTCAAAGGCGAGCTGCTGTTGCTG

TCTCTCCTGTTACTTCTGGAACCACAGATCTCTCAGGGCCTGGTCGTCACACCCCCG

GGGCCAGAGCTTGTCCTCAATGTCTCCAGCACCTTCGTTCTGACCTGCTCGGGTTCA

GCTCCGGTGGTGTGGGAACGGATGTCCCAGGAGCCCCCACAGGAAATGGCCAAGGC

CCAGGATGGCACCTTCTCCAGCGTGCTCACACTGACCAACCTCACTGGGCTAGACAC

GGGAGAATACTTTTGCACCCACAATGACTCCCGTGGACTGGAGACCGATGAGCGGA

AACGGCTCTACATCTTTGTGCCAGATCCCACCGTGGGCTTCCTCCCTAATGATGCCG

AGGAACTATTCATCTTTCTCACGGAAATAACTGAGATCACCATTCCATGCCGAGTAA

CAGACCCACAGCTGGTGGTGACACTGCACGAGAAGAAGGGGACGTTGCACTGCCT

GTCCCCTATGATCACCAACGTGGCTTTTTTGGTATCTTTGAGGACAGAAGCTACATCT

GCAAAACCACCATTGGGGACAGGGAGGTGGATTCTGATGCCTACTATGTCTACAGA

CTCCAGGTGTCATCCACCGGTGGAGGTGGAGGTGGAGGTGGAGGTCCTAAATCTTGT

GACAAAACTCACACATGCCCACCGTGCCCAGCACCTGAACTCCTGGGGGACCGTC

AGTCTTCCTCTTCCCCCCAAAACCCAAGGACACCCTCATGATCTCCCGGACCCCTGA

GGTCACATGCGTGGTGGTGGACGTGAGCCACGAAGACCCTGAGGTCAAGTTCAACT

GGTACGTGGACGGCGTGGAGGTGCATAATGCCAAGACAAAGCCGCGGGAGGAGCA

GTACAACAGCACGTACCGTGTGGTCAGCGTCCTCACCGTCCTGCACCAGGACTGGCT

GAATGGCAAGGAGTACAAGTGCAAGGTCTCCAACAAAGCCCTCCCAGCCCCCATCG

AGAAAACCATCTCCAAAGCCAAAGGGCAGCCCCGAGAACCACAGGTGTACACCCTG

CCCCCATCCCGGGATGAGCTGACCAAGAACCAGGTCAGCCTGACCTGCCTGGTCAA

AGGCTTCTATCCCAGCGACATCGCCGTGGAGTGGGAGAGCAATGGGCAGCCGGAGA

ACAACTACAAGACCACGCCTCCCGTGCTGGACTCCGACGGCTCCTTCTTCCTCTACA
```

-continued

```
GCAAGCTCACCGTGGACAAGAGCAGGTGGCAGCAGGGGAACGTCTTCTCATGCTCC

GTGATGCATGAGGCTCTGCACAACCACTACACGCAGAAGAGCCTCTCCCTGTCTCCG

GGTAAATAG
```

Hybrid 1 open reading frame (SEQ ID NO: 21)
```
ATGGTCAGCTACTGGGACACCGGGGTCCTGCTGTGCGCGCTGCTCAGCTGTCTGCTT

CTCACAGGATCTGGTAGACCTTTCGTAGAGATGTACAGTGAAATCCCCGAAATTATA

CACATGACTGAAGGAAGGGAGCTCGTCATTCCCTGCCGGGTTACGTCACCTAACATC

ACTGTTACTTTAAAAAAGTTTCCACTTGACACTTTGATCCCTGATGGAAAACGCATA

ATCTGGGACAGTAGAAAGGGCTTCATCATATCAAATGCAACGTACAAAGAAATAGG

GCTTCTGACCTGTGAAGCAACAGTCAATGGGCATTTGTATAAGACAAACTATCTCAC

ACATCGACAAACCTCGAGTTCCAGCTCCTCTTCCTCAAGCCAGATCTCTCAGGGCCT

GGTCGTCACACCCCGGGGCCAGAGCTTGTCCTCAATGTCTCCAGCACCTTCGTTCT

GACCTGCTCGGGTTCAGCTCCGGTGGTGTGGGAACGGATGTCCCAGGAGCCCCCAC

AGGAAATGGCCAAGGCCCAGGATGGCACCTTCTCCAGCGTGCTCACACTGACCAAC

CTCACTGGGCTAGACACGGGAGAATACTTTTGCACCCACAATGACTCCCGTGGACTG

GAGACCGATGAGCGGAAACGGCTCTACATCTTTGTGCCAGATCCCACCGTGGGCTTC

CTCCCTAATGATGCCGAGGAACTATTCATCTTTCTCACGGAAATAACTGAGATCACC

ATTCCATGCCGAGTAACAGACCCACAGCTGGTGGTGACACTGCACGAGAAGAAAGG

GGACGTTGCACTGCCTGTCCCCTATGATCACCAACGTGGCTTTTTTGGTATCTTTGAG

GACAGAAGCTACATCTGCAAAACCACCATTGGGGACAGGGAGGTGGATTCTGATGC

CTACTATGTCTACAGACTCCAGGTGTCATCCATCAACGTCTCTGTGAACGCAGTGCA

GACTGTGGTCCGCCAGGGTGAGAACATCACCCTCATGTGCATTGTGATCGGGAATGA

GGTGGTCAACTTCGAGTGGACATACCCCCGCAAAGAAAGTGGGCGGCTGGTGGAGC

CGGTGACTGACTTCCTCTTGGATATGCCTTACCACATCCGCTCCATCCTGCACATCCC

CAGTGCCGAGTTAGAAGACTCGGGGACCTACACCTGCAATGTGACGGAGAGTGTGA

ATGACCATCAGGATGAAAAGGCCATCAACATCACCGTGGTTGAGAGCGGCTACGTG

CGGCTCCTGGGAGAGGTGGGCACACTACAATTTGCTGAGCTGCATCGGAGCCGGAC

ACTGCAGGTAGTGTTCGAGGCCTACCCACCGCCCACTGTCCTGTGGTTCAAAGACAA

CCGCACCCTGGGCGACTCCAGCGCTGGCGAAATCGCCCTGTCCACGCGCAACGTGTC

GGAGACCCGGTATGTGTCAGAGCTGACACTGGTTCGCGTGAAGGTGGCAGAGGCTG

GCCACTACACCATGCGGGCCTTCCATGAGGATGCTGAGGTCCAGCTCTCCTTCCAGC

TACAGATCAATGTCCCTGTCCGAGTGCTGGAGCTAAGTGAGAGCCACCCTGACAGTG

GGGAACAGACAGTCCGCTGTCGTGGCCGGGGCATGCCCCAGCCGAACATCATCTGG

TCTGCCTGCAGAGACCTCAAAAGGTGTCCACGTGAGCTGCCGCCCACGCTGCTGGG

GAACAGTTCCGAAGAGGAGAGCCAGCTGGAGACTAACGTGACGTACTGGGAGGAG

GAGCAGGAGTTTGAGGTGGTGAGCACACTGCGTCTGCAGCACGTGGATCGGCCACT

GTCGGTGCGCTGCACGCTGCGCAACGCTGTGGGCCAGGACACGCAGGAGGTCATCG

TGGTGCCACACTCCTTGCCCTTTACCGGTGGAGGTGGAGGTGGAGGTGGAGGTCCTA

AATCTTGTGACAAAACTCACACATGCCCACCGTGCCCAGCACCTGAACTCCTGGGGG

GACCGTCAGTCTTCCTCTTCCCCCCAAAACCCAAGGACACCCTCATGATCTCCCGGA

CCCCTGAGGTCACATGCGTGGTGGTGGACGTGAGCCACGAAGACCCTGAGGTCAAG
```

-continued

```
TTCAACTGGTACGTGGACGGCGTGGAGGTGCATAATGCCAAGACAAAGCCGCGGGA

GGAGCAGTACAACAGCACGTACCGTGTGGTCAGCGTCCTCACCGTCCTGCACCAGG

ACTGGCTGAATGGCAAGGAGTACAAGTGCAAGGTCTCCAACAAAGCCCTCCCAGCC

CCCATCGAGAAAACCATCTCCAAAGCCAAAGGGCAGCCCCGAGAACCACAGGTGTA

CACCCTGCCCCCATCCCGGGATGAGCTGACCAAGAACCAGGTCAGCCTGACCTGCCT

GGTCAAAGGCTTCTATCCCAGCGACATCGCCGTGGAGTGGGAGAGCAATGGGCAGC

CGGAGAACAACTACAAGACCACGCCTCCCGTGCTGGACTCCGACGGCTCCTTCTTCC

TCTACAGCAAGCTCACCGTGGACAAGAGCAGGTGGCAGCAGGGGAACGTCTTCTCA

TGCTCCGTGATGCATGAGGCTCTGCACAACCACTACACGCAGAAGAGCCTCTCCCTG

TCTCCGGGTAAATAG
```

Hybrid 2 open reading frame (SEQ ID NO: 22)
```
ATGCGGCTTCCGGGTGCGATGCCAGCTCTGGCCCTCAAAGGCGAGCTGCTGTTGCTG

TCTCTCCTGTTACTTCTGGAACCACAGATCTCTCAGGGCCTGGTCGTCACACCCCCG

GGGCCAGAGCTTGTCCTCAATGTCTCCAGCACCTTCGTTCTGACCTGCTCGGGTTCA

GCTCCGGTGGTGTGGGAACGGATGTCCCAGGAGCCCCCACAGGAAATGGCCAAGGC

CCAGGATGGCACCTTCTCCAGCGTGCTCACACTGACCAACCTCACTGGGCTAGACAC

GGGAGAATACTTTTGCACCCACAATGACTCCCGTGGACTGGAGACCGATGAGCGGA

AACGGCTCTACATCTTTGTGCCAGATCCCACCGTGGGCTTCCTCCCTAATGATGCCG

AGGAACTATTCATCTTTCTCACGGAAATAACTGAGATCACCATTCCATGCCGAGTAA

CAGACCCACAGCTGGTGGTGACACTGCACGAGAAGAAAGGGGACGTTGCACTGCCT

GTCCCCTATGATCACCAACGTGGCTTTTTTGGTATCTTTGAGGACAGAAGCTACATCT

GCAAAACCACCATTGGGGACAGGGAGGTGGATTCTGATGCCTACTATGTCTACAGA

CTCCAGGTGTCATCCATCAACGTCTCTGTGAACGCAGTGCAGACTGTGGTCCGCCAG

GGTGAGAACATCACCCTCATGTGCATTGTGATCGGGAATGAGGTGGTCAACTTCGAG

TGGACATACCCCCGCAAAGAAAGTGGGCGGCTGGTGGAGCCGGTGACTGACTTCCT

CTTGGATATGCCTTACCACATCCGCTCCATCCTGCACATCCCCAGTGCCGAGTTAGA

AGACTCGGGGACCTACACCTGCAATGTGACGGAGAGTGTGAATGACCATCAGGATG

AAAAGGCCATCAACATCACCGTGGTTGAGAGCGGCTACGTGCGGCTCCTGGGAGAG

GTGGGCACACTACAATTTGCTGAGCTGCATCGGAGCCGGACACTGCAGGTAGTGTTC

GAGGCCTACCCACCGCCCACTGTCCTGTGGTTCAAAGACAACCGCACCCTGGGCGA

CTCCAGCGCTGGCGAAATCGCCCTGTCCACGCGCAACGTGTCGGAGACCCGGTATGT

GTCAGAGCTGACACTGGTTCGCGTGAAGGTGGCAGAGGCTGGCCACTACACCATGC

GGGCCTTCCATGAGGATGCTGAGGTCCAGCTCTCCTTCCAGCTACAGATCAATGTCC

CTGTCCGAGTGCTGGAGCTAAGTGAGAGCCACCCTGACAGTGGGGAACAGACAGTC

CGCTGTCGTGGCCGGGGCATGCCCCAGCCGAACATCATCTGGTCTGCCTGCAGAGAC

CTCAAAAGGTGTCCACGTGAGCTGCCGCCCACGCTGCTGGGGAACAGTTCCGAAGA

GGAGAGCCAGCTGGAGACTAACGTGACGTACTGGGAGGAGGAGCAGGAGTTTGAG

GTGGTGAGCACACTGCGTCTGCAGCACGTGGATCGGCCACTGTCGGTGCGCTGCAC

GCTGCGCAACGCTGTGGGCCAGGACACGCAGGAGGTCATCGTGGTGCCACACTCCT

TGCCCTTTAGTTCCAGCTCCTCTTCCTCAAGCTCGCCTTTCGTAGAGATGTACAGTGA
```

-continued

```
AATCCCGAAATTATACACATGACTGAAGGAAGGGAGCTCGTCATTCCCTGCCGGGT

TACGTCACCTAACATCACTGTTACTTTAAAAAAGTTTCCACTTGACACTTTGATCCCT

GATGGAAAACGCATAATCTGGGACAGTAGAAAGGGCTTCATCATATCAAATGCAAC

GTACAAAGAAATAGGGCTTCTGACCTGTGAAGCAACAGTCAATGGGCATTTGTATA

AGACAAACTATCTCACACATCGACAAACCGGTGGAGGTGGAGGTGGAGGTGGAGGT

CCTAAATCTTGTGACAAAACTCACACATGCCCACCGTGCCCAGCACCTGAACTCCTG

GGGGGACCGTCAGTCTTCCTCTTCCCCCCAAAACCCAAGGACACCCTCATGATCTCC

CGGACCCCTGAGGTCACATGCGTGGTGGTGGACGTGAGCCACGAAGACCCTGAGGT

CAAGTTCAACTGGTACGTGGACGGCGTGGAGGTGCATAATGCCAAGACAAAGCCGC

GGGAGGAGCAGTACAACAGCACGTACCGTGTGGTCAGCGTCCTCACCGTCCTGCAC

CAGGACTGGCTGAATGGCAAGGAGTACAAGTGCAAGGTCTCCAACAAAGCCCTCCC

AGCCCCCATCGAGAAAACCATCTCCAAAGCCAAAGGGCAGCCCCGAGAACCACAGG

TGTACACCCTGCCCCCATCCCGGGATGAGCTGACCAAGAACCAGGTCAGCCTGACCT

GCCTGGTCAAAGGCTTCTATCCCAGCGACATCGCCGTGGAGTGGGAGAGCAATGGG

CAGCCGGAGAACAACTACAAGACCACGCCTCCCGTGCTGGACTCCGACGGCTCCTT

CTTCCTCTACAGCAAGCTCACCGTGGACAAGAGCAGGTGGCAGCAGGGGAACGTCT

TCTCATGCTCCGTGATGCATGAGGCTCTGCACAACCACTACACGCAGAAGAGCCTCT

CCCTGTCTCCGGGTAAATAG
```

Hybrid 3 open reading frame (SEQ ID NO: 23)
```
ATGGTCAGCTACTGGGACACCGGGGTCCTGCTGTGCGCGCTGCTCAGCTGTCTGCTT

CTCACAGGATCTGGTAGACCTTTCGTAGAGATGTACAGTGAAATCCCCGAAATTATA

CACATGACTGAAGGAAGGGAGCTCGTCATTCCCTGCCGGGTTACGTCACCTAACATC

ACTGTTACTTTAAAAAAGTTTCCACTTGACACTTTGATCCCTGATGGAAAACGCATA

ATCTGGGACAGTAGAAAGGGCTTCATCATATCAAATGCAACGTACAAAGAAATAGG

GCTTCTGACCTGTGAAGCAACAGTCAATGGGCATTTGTATAAGACAAACTATCTCAC

ACATCGACAAACCTCGAGTTCCAGCTCCTCTTCCTCAAGCCAGATCTCTCAGGGCCT

GGTCGTCACACCCCCGGGGCCAGAGCTTGTCCTCAATGTCTCCAGCACCTTCGTTCT

GACCTGCTCGGGTTCAGCTCCGGTGGTGTGGGAACGGATGTCCCAGGAGCCCCCAC

AGGAAATGGCCAAGGCCCAGGATGGCACCTTCTCCAGCGTGCTCACACTGACCAAC

CTCACTGGGCTAGACACGGGAGAATACTTTTGCACCCACAATGACTCCCGTGGACTG

GAGACCGATGAGCGGAAACGGCTCTACATCTTTGTGCCAGATCCCACCGTGGGCTTC

CTCCCTAATGATGCCGAGGAACTATTCATCTTTCTCACGGAAATAACTGAGATCACC

ATTCCATGCCGAGTAACAGACCCACAGCTGGTGGTGACACTGCACGAGAAGAAAGG

GGACGTTGCACTGCCTGTCCCCTATGATCACCAACGTGGCTTTTTTGGTATCTTTGAG

GACAGAAGCTACATCTGCAAAACCACCATTGGGGACAGGGAGGTGGATTCTGATGC

CTACTATGTCTACAGACTCCAGGTGTCATCCATCAACGTCTCTGTGAACGCAGTGCA

GACTGTGGTCCGCCAGGGTGAGAACATCACCCTCATGTGCATTGTGATCGGGAATGA

GGTGGTCAACTTCGAGTGGACATACCCCCGCAAAGAAAGTGGGCGGCTGGTGGAGC

CGGTGACTGACTTCCTCTTGGATATGCCTTACCACATCCGCTCCATCCTGCACATCCC

CAGTGCCGAGTTAGAAGACTCGGGGACCTACACCTGCAATGTGACGGAGAGTGTGA

ATGACCATCAGGATGAAAAGGCCATCAACATCACCGTGGTTGAGAGCGGCTACACC
```

-continued

```
GGTGGAGGTGGAGGTGGAGGTGGAGGTCCTAAATCTTGTGACAAAACTCACACATG

CCCACCGTGCCCAGCACCTGAACTCCTGGGGGACCGTCAGTCTTCCTCTTCCCCCC

AAAACCCAAGGACACCCTCATGATCTCCCGGACCCCTGAGGTCACATGCGTGGTGG

TGGACGTGAGCCACGAAGACCCTGAGGTCAAGTTCAACTGGTACGTGGACGGCGTG

GAGGTGCATAATGCCAAGACAAAGCCGCGGGAGGAGCAGTACAACAGCACGTACC

GTGTGGTCAGCGTCCTCACCGTCCTGCACCAGGACTGGCTGAATGGCAAGGAGTAC

AAGTGCAAGGTCTCCAACAAAGCCCTCCCAGCCCCCATCGAGAAAACCATCTCCAA

AGCCAAAGGGCAGCCCCGAGAACCACAGGTGTACACCCTGCCCCCATCCCGGGATG

AGCTGACCAAGAACCAGGTCAGCCTGACCTGCCTGGTCAAAGGCTTCTATCCCAGC

GACATCGCCGTGGAGTGGGAGAGCAATGGGCAGCCGGAGAACAACTACAAGACCA

CGCCTCCCGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCATGAGGCT

CTGCACAACCACTACACGCAGAAGAGCCTCTCCCTGTCTCCGGGTAAATAG
```

Hybrid 4 open reading frame (SEQ ID NO: 24)
```
ATGCGGCTTCCGGGTGCGATGCCAGCTCTGGCCCTCAAAGGCGAGCTGCTGTTGCTG

TCTCTCCTGTTACTTCTGGAACCACAGATCTCTCAGGGCCTGGTCGTCACACCCCCG

GGGCCAGAGCTTGTCCTCAATGTCTCCAGCACCTTCGTTCTGACCTGCTCGGGTTCA

GCTCCGGTGGTGTGGGAACGGATGTCCCAGGAGCCCCCACAGGAAATGGCCAAGGC

CCAGGATGGCACCTTCTCCAGCGTGCTCACACTGACCAACCTCACTGGGCTAGACAC

GGGAGAATACTTTTGCACCCACAATGACTCCCGTGGACTGGAGACCGATGAGCGGA

AACGGCTCTACATCTTTGTGCCAGATCCCACCGTGGGCTTCCTCCCTAATGATGCCG

AGGAACTATTCATCTTTCTCACGGAAATAACTGAGATCACCATTCCATGCCGAGTAA

CAGACCCACAGCTGGTGGTGACACTGCACGAGAAGAAAGGGGACGTTGCACTGCCT

GTCCCCTATGATCACCAACGTGGCTTTTTTGGTATCTTTGAGGACAGAAGCTACATCT

GCAAAACCACCATTGGGGACAGGGAGGTGGATTCTGATGCCTACTATGTCTACAGA

CTCCAGGTGTCATCCATCAACGTCTCTGTGAACGCAGTGCAGACTGTGGTCCGCCAG

GGTGAGAACATCACCCTCATGTGCATTGTGATCGGGAATGAGGTGGTCAACTTCGAG

TGGACATACCCCCGCAAAGAAAGTGGGCGGCTGGTGGAGCCGGTGACTGACTTCCT

CTTGGATATGCCTTACCACATCCGCTCCATCCTGCACATCCCCAGTGCCGAGTTAGA

AGACTCGGGGACCTACACCTGCAATGTGACGGAGAGTGTGAATGACCATCAGGATG

AAAAGGCCATCAACATCACCGTGGTTGAGAGCGGCTACGTTCCAGCTCCTCTTCCT

CAAGCTCGAGACCTTTCGTAGAGATGTACAGTGAAATCCCCGAAATTATACACATGA

CTGAAGGAAGGGAGCTCGTCATTCCCTGCCGGGTTACGTCACCTAACATCACTGTTA

CTTTAAAAAAGTTTCCACTTGACACTTTGATCCCTGATGGAAAACGCATAATCTGGG

ACAGTAGAAAGGGCTTCATCATATCAAATGCAACGTACAAAGAAATAGGGCTTCTG

ACCTGTGAAGCAACAGTCAATGGGCATTTGTATAAGACAAACTATCTCACACATCGA

CAAACCGGTGGAGGTGGAGGTGGAGGTGGAGGTCCTAAATCTTGTGACAAAACTCA

CACATGCCCACCGTGCCCAGCACCTGAACTCCTGGGGGACCGTCAGTCTTCCTCTT

CCCCCCAAAACCCAAGGACACCCTCATGATCTCCCGGACCCCTGAGGTCACATGCGT

GGTGGTGGACGTGAGCCACGAAGACCCTGAGGTCAAGTTCAACTGGTACGTGGACG

GCGTGGAGGTGCATAATGCCAAGACAAAGCCGCGGGAGGAGCAGTACAACAGCAC
```

```
GTACCGTGTGGTCAGCGTCCTCACCGTCCTGCACCAGGACTGGCTGAATGGCAAGG

AGTACAAGTGCAAGGTCTCCAACAAAGCCCTCCCAGCCCCCATCGAGAAAACCATC

TCCAAAGCCAAAGGGCAGCCCCGAGAACCACAGGTGTACACCCTGCCCCCATCCCG

GGATGAGCTGACCAAGAACCAGGTCAGCCTGACCTGCCTGGTCAAAGGCTTCTATC

CCAGCGACATCGCCGTGGAGTGGGAGAGCAATGGGCAGCCGGAGAACAACTACAA

GACCACGCCTCCCGTGCTGGACTCCGACGGCTCCTTCTTCCTCTACAGCAAGCTCAC

CGTGGACAAGAGCAGGTGGCAGCAGGGGAACGTCTTCTCATGCTCCGTGATGCATG

AGGCTCTGCACAACCACTACACGCAGAAGAGCCTCTCCCTGTCTCCGGGTAAATAG
```

PDGFRBPR6SpeI F nucleic acid primer
(SEQ ID NO: 25)
GACTAGTATGCGGCTTCCGGGTG

PDGFRBPR7AgeI R nucleic acid primer
(SEQ ID NO: 26)
ACCGGTGGATGACACCTGGAGTCTG

PDGFRB-PR1-Acc F nucleic acid primer
(SEQ ID NO: 27)
CTATGTCTACAGACTCCAGGTGTC

D5-PR9-AgeI-Rev R nucleic acid primer
(SEQ ID NO: 28)
ACCGGTAAAGGGCAAGGAGTGTGGC

PDGF02 F nucleic acid primer
(SEQ ID NO: 29)
CCTCCACCGGTGTAGCCGCTCTCAACCACGGT

PDGF03 R nucleic acid primer
(SEQ ID NO: 30)
CCCGGGACTAGTATGCGGCTTCCGGGTG

D5-SV40 F nucleic acid primer
(SEQ ID NO: 31)
CCGGTTAGGGA

D5-SV40 B-2 nucleic acid primer
(SEQ ID NO: 32)
GGCCTCCCTAA

D4-SV40 F nucleic acid primer
(SEQ ID NO: 33)
TGAGGTCCAGCTCTCCTTCCAGCTACAGATCAATGTCCCTGTCCGAGTGCTGGAGTA
GC D4-SV40 B nucleic acid primer
(SEQ ID NO: 34)
GGCCGCTACTCCAGCACTCGGACAGGGACATTGATCTGTAGCTGGAAGGAGAGCTG
GACC Kozak-SP-D2-9Ser synthetic nucleic acid fragment
(SEQ ID NO: 35)
ACTAGTGGCGGCCGCCACCATGGTCAGCTACTGGGACACCGGGGTCCTGCTGTGCG

CGCTGCTCAGCTGTCTGCTTCTCACAGGATCTGGTAGACCTTTCGTAGAGATGTACA

GTGAAATCCCCGAAATTATACACATGACTGAAGGAAGGGAGCTCGTCATTCCCTGCC

GGGTTACGTCACCTAACATCACTGTTACTTTAAAAAAGTTTCCACTTGACACTTTGAT

CCCTGATGGAAAACGCATAATCTGGGACAGTAGAAAGGGCTTCATCATATCAAATG

CAACGTACAAAGAAATAGGGCTTCTGACCTGTGAAGCAACAGTCAATGGGCATTTG

TATAAGACAAACTATCTCACACATCGACAAACCTCGAGTTCCAGCTCCTCTTCCTCA

AGCCAGATCT

-continued

D2-2220-2908 synthetic nucleic acid fragment
(SEQ ID NO: 36)
CCACGCTGCTGGGGAACAGTTCCGAAGAGGAGAGCCAGCTGGAGACTAACGTGACG

TACTGGGAGGAGGAGCAGGAGTTTGAGGTGGTGAGCACACTGCGTCTGCAGCACGT

GGATCGGCCACTGTCGGTGCGCTGCACGCTGCGCAACGCTGTGGGCCAGGACACGC

AGGAGGTCATCGTGGTGCCACACTCCTTGCCCTTTAGTTCCAGCTCCTCTTCCTCAAG

CTCGAGACCTTTCGTAGAGATGTACAGTGAAATCCCCGAATTATACACATGACTGA

AGGAAGGGAGCTCGTCATTCCCTGCCGGGTTACGTCACCTAACATCACTGTTACTTT

AAAAAAGTTTCCACTTGACACTTTGATCCCTGATGGAAAACGCATAATCTGGGACAG

TAGAAAGGGCTTCATCATATCAAATGCAACGTACAAAGAAATAGGGCTTCTGACCT

GTGAAGCAACAGTCAATGGGCATTTGTATAAGACAAACTATCTCACACATCGACAA

ACCGGTGGAGGTGGAGGTGGAGGTGGAGGTCCTAAATCTTGTGACAAAACTCACAC

ATGCCCACCGTGCCCAGCACCTGAACTCCTGGGGGGACCGTCAGTCTTCCTCTTCCC

CCCAAAACCCAAGGACACCCTCATGATCTCCCGGACCCCTGAGGTCACATGCGTGGT

GGTGGACGTG

D3-Fc synthetic nucleic acid fragment
(SEQ ID NO: 37)
GACTGTGGTCCGCCAGGGTGAGAACATCACCCTCATGTGCATTGTGATCGGGAATGA

GGTGGTCAACTTCGAGTGGACATACCCCCGCAAAGAAAGTGGGCGGCTGGTGGAGC

CGGTGACTGACTTCCTCTTGGATATGCCTTACCACATCCGCTCCATCCTGCACATCCC

CAGTGCCGAGTTAGAAGACTCGGGGACCTACACCTGCAATGTGACGGAGAGTGTGA

ATGACCATCAGGATGAAAAGGCCATCAACATCACCGTGGTTGAGAGCGGCTACACC

GGTGGAGGTGGAGGTGGAGGTGGAGGTCCTAAATCTTGTGACAAAACTCACACATG

CCCACCGTGCCCAGCACCTGAACTCCTGGGGGGACCGTCAGTCTTCCTCTTCCCCCC

AAAACCCAAGGACACCCTCATGATCTCCCGGACCCCTGAGGTCACATGCGTGGTGG

TGGACGTG

D3-F(D2) synthetic nucleic acid fragment
(SEQ ID NO: 38)
GACTGTGGTCCGCCAGGGTGAGAACATCACCCTCATGTGCATTGTGATCGGGAATGA

GGTGGTCAACTTCGAGTGGACATACCCCCGCAAAGAAAGTGGGCGGCTGGTGGAGC

CGGTGACTGACTTCCTCTTGGATATGCCTTACCACATCCGCTCCATCCTGCACATCCC

CAGTGCCGAGTTAGAAGACTCGGGGACCTACACCTGCAATGTGACGGAGAGTGTGA

ATGACCATCAGGATGAAAAGGCCATCAACATCACCGTGGTTGAGAGCGGCTACAGT

TCCAGCTCCTCTTCCTCAAGCTCGAGACCTTTCGTAGAGATGTACAGTGAAATCCCC

GAAATTATACACATGACTGAAGGAAGGGAGCTCGTCATTCCCTGCCGGGTTACGTCA

CCTAACATCACTGTTACTTTAAAAAAGTTTCCACTTGACACTTTGATCCCTGATGGAA

AACGCATAATCTGGGACAGTAGAAAGGGCTTCATCATATCAAATGCAACGTACAAA

GAAATAGGGCTTCTGACCTGTGAAGCAACAGTCAATGGGCATTTGTATAAGACAAA

CTATCTCACACATCGACAAACCGGTGGAGGTGGAGGTGGAGGTGGAGGTCCTAAAT

CTTGTGACAAAACTCACACATGCCCACCGTGCCCAGCACCTGAACTCCTGGGGGGA

CCGTCAGTCTTCCTCTTCCCCCCAAAACCCAAGGACACCCTCATGATCTCCCGGACC

CCTGAGGTCACATGCGTGGTGGTGGACGTG

-continued sFLT02 (D2-9Gly-CH3) amino acid sequence (SEQ ID NO: 39)

MVSYWDTGVLLCALLSCLLLTGSGRPFVEMYSEIPEIIHMTEGRELVIPCRVTSPNITVTL

KKFPLDTLIPDGKRIIWDSRKGFIISNATYKEIGLLTCEATVNGHLYKTNYLTHRQTGGG

GGGGGGQPREPQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSLSPGK sFLT02 (D2-9Gly-CH3) open reading frame (SEQ ID NO: 40)

ATGGTCAGCTACTGGGACACCGGGGTCCTGCTGTGCGCGCTGCTCAGCTGTCTGCTT

CTCACAGGATCTGGTAGACCTTTCGTAGAGATGTACAGTGAAATCCCCGAAATTATA

CACATGACTGAAGGAAGGGAGCTCGTCATTCCCTGCCGGGTTACGTCACCTAACATC

ACTGTTACTTTAAAAAAGTTTCCACTTGACACTTTGATCCCTGATGGAAAACGCATA

ATCTGGGACAGTAGAAAGGGCTTCATCATATCAAATGCAACGTACAAAGAAATAGG

GCTTCTGACCTGTGAAGCAACAGTCAATGGGCATTTGTATAAGACAAACTATCTCAC

ACATCGACAAACCGGTGGAGGTGGAGGTGGAGGTGGAGGTCAGCCCCGAGAACCA

CAGGTGTACACCCTGCCCCCATCCCGGGATGAGCTGACCAAGAACCAGGTCAGCCT

GACCTGCCTGGTCAAAGGCTTCTATCCCAGCGACATCGCCGTGGAGTGGGAGAGCA

ATGGGCAGCCGGAGAACAACTACAAGACCACGCCTCCCGTGCTGGACTCCGACGGC

TCCTTCTTCCTCTACAGCAAGCTCACCGTGGACAAGAGCAGGTGGCAGCAGGGGAA

CGTCTTCTCATGCTCCGTGATGCATGAGGCTCTGCACAACCACTACACGCAGAAGAG

CCTCTCCCTGTCTCCGGGTAAATAG

---

What is claimed is:

1. A nucleic acid encoding a fusion protein wherein the fusion protein comprises (a) an extracellular portion of a PDGF receptor beta (PDGFRβ) comprising Ig-like domains D1-D3, (b) an extracellular portion of a VEGF receptor 1 (FLT-1) comprising an Ig-like domain D2, and (c) a multimerization domain, wherein the fusion proteins binds to a PDGF and a VEGF, and the fusion protein is arranged from N-terminus to C-terminus in the following order: (a), (b) and (c), and wherein the fusion protein does not comprise an Ig-like domain D3 of a VEGFR2.

2. A host cell comprising the nucleic acid of claim 1.

3. A method of producing a fusion protein, comprising culturing a host cell comprising the nucleic acid of claim 1 under a condition that produces the fusion protein, and recovering the fusion protein produced by the host cell.

4. The method of claim 3, wherein the host cell is a mammalian cell.

5. A vector comprising the nucleic acid of claim 1.

6. The vector of claim 5, which is a viral vector.

7. The vector of claim 6, wherein the viral vector is a recombinant adeno-associated virus vector (rAAV).

8. The vector of claim 7, wherein the rAAV vector comprises an ITR of AAV1, AAV2, AAV3, AAV4, AAV5, AAV6, AAV7, AAV8, AAV9, AAVrh8, or AAVrh10.

* * * * *